(12) United States Patent
Getts

(10) Patent No.: US 9,919,005 B2
(45) Date of Patent: *Mar. 20, 2018

(54) IMMUNE-MODIFYING NANOPARTICLES FOR THE TREATMENT OF INFLAMMATORY DISEASES

(71) Applicant: COUR PHARMACEUTICALS DEVELOPMENT COMPANY, INC., Northbrook, IL (US)

(72) Inventor: Daniel R. Getts, Northbrook, IL (US)

(73) Assignee: COUR PHARMACEUTICALS DEVELOPMENT COMPANY, INC., Northbrook, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/341,918

(22) Filed: Nov. 2, 2016

(65) Prior Publication Data

US 2017/0173071 A1    Jun. 22, 2017

Related U.S. Application Data

(63) Continuation of application No. 14/210,136, filed on Mar. 13, 2014.

(60) Provisional application No. 61/887,212, filed on Oct. 4, 2013, provisional application No. 61/865,392, filed on Aug. 13, 2013, provisional application No. 61/844,961, filed on Jul. 11, 2013, provisional application No. 61/779,182, filed on Mar. 13, 2013.

(51) Int. Cl.
| | |
|---|---|
| A61K 9/00 | (2006.01) |
| A61K 45/00 | (2006.01) |
| A61K 31/78 | (2006.01) |
| A61K 9/14 | (2006.01) |
| A61K 9/16 | (2006.01) |

(52) U.S. Cl.
CPC ............ *A61K 31/78* (2013.01); *A61K 9/0019* (2013.01); *A61K 9/14* (2013.01); *A61K 9/146* (2013.01); *A61K 9/1647* (2013.01)

(58) Field of Classification Search
None
See application file for complete search history.

(56) References Cited

U.S. PATENT DOCUMENTS

| | | | |
|---|---|---|---|
| 2006/0051407 A1* | 3/2006 | Richter | A61K 9/127 424/450 |
| 2015/0010631 A1* | 1/2015 | Getts | A61K 9/0019 424/489 |

FOREIGN PATENT DOCUMENTS

WO    WO-2013/032829 A1    3/2013

OTHER PUBLICATIONS

Chang et al., Journal of Controlled Release, 2013, 170, 287-294.*
Muller et al., J. Biomed Mater Res, 2003, Res 66A, 55-61.*
Japanese patent application No. 2016-502223, Notice of Reasons for Rejection (English translation), dated Nov. 24, 2017.

* cited by examiner

*Primary Examiner* — Abigail Vanhorn
(74) *Attorney, Agent, or Firm* — Marshall, Gerstein & Borun LLP

(57) ABSTRACT

The current invention involves the administration of negatively charged particles, such as polystyrene, PLGA, or diamond particles, to subjects to ameliorate inflammatory immune responses. Additionally, the present invention describes methods of treating inflammatory diseases by administering these same negatively charged particles.

17 Claims, 43 Drawing Sheets

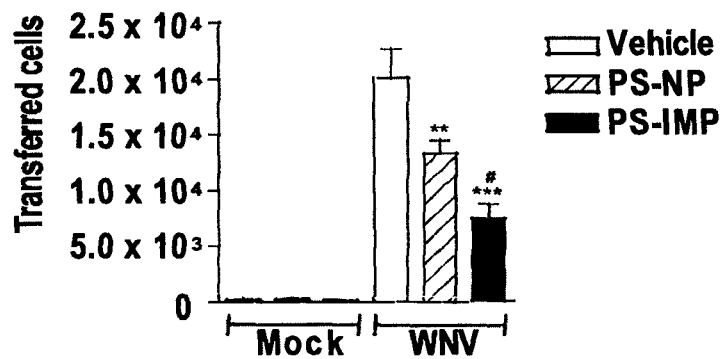
Figure 3D Brain PKH26+ ΦIM-derived macrophages
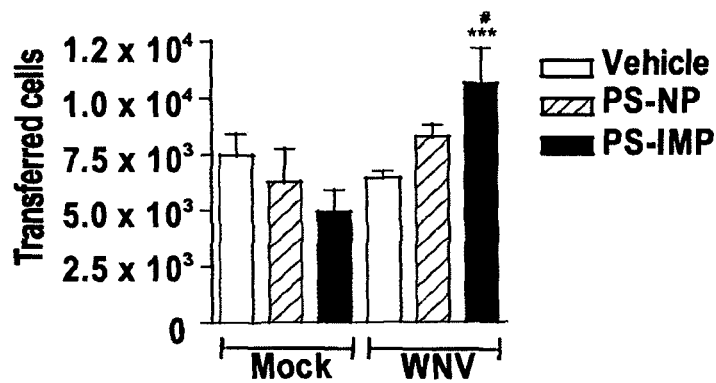
Figure 3e Spleen PKH26+ ΦIM
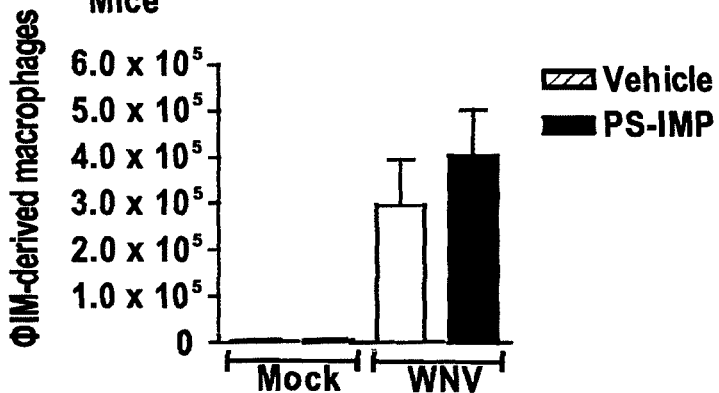
Figure 3F Brain Splenectomised Mice Figure 5E
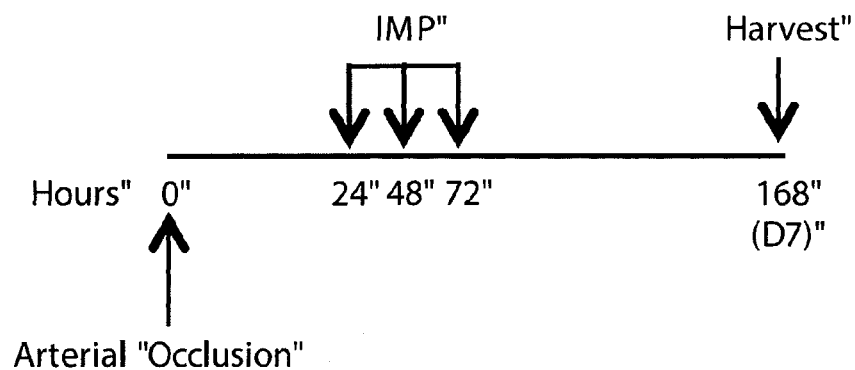
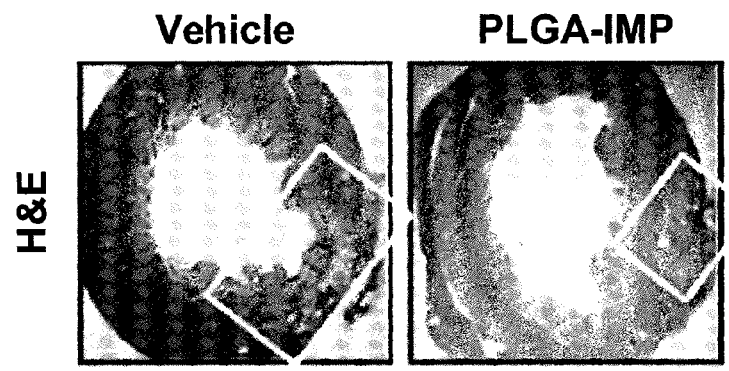
Figure 5F
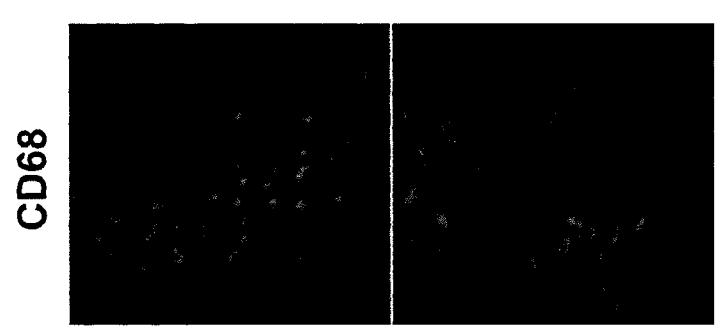
Figure 5G

CCL2

IFN-γ

IL-6

TNF

IL-10

IL-4

CCL3

IL-3

IL-15

IL-9

IL-1β

IL-2

Lectin Particles

Peritoneal Lavage

Gated on DC11b+ cells

Figure 13A Experimental Design
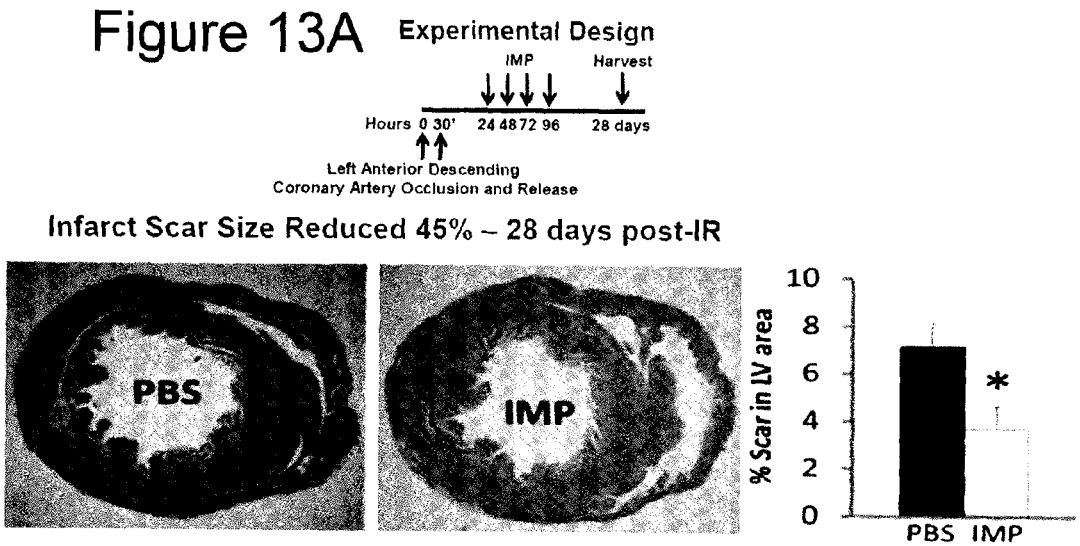
Infarct Scar Size Reduced 45% – 28 days post-IR
Figure 13B
Systolic Ejection Fraction Increased 21% – 28 days post-IR
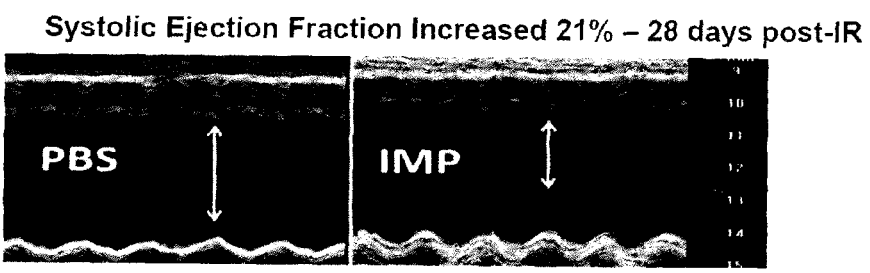

Figure 14A
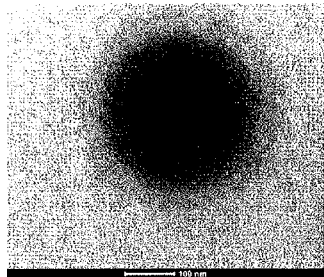
Figure 14B
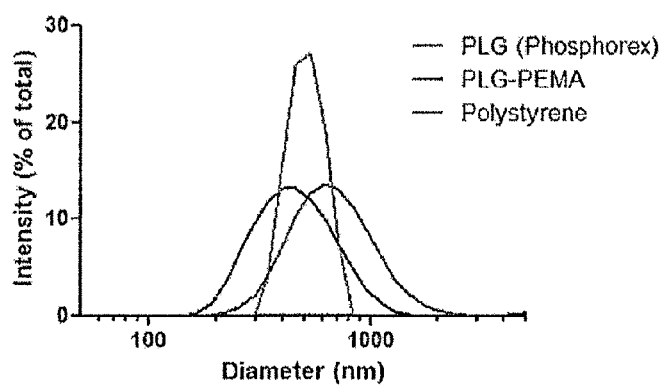
Figure 14C
| Particle | Z-average size by intensity (nm) | ζ-potential (mV) |
|---|---|---|
| PLG (Phosphorex) | 624.3 | -32.7 ± 4.71 |
| PLG-PEMA | 429.9 | -67.4 ± 10.9 |
| Polystyrene | 503.6 | -66.4 ± 6.97 |

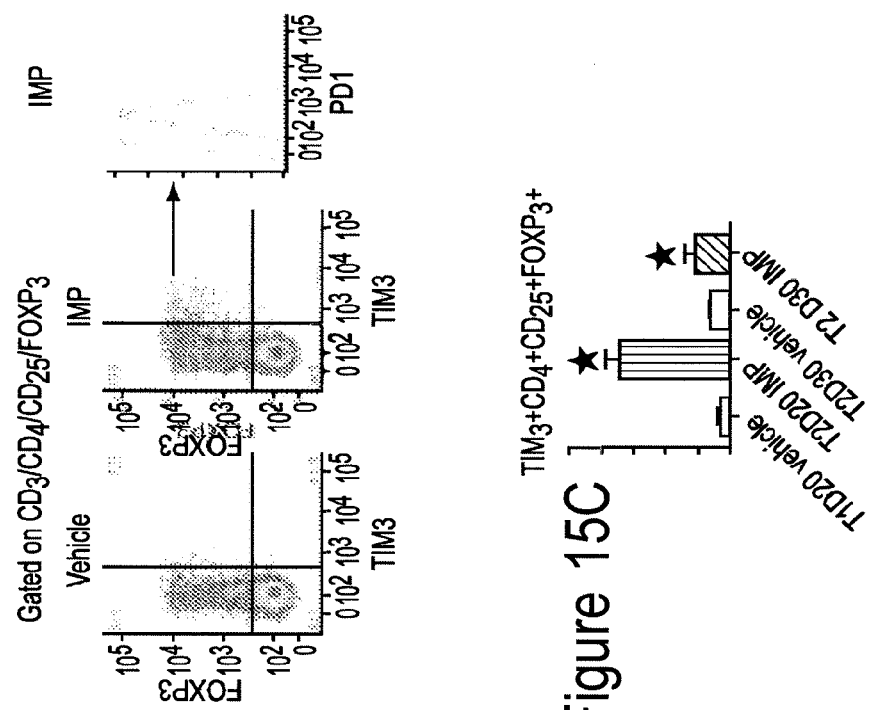
Figure 15B
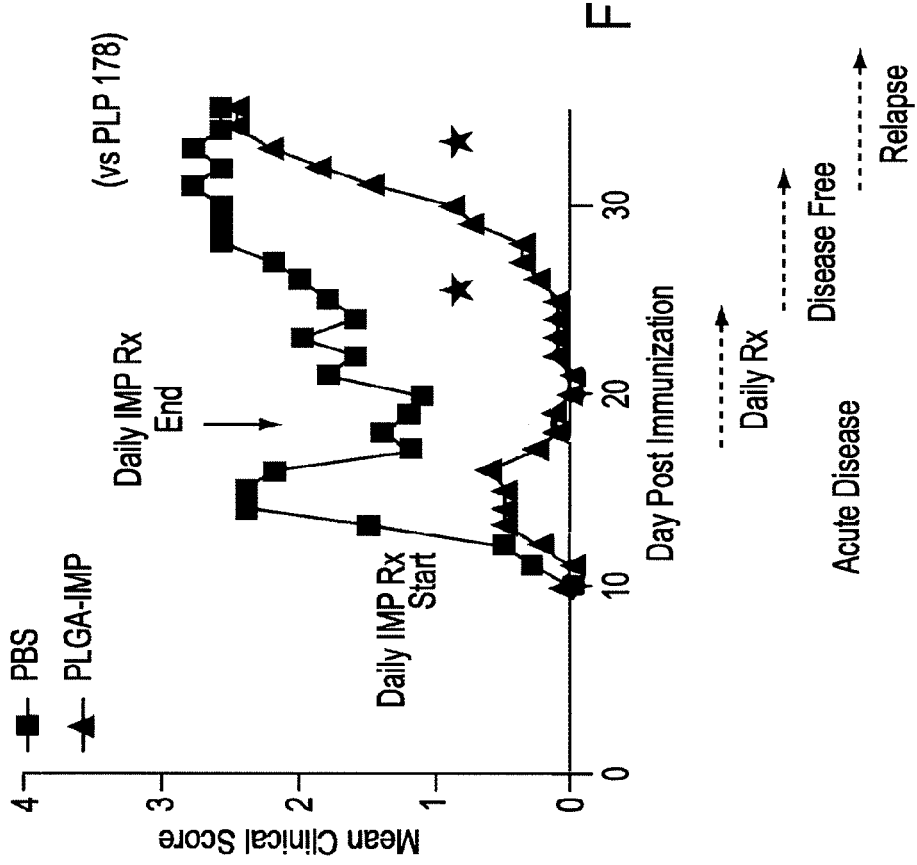
Figure 15C
Figure 15A

IMMUNE-MODIFYING NANOPARTICLES FOR THE TREATMENT OF INFLAMMATORY DISEASES

CROSS REFERENCE TO RELATED APPLICATIONS

This application is a continuation of U.S. application Ser. No. 14/210,136, filed Oct. 4, 2013, which claims priority to U.S. Provisional Application Nos. 61/779,182, filed Mar. 13, 2013; 61/844,961, filed Jul. 11, 2013, 61/865,392, filed Aug. 13, 2013 and 61/877,212, filed Oct. 4, 2013, the contents of each of which is hereby incorporated by reference in their entirety.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: COUR-001_01WO_ST25.txt, date recorded: Mar. 13, 2014, file size 1.2 megabytes).

BACKGROUND OF INVENTION

Inflammatory diseases and disorders are conditions in which an abnormal or otherwise deregulated inflammatory response contributes to the etiology or severity of disease. Examples include autoimmune diseases such as rheumatoid arthritis, multiple sclerosis, Celiac disease, and diabetes, infectious diseases such as tuberculosis and various forms of meningitis and encephalitis, including West Nile Virus encephalitis as well as ischemia reperfusion diseases such as myocardial infarction and transplant reperfusion injury. Additionally, the increase in inflammation observed after surgery, injury, or other tissue trauma can have deleterious effects on a patient's recovery.

Many of these diseases or disorders are characterized by a polynuclear/mononuclear cell infiltration at a site of tissue injury or other insult. Examples of mononuclear cells that have been observed in these infiltrations include lymphocytes, especially T lymphocytes, and cells of the mononuclear phagocyte system (MPS cells) such as monocytes, macrophages, dendritic cells, microglial cells and others.

Many of the cells observed in the mononuclear cell infiltrates are suspected of having a role in these abnormal inflammatory responses. For example, in diseases such as multiple sclerosis, CD4$^+$ T cells are known to play a central role in the pathologic autoimmune response. At an earlier time point in T cell activation, dendritic cells and other MPS cells may be responsible for activation of CD4$^+$ T cells. MPS cells could also contribute to inflammation through phagocytosis although in at least some inflammatory diseases it is not clear whether such cells would be capable of this in the absence of CD4$^+$ T cells.

Peripheral blood monocytes may be classified into one or more groups according to the expression or not of certain cell surface molecules. In particular, human "resident monocytes" or "mature monocytes" are understood to have a CD14$^{lo}$CD16$^+$ phenotype (the mouse counterpart is CX$_3$CR1$^{hi}$CCR2$^-$Gr1$^-$). Another group of cells, the "inflammatory monocytes" or "immature monocytes" are understood to have a CD14$^+$CD16$^-$ phenotype (the mouse counterpart is CX$_3$CR1$^{lo}$CCR2$^+$Gr1$^+$). (Geissmann F. et al. 2003 Immunity 19: 71-82)

Inflammatory monocytes have been found to play a role in a wide range of immune-mediated diseases and disorders. Upon entry into inflamed tissues, LY6C$^{hi}$ inflammatory monocytes differentiate into tissue macrophages or dendritic cells (DC) that may secrete numerous pro-inflammatory cytokines, proteases, and other mediators, including nitric oxide, culminating in tissue damage, scarring and even death. (Getts et al., 2008 J. Exp. Med. 205:2319-2337; Lin et al, 2011 J Immunol 186:508-515; Schiopu et al. 2012 Atherosclerosis 223:291-298; Swirski et al., 2010 J Clin Invest 120:2627-2634; Swirski et al, 2009 Science 325:612-616; Getts et al., J. Neuroinflamm. In press; Nahrendorf et al., 2010 Circulation 121:2437-2445). Inhibition of inflammatory monocytes not only reduces pathology, but may also enable early initiation of repair mechanisms in certain inflammatory conditions. To date, there is no safe and effective therapy for specifically targeting inflammatory monocytes that alters these outcomes. Physicians rely on broad-acting steroids, non-steroidal anti-inflammatory agents or antibodies that briefly neutralize components of the inflammatory monocyte response.

Considering the role of inflammatory monocytes and polymorphonuclear cells in most disease conditions, their therapeutic accessibility in the bloodstream, and their inherent propensity to interact with particles, particle-based therapeutics are potentially better equipped to specifically target these cells than antibodies or small molecules. To date, work in this area has focused on the formulation of delayed-release small-molecule therapeutics conjugated to nano- or micro-particles to enable enhanced delivery of cancer therapeutics or antigenic materials for vaccination purposes (De Jong et al., 2008 Int J Nanomedicine 3:133-149). However, the in vivo immune-modulating potential of particles themselves that do not carry active pharmaceutical ingredients has for the most part been overlooked.

Natural leukocyte clearance and the ability to induce apoptosis remains a primary goal for therapies that aim to reduce pathology associated with specific cell subsets including inflammatory derived macrophages and dendritic cells. It has been surprisingly found that immune-modified particles (IMPs) derived from polystyrene, nanodiamonds, or biodegradable poly(lactic-co-glycolic) acid, when infused are taken up by inflammatory monocytes through the macrophage receptor with collagenous structure (MARCO), triggering the migration and sequestration of monocytes in the spleen, where they undergo Caspase 3-mediated apoptosis. Perhaps more surprisingly, targeted administration of Immune-Modifying Particles (IMPs) in acute models of inflammation not only reduced inflammatory monocyte accumulation at the primary site of inflammation, but reduced pathology and disease severity in all models. IMPs are a versatile, readily translatable therapeutic option for diseases caused or potentiated by inflammatory monocytes. IMPs represent a novel and safe inflammatory monocyte specific therapy.

Regulatory T cells (or Tregs) are an immunomodulatory cell type important in controlling autoimmunity and general inflammation in the periphery. Tregs are CD4 positive cells that usually constitutively express CD25. Therefore Tregs are often CD4$^+$CD25$^+$ T cells. These regulatory T cells are potent suppressors of T cell mediated immunity in a range of inflammatory conditions including, but not limited to, infectious disease, autoimmunity, pregnancy and tumors. In vivo, a small number of Tregs can control large numbers of activated effector T cells. Although freshly isolated Tregs exhibit minimal constitutive suppressor functions, ligating the T cell antigen receptor (TCR) in vitro or pre-immunizing mice with high dose self antigen in vivo stimulates Treg suppressor function. The requirement for TCR ligation to enhance T cell suppressor function is paradoxical since most T cells are thought to recognize constitutively expressed self antigens.

It is desirable in inflammatory situations, such as autoimmune disease to enhance Treg suppressor function so as to decrease the inflammatory response to self proteins. Conversely, when attempting to mount an immune response to a tumor, for example, it may be desirable to switch off Treg function by either blocking the function of Tregs or reprogramming Tregs into effector T cells capable of an inflammatory immune response to a desired target.

SUMMARY OF THE INVENTION

The current invention involves the surprising finding that modified particles alone, that is, without a peptide coupled thereto, are effective in ameliorating the inflammatory immune response in patients in need thereof. Surprisingly, all that is necessary to dampen an inflammatory immune response, and treat inflammatory disease is the administration of negatively charged particles, without the need for coupling peptides thereto.

In one embodiment, the current invention provides a method of inducing monocyte, granulocyte and/or neutrophil apoptosis in a subject comprising administering to the subject a pharmaceutical composition comprising negatively charged particles and a carrier. In a further embodiment, the negatively charged particles are free from attached peptide or antigenic moieties. In some embodiments, the negatively charged particles are polystyrene particles. In other embodiments, the negatively charged particles are diamond particles. In still other embodiments, the negatively charged particles are poly(lactic-co-glycolic acid) (PLGA) particles. In some embodiments, the particles are PLURONICS® stabilized polypropylene sulfide particles. In still other embodiments, the negatively charged particles are carboxylated.

In one embodiment, the current invention provides a method of the induction and expansion of anti-inflammatory CD103+ dendritic cells and Regulatory T cells in a subject comprising administering to the subject a pharmaceutical composition comprising negatively charged particles and a carrier. In a further embodiment, the negatively charged particles are free from attached peptide or antigenic moieties.

In one embodiment, the current invention provides a method for removing pro-inflammatory mediators from the inflammatory milieu in a subject with an inflammatory disorder comprising administering to the subject a pharmaceutical composition comprising negatively charged particles and a carrier. In a further embodiment, the negatively charged particles are free from attached peptide or antigenic moieties. In some embodiments, the negatively charged particles are polystyrene particles. In other embodiments, the negatively charged particles are diamond particles. In still other embodiments, the negatively charged particles are poly(lactic-co-glycolic acid) (PLGA) particles. In some embodiments, the particles are PLURONICS® stabilized polypropylene sulfide particles. In a further embodiment, the negatively charged particles are carboxylated. In a further embodiment, the negatively charged particles bind to the pro-inflammatory polypeptides produced in the subject.

In one embodiment, the current invention provides a method for concentrating and presenting regulatory proteins from the inflammatory milieu in a subject with an inflammatory disorder comprising administering to the subject a pharmaceutical composition comprising negatively charged particles and a carrier. In a further embodiment, the negatively charged particles are free from attached peptide or antigenic moieties. In some embodiments, the negatively charged particles are polystyrene particles. In other embodiments, the negatively charged particles are diamond particles. In still other embodiments, the negatively charged particles are poly(lactic-co-glycolic acid) (PLGA) particles. In some embodiments, the particles are PLURONICS® stabilized polypropylene sulfide particles. In a further embodiment, the negatively charged particles are carboxylated. In a further embodiment, the negatively charged particles bind to the regulatory proteins produced in the subject.

In still a further embodiment, the current invention provides a method for controlling a pathologic and/or unwanted inflammatory immune response in a subject comprising administering to the subject a pharmaceutical composition comprising negatively charged particles that have been pre-absorbed with regulatory proteins such that upon administration the negatively charged particles concentrate and present the regulatory proteins to ameliorate the inflammatory immune response in the subject. In a further embodiment, the negatively charged particles are free from attached peptide or antigenic moieties. In some embodiments, the negatively charged particles are polystyrene particles. In other embodiments, the negatively charged particles are diamond particles. In still other embodiments, the negatively charged particles are poly(lactic-co-glycolic acid) (PLGA) particles. In some embodiments, the particles are PLURONICS® stabilized polypropylene sulfide particles. In a further embodiment, the negatively charged particles are carboxylated.

In one embodiment, the current invention provides a method of inducing antigen specific tolerance in a subject comprising administering to said subject a pharmaceutical composition comprising negatively charged particles with one or more antigens embedded therein, and a carrier. In a further embodiment, the negatively charged particles are free from attached peptide or antigenic moieties. In some embodiments, the negatively charged particles are polystyrene particles. In other embodiments, the negatively charged particles are diamond particles. In still other embodiments, the negatively charged particles are poly(lactic-co-glycolic acid) (PLGA) particles. In some embodiments, the particles are PLURONICS® stabilized polypropylene sulfide particles. In a further embodiment, the negatively charged particles are carboxylated. In a further embodiment, the negatively charged particles bind to the pro-inflammatory polypeptides produced in the subject.

In one embodiment, the particles are coupled to an antigen comprising one or more epitopes. In a further embodiment, the epitope is associated with an allergy, an autoimmune disease, or an inflammatory disease or disorder. In one embodiment, the epitope is associated with type 1 diabetes, multiple sclerosis, Celiac's disease, or inflammatory bowel disease, including Crohn's disease or colitis, e.g. ulcerative colitis. In one embodiment, the epitope is an epitope described in Tables 1 or 2. In one embodiment, the particles are coupled to antigens comprising only one epitope associated with one disease and/or disorder. In a further embodiment, antigens comprise more than one epitope associated with the same disease and/or disorder. In a further embodiment, the antigens comprise more than one epitope associated with different diseases and/or disorders.

In one embodiment, the negatively charged particles have a zeta potential of less than about −100 mV. In another embodiment, the negatively charged particles have a zeta potential of less than about −50 mV. In one embodiment, the negatively charged particles have a zeta potential between −100 mV and 0 mV. In some embodiments, the negatively charged particles with a zeta potential between −75 mV and 0 mV are carboxylated. In another embodiment, the negatively charged particles have a zeta potential between −60 mV and 0 mV. In another embodiment, the negatively charged particles have a zeta potential between −50 mV and 0 mV. In a particular embodiment, the negatively charged particles have a zeta potential between −50 mV and −40 mV. In another embodiment, the charged particles have a zeta potential between −100 mV and −50 mV. In one embodiment, the charged particles have a zeta potential between −75 mV and −50 mV.

In one embodiment, the pharmaceutical formulations of the current invention decrease and/or inhibit the infiltration of inflammatory monocytes to inflammatory foci. In another embodiment, the pharmaceutical formulations of the current invention ameliorate an inflammatory immune response.

In one embodiment, the pharmaceutical formulations of the current invention increase the number of regulatory T cells. In another embodiment, the pharmaceutical formulations of the current invention ameliorate an inflammatory immune response.

In one embodiment, the pharmaceutical formulations of the current invention comprise negatively charged particles with an average diameter of about 0.1 µm to about 10 µm. In another embodiment the negatively charged particles have an average diameter of about 0.2 µm to about 2. µm. In a further embodiment, the negatively charged particles have an average diameter of about 0.3 µm to about 5 µm. In yet a further embodiment the negatively charged particles have an average diameter of about 0.5 µm to about 3 µm. In still a further embodiment, the negatively charged particles have an average diameter of about 0.5 µm.

In one embodiment, the subject has undergone or will undergo surgery. In a further embodiment, the negatively-charged particles are administered to the subject before surgery. In yet a further embodiment, the negatively-charged particles are administered to the subject during surgery. In yet a further embodiment, the negatively-charged particles are administered to the subject after surgery. In another embodiment, the subject is a transplant recipient.

In a further embodiment, the subject has recently experienced physical trauma. In a further embodiment, the subject has recently experienced an injury. In yet a further embodiment, the injury is a sports injury. In a further embodiment, the injury is a concussion.

In one embodiment, the subject has an autoimmune disorder. In a further embodiment the autoimmune disorder is multiple sclerosis, scleroderma, type-I diabetes, rheumatoid arthritis, thyroiditis, systemic lupus erythematosus, Reynaud's syndrome, Sjorgen's syndrome, autoimmune uveitis, autoimmune myocarditis, inflammatory bowel disease, Amyotrophic Lateral Sclerosis (ALS), Celiac disease, ulcerative colitis, or Crohn's disease. In a particular embodiment, the autoimmune disease is multiple sclerosis. In a further embodiment, the autoimmune disease is Celiac disease. In a further embodiment, the autoimmune disease is type 1 diabetes. In a further embodiment, the autoimmune disease is inflammatory bowel disease, including Crohn's disease and ulcerative colitis.

In one embodiment, the subject has an allergic disorder. In a further embodiment, the allergic disorder is eczema, asthma, allergic rhinitis or skin hypersensitivity. In another embodiment, the subject is a transplant recipient.

In one embodiment, the subject has ischemic reperfusion injury, atherosclerosis, or has suffered from a cardiac infarction. In another embodiment, the subject has psoriasis or dermatitis.

In one embodiment, the subject has a viral infection. In a further embodiment, the viral infection is a herpes virus infection, a hepatitis virus infection, a west nile virus infection, a flavivirus, an influenza infection, a rhinovirus infection, a papillomavirus infection, a or parainfluenza virus infection. In a further embodiment, the viral infection infects the central nervous system of said subject. In still a further embodiment, the viral infection causes viral encephalitis or viral meningitis.

In one embodiment, the subject has a bacterial infection. In a further embodiment, the bacterial infection infects the central nervous system of said subject. In still a further embodiment, the bacterial infection causes sepsis bacterial encephalitis or bacterial meningitis.

In a further embodiment, the administration of the particles of the invention prevents the accumulation of potentially pathology causing neutrophils and other granulocytes in a subject. In a further embodiment, the subject has cancer.

In one embodiment, administration of the particles of the invention increases regeneration of damaged tissue in a subject. In one embodiment, administration of the particles of the invention increases regeneration of damaged tissue in a subject with amyotrophic lateral sclerosis (ALS) or post traumatic stress disorder (PTSD). In a further embodiment, administration of the particles increases regeneration of epithelial cells. In yet a further embodiment, administration of the particles increases remyelination of neurons. In another embodiment, the subject has an autoimmune disease. In yet another embodiment, the subject has inflammatory bowel disease, ulcerative colitis, and/or Crohn's disease. In yet another embodiment, the subject has multiple sclerosis. In one embodiment, administration of the negatively charged particles induces antigen-specific tolerance in a subject. In one embodiment, the particles that induce antigen-specific tolerance comprise one or more epitopes associated with an allergy, autoimmune disease, and/or inflammatory disease. In one embodiment, the epitopes are selected from those described in Tables 1 or 2. In one embodiment, the negatively charged particles are polystyrene, diamond, PLURONICS® stabilized polypropylene sulfide, or poly(lacti-co-glycolic acid) particles. In one embodiment the particles are carboxylated. In one embodiment, the particles have a zeta potential of less than about −100 mV. In one embodiment, the particles have a zeta potential between about −75 mV and 0 mV, for example, between −50 mV and 0 mV, or between −100 mV and −50 mV or between −75 mV and −50 mV or between −50 mV and −40 mV. In one embodiment, the particle has an average diameter of about 0.1 µm to about 10 µm, for example from about 0.2 µm to about 2 µm or about 0.3 µm to about 5 µm, or 0.5 µm to about 3 µm or about 0.5 µm to about 1 µm.

In one embodiment, the subject has an autoimmune disease. In one embodiment, the autoimmune disease is multiple sclerosis, scleroderma, type-I diabetes, rheumatoid arthritis, thyroiditis, systemic lupus erythematosus, Reynaud's syndrome, Sjorgen's syndrome, autoimmune uveitis, autoimmune myocarditis, inflammatory bowel disease, Amyotrophic Lateral Sclerosis (ALS), Celiac disease, ulcerative colitis, or Crohn's disease. In one embodiment, the particle comprises one or more myelin basic protein epitope. In one embodiment, the myelin basic protein epitope is one or more of SEQ ID NO: 4975 or SEQ ID NO: 4976. In one embodiment, the particles comprise one or more myelin oligodendrocyte glycoprotein epitope. In one embodiment, the myelin oligodendrocyte glycoprotein epitope is one or more of SEQ ID NO: 1 or SEQ ID NO: 4978. In one embodiment, the particle contains one or more insulin epitopes. In one embodiment, the one or more insulin epitopes is SEQ ID NO: 4981. In one embodiment, the particle comprises one or more glutamic acid decarboxylase epitopes. In one embodiment, the glutamic acid decarboxylase epitopes is SEQ ID NO: 4982. In one embodiment, the particle contains one or more proteolipid protein epitopes. In one embodiment, the proteolipid protein epitope is SEQ ID NO: 4977. In one embodiment, the particle comprises one or more gliaden epitopes. In one embodiment, the gliaden epitopes comprise SEQ ID NO: 4983-4985.

In one embodiment, the method includes administering the negatively charged particles by any suitable means. In one embodiment, the composition is administered orally, nasally, intravenously, intramuscularly, ocularly, transdermally, or subcutaneously. In a particular embodiment, the carboxylated particles are administered nasally. In still another embodiment, the negatively charged particles are administered intravenously. In still another embodiment, the negatively charged particles are administered subcutaneously.

In one embodiment, the method includes a method of diagnosing an inflammatory condition in a subject. In a particular embodiment, the method includes removing blood from a subject and incubating the blood, or serum/plasma derived therefore, with negatively charged particles and determining the presence or absence of the proteins listed in Table 6, wherein the presence of one or more proteins of Table 6 is indicative of an inflammatory immune response. In another embodiment, the method includes injecting a pharmaceutical composition comprising negatively charged particles into the circulation of a subject and subsequently removing the particles from the circulation and determining the presence or absence of the proteins listed in Table 6 on the surface of the particles removed from the subject wherein the presence of one or more proteins of Table 6 is indicative of an inflammatory immune response.

BRIEF DESCRIPTION OF THE DRAWINGS

FIG. 13 shows (A-B) that PLGA-IMP infusion protects from inflammatory damage in a myocardial ischemia (LAD occlusion)-reperfusion model. The coronary artery was occluded and blood flow was allowed to return after 30 minutes. Mice were treated with PLGA-IMP for 4 days. Treatment with PLGA-IMPs significantly reduced the infarct scar size and systolic ejection fraction compared with the PBS-control animals.

FIG. 14 shows (A) a micrograph of a poly(lactide-co-glycolide) (PLG) particle. B and C show the characterization of surface-functionalized poly(lactide-co-glycolide) particles by dynamic light scattering analysis, including the average size (nm) and ζ potential (mV) of PLG-PEMA particles. Surface-functionalized poly(lactide-co-glycolide) particles were analyzed on a Malvern Zetasizer Nano ZS (Malvern Instruments, Westborough, Mass.) at a count rate of 2.5×10$^5$ counts per second in 18.2 MΩ water. The population of surface-functionalized poly(lactide-co-glycolide) particles varied by 5-15% per batch but generally had a Z-average diameter of 567 nm, a peak diameter of 670 nm and a polydispersity index of 0.209.

FIG. 15 shows (A) shows that PLGA-IMP infusion protects from inflammatory damage in EAE. Upon treatment cessation, there is a disease free period, however, over time disease returns. (B) PLGA-IMP infusion (but not vehicle control) results in the expansion and induction of regulatory T cells that express anti-inflammatory proteins like PD-1. (C) These Tregs are most abundant during IMP treatment, and wane over time after treatment cessation.

DETAILED DESCRIPTION OF THE INVENTION

Figure 1A:
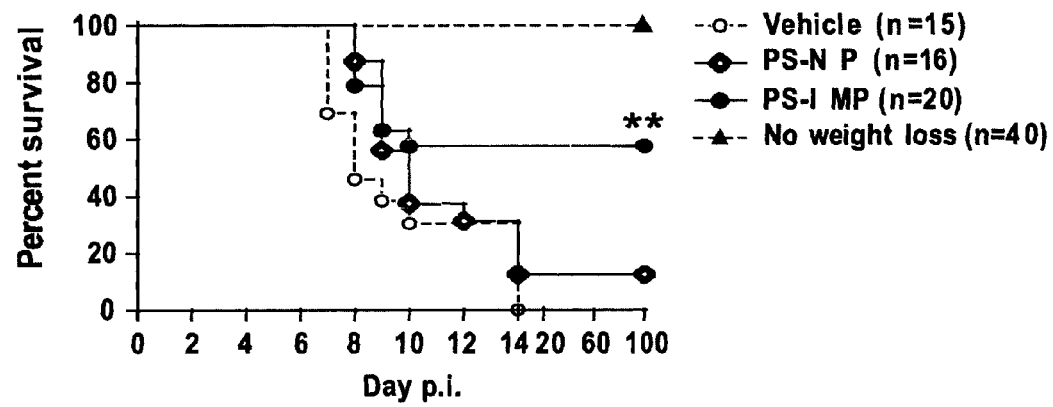
FIG. 1 shows (A-G) the ability of treatment of WNV-infected mice with PS-IMP to ameliorate disease pathology. Treatment of WNV-infected mice with PS-IMP at the time of ≥5% weight loss results in survival of 60% of mice that would otherwise succumb to disease (a). This effect was significantly diminished in mice treated with Polystyrene neutral particles (PSNP) and absent in vehicle controls (a). Infiltration of inflammatory monocyte-derived macrophages into tested for their ability to inhibit monocyte migration into the thioglycollate-inflamed peritoneum (regimen shown in a). WT and MARCO$^{-/-}$ mice respond similarly to thioglycollate injection, as determined by the number of Ly6C$^{hi}$/CD11b$^+$ monocytes (ΦIM) isolated from the peritoneum (b, e). PS-IMP treatment (as shown in a), significantly reduced ΦIM infiltration into the peritoneal cavity at 48 hours in WT animals injected with thioglycollate but did not reduce ΦIM isolated from the peritoneal cavity of MARCO$^{-/-}$ mice (b, e). FITC-PS-IMP (green) were found in association with MARCO$^+$ (red fluorescence) cells in the marginal zone of the spleen (c). WNV infection upregulates MARCO expression on ΦIM (d). In thioglycollate-injected WT mice, PS-IMP treatment was associated with a significant increase in numbers of ΦIM in the spleen, which was not observed in MARCO$^{-/-}$ animals (b, e). Significantly higher numbers of PS-IMP$^+$ Ly6C$^{hi}$ ΦIM were isolated from spleens of thioglycolate-injected WT mice compared to MARCO$^{-/-}$ animals (f). Infusion of PS-IMP into thioglycolate-induced WT mice resulted in a significant increase in numbers of Ly6C$^{hi}$ ΦIM which expressed the apoptosis markers annexin V (g, h) and caspase-3 (i). This was not observed in MARCO$^{-/-}$ animals. Flow cytometry data are means±SD and represent three separate experiments with 4-5 mice/group. Statistical analysis was conducted using one-way ANOVA and Tukey-Kramer post-test. P≤0.05 (*), P≤0.01 (), P≤0.001 (*), in comparing the WT PS-IMP groups to all other groups.

The present inventors have surprisingly found that when negatively charged particles, such as polystyrene, PLGA, or diamond particles of a certain size and zeta potential, are administered to subjects, inflammatory immune responses are ameliorated. Additionally, the present inventors have also surprisingly found that these same negatively charged particles, when administered to subjects, induce monocyte and/or neutrophil apoptosis and improved clearance in the subject. It was also surprising that these same negatively charged particles, when administered to subjects, induce tolerogenic dendritic cells, suppressor cells, and regulatory T cells. These negatively charged particles have also been found to remove pro-inflammatory mediators from the inflammatory milieu. Similarly, the negatively charged particles may also concentrate and present regulatory mediators to further induce a regulatory T cell response or otherwise ameliorate the inflammatory immune response. Negatively charged particles, therefore, may be useful in the treatment of any disease or condition characterized by an excessive inflammatory immune response, such as autoimmune diseases, as well as in the treatment of bacterial and viral infections. Finally, particles which have been embedded with one or more antigens induce antigen-specific tolerance in a subject.

"Particle" as used herein refers to any non-tissue derived minute composition of matter, it may be a sphere or sphere-like entity or bead. The term "particle" and the term "bead" may be used interchangeably. Additionally, the term "particle" may be used to encompass beads and spheres.

"Carboxylated particles" or "carboxylated beads" or "carboxylated spheres" includes any particle that has been modified to contain a carboxyl group on its surface. In some embodiments the addition of the carboxyl group enhances phagocyte/monocyte uptake of the particles from circulation, for instance through the interaction with scavenger receptors such as MARCO. The carboxylation can be achieved using any compound which adds carboxyl groups, including, but not limited to poly(ethylene-maleic anhydride) (PEMA).

"Negatively charged particles" or "negatively charged beads" or "negatively charged spheres" include any particle that inherently possesses, or has been modified to have a negative charge. In some embodiments, particles are made to have a negative charge by carboxylation of the particles.

"Antigenic moiety" as used herein refers to any moiety, for example a peptide, that is recognized by the host's immune system. Examples of antigenic moieties include, but are not limited to, autoantigens and/or bacterial or viral proteins, peptides or components. Without being bound by theory, while the negatively charged beads themselves may be recognized by the immune system, the negatively charged beads with nothing more attached thereto are not considered an "antigenic moiety" for the purposes of the invention.

"Naked beads" or "naked particles" or "naked spheres" as used herein refers to beads, particles or spheres that have not been carboxylated or otherwise modified.

"Pro-inflammatory mediators" or "pro-inflammatory polypeptides" as used herein refers to polypeptides or fragments thereof which induce, maintain, or prolong inflammation in a subject. Examples of pro-inflammatory mediators include, but are not limited to, cytokines and chemokines.

"Inflammatory milieu" or "inflammatory foci" as used herein refers to the site of inflammation, or increased concentration of pro-inflammatory mediators, in a subject. The inflammatory milieu may encompass a subjects circulation as a whole. For example, when a subject is suffering from a systemic inflammatory disorder, inflammatory mediators may be found throughout the subject's circulation. Thus, in these embodiments, the inflammatory milieu is not contained within a discreet area.

By "Regulatory T cell" or "Treg" or "Suppressor T cell" is meant a T cell that is capable of modulating the T cell immune response. For example a Treg may be a $CD4^+$ or $CD8^+$ T cell that is capable of inhibiting the effector function of either $CD4^+$ or $CD8^+$ T cell response.

The particle may have any particle shape or conformation. However, in some embodiments it is preferred to use particles that are less likely to clump in vivo. Examples of particles within these embodiments are those that have a spherical shape.

It is not necessary that each particle be uniform in size, although the particles must generally be of a size sufficient to trigger phagocytosis in an antigen presenting cell or other MPS cell. Preferable, the particles are microscopic or nanoscopic in size, in order to enhance solubility, avoid possible complications caused by aggregation in vivo and to facilitate pinocytosis. Particle size can be a factor for uptake from the interstitial space into areas of lymphocyte maturation. A particle having an average diameter of from about 0.1 µm to about 10 µm is capable of triggering phagocytosis. Thus in one embodiment, the particle has a diameter within these limits. In another embodiment, the particle has an average diameter of about 0.2 µm to about 2 µm. In another embodiment, the particle has an average diameter of about 0.3 µm to about 5 µm. In still another embodiment, the particle has an average diameter of about 0.5 µm to about 3 µm. In a further embodiment the particle has an average size of about 0.1 µm, or about 0.2 µm or about 0.3 µm or about 0.4 µm or about 0.5 µm or about 1.0 µm or about 1.5 µm or about 2.0 µm or about 2.5 µm or about 3.0 µm or about 3.5 µm or about 4.0 µm or about 4.5 µm or about 5.0 µm In a particular embodiment the particle has a size of about 0.5 µm. The particles in a composition need not be of uniform diameter. By way of example, a pharmaceutical formulation may contain a plurality of particles, some of which are about 0.5 µm, while others are about 1.0 µm. Any mixture of particle sizes within these given ranges will be useful.

In some embodiments, the particle is non-metallic. In these embodiments the particle may be formed from a polymer. In a preferred embodiment, the particle is biodegradable in an individual. In this embodiment, the particles can provide in an individual across multiple doses without there being an accumulation of particles in the individual. Examples of suitable particles include polystyrene particles, PLGA particles, PLURIONICS stabilized polypropylene sulfide particles, and diamond particles.

Preferably the particle surface is composed of a material that minimizes non-specific or unwanted biological interactions. Interactions between the particle surface and the interstitium may be a factor that plays a role in lymphatic uptake. The particle surface may be coated with a material to prevent or decrease non-specific interactions. Steric stabilization by coating particles with hydrophilic layers such as poly(ethylene glycol) (PEG) and its copolymers such as PLURONICS® (including copolymers of poly(ethylene glycol)-bl-poly(propylene glycol)-bl-poly(ethylene glycol)) may reduce the non-specific interactions with proteins of the interstitium as demonstrated by improved lymphatic uptake following subcutaneous injections. All of these facts point to the significance of the physical properties of the particles in terms of lymphatic uptake. Biodegradable polymers may be used to make all or some of the polymers and/or particles and/or layers. Biodegradable polymers may undergo degradation, for example, by a result of functional groups reacting with the water in the solution. The term "degradation" as used herein refers to becoming soluble, either by reduction of molecular weight or by conversion of hydrophobic groups to hydrophilic groups. Polymers with ester groups are generally subject to spontaneous hydrolysis, e.g., polylactides and polyglycolides.

Particles of the present invention may also contain additional components. For example, carriers may have imaging agents incorporated or conjugated to the carrier. An example of a carrier nanosphere having an imaging agent that is currently commercially available is the Kodak X-sight nanospheres. Inorganic quantum-confined luminescent nanocrystals, known as quantum dots (QDs), have emerged as ideal donors in FRET applications: their high quantum yield and tunable size-dependent Stokes Shifts permit different sizes to emit from blue to infrared when excited at a single ultraviolet wavelength. (Bruchez, et al., Science, 1998, 281, 2013; Niemeyer, C. M Angew. Chem. Int. Ed. 2003, 42, 5796; Waggoner, A. Methods Enzymol. 1995, 246, 362; Brus, L. E. J. Chem. Phys. 1993, 79, 5566). Quantum dots, such as hybrid organic/inorganic quantum dots based on a class of polymers known as dendrimers, may used in biological labeling, imaging, and optical biosensing systems. (Lemon, et al., J. Am. Chem. Soc. 2000, 122, 12886). Unlike the traditional synthesis of inorganic quantum dots, the synthesis of these hybrid quantum dot nanoparticles does not require high temperatures or highly toxic, unstable reagents. (Etienne, et al., Appl. Phys. Lett. 87, 181913, 2005).

Particles can be formed from a wide range of materials. The particle is preferably composed of a material suitable for biological use. For example, particles may be composed of glass, silica, polyesters of hydroxy carboxylic acids, polyanhydrides of dicarboxylic acids, or copolymers of hydroxy carboxylic acids and dicarboxylic acids. More generally, the carrier particles may be composed of polyesters of straight chain or branched, substituted or unsubstituted, saturated or unsaturated, linear or cross-linked, alkanyl, haloalkyl, thioalkyl, aminoalkyl, aryl, aralkyl, alkenyl, aralkenyl, heteroaryl, or alkoxy hydroxy acids, or polyanhydrides of straight chain or branched, substituted or unsubstituted, saturated or unsaturated, linear or cross-linked, alkanyl, haloalkyl, thioalkyl, aminoalkyl, aryl, aralkyl, alkenyl, aralkenyl, heteroaryl, or alkoxy dicarboxylic acids. Additionally, carrier particles can be quantum dots, or composed of quantum dots, such as quantum dot polystyrene particles (Joumaa et al. (2006) Langmuir 22: 1810-6). Carrier particles including mixtures of ester and anhydride bonds (e.g., copolymers of glycolic and sebacic acid) may also be employed. For example, carrier particles may comprise materials including polyglycolic acid polymers (PGA), polylactic acid polymers (PLA), polysebacic acid polymers (PSA), poly(lactic-co-glycolic) acid copolymers (PLGA), [rho]oly(lactic-co-sebacic) acid copolymers (PLSA), poly(glycolic-co-sebacic) acid copolymers (PGSA), polypropylene sulfide polymers, poly(caprolactone), chitosan, etc. Other biocompatible, biodegradable polymers useful in the present invention include polymers or copolymers of caprolactones, carbonates, amides, amino acids, orthoesters, acetals, cyanoacrylates and degradable urethanes, as well as copolymers of these with straight chain or branched, substituted or unsubstituted, alkanyl, haloalkyl, thioalkyl, aminoalkyl, alkenyl, or aromatic hydroxy- or di-carboxylic acids. In addition, the biologically important amino acids with reactive side chain groups, such as lysine, arginine, aspartic acid, glutamic acid, serine, threonine, tyrosine and cysteine, or their enantiomers, may be included in copolymers with any of the aforementioned materials to provide reactive groups for conjugating to antigen peptides and proteins or conjugating moieties. Biodegradable materials suitable for the present invention include diamond, PLA, PGA, polypropylene sulfide polymers, and PLGA polymers. Biocompatible but non-biodegradable materials may also be used in the carrier particles of the invention. For example, non-biodegradable polymers of acrylates, ethylene-vinyl acetates, acyl substituted cellulose acetates, non-degradable urethanes, styrenes, vinyl chlorides, vinyl fluorides, vinyl imidazoles, chlorosulphonated olefins, ethylene oxide, vinyl alcohols, TEFLON® (DuPont, Wilmington, Del.), and nylons may be employed.

In one embodiment, the buffer solution contacting the immune modified particle may have a basic pH. Suitable basic pH for the basic solution include 7.1, 7.5, 8.0, 8.5, 9.5, 10.0 10.5, 11.0, 11.5, 12.0, 12.5, 13.0, and 13.5. The buffer solution may also be made of any suitable base and its conjugate. In some embodiments of the invention, the buffer solution may include, without limitation, sodium bicarbonate, potassium bicarbonate, lithium bicarbonate, potassium dihydrogen phosphate, sodium dihydrogen phosphate, or lithium dihydrogen phosphate and conjugates thereof.

In one embodiment of the invention, the immune modified particles contain co-polymers. These co-polymers may have varying molar ratio. Suitable co-polymer ratio of present immune modified particles may be 25:75, 30:70, 35:65, 40:60, 45:55, 50:50, 55:45, 60:40, 65:35, 70:30, 75:25, 80:20, 81:19, 82:18, 83:17, 84:16, 85:15, 86:14, 87:13, 88:12, 89:11, 90:10, 91:9, 92:8, 93:7, 94:6, 95:5, 96:4, 97:3, 98:2, 99:1, or 100:0. In another embodiment, the co-polymer may be periodical, statistical, linear, branched (including star, brush, or comb co-polymers) co-polymers. In some embodiments, the co-polymers ratio may be, but not limited to, polystyrene:poly(vinyl carboxylate)/80:20, polystyrene:poly(vinyl carboxylate)/90:10, poly(vinyl carboxylate):polystyrene/80:20, poly(vinyl carboxylate):polystyrene/90:10, polylactic acid:polyglycolic acid/50:50, polylactic acid:polyglycolic acid/80:20, or polylactic acid:polyglycolic acid/90:10.

The particles of the instant invention can be manufactured by any means commonly known in the art. Exemplary methods of manufacturing particles include, but are not limited to, microemulsion polymerization, interfacial polymerization, precipitation polymerization, emulsion evaporation, emulsion diffusion, solvent displacement, and salting out (Astete and Sabliov, J. Biomater. Sci. Polymer Edn., 17:247-289(2006)). Manipulation of the manufacturing process for PLGA particles can control particle properties (e.g. size, size distribution, zeta potential, morphology, hydrophobicity/hydrophilicity, polypeptide entrapment, etc). The size of the particle is influenced by a number of factors including, but not limited to, the concentration of PLGA, the solvent used in the manufacture of the particle, the nature of the organic phase, the surfactants used in manufacturing, the viscosity of the continuous and discontinuous phase, the nature of the solvent used, the temperature of the water used, sonication, evaporation rate, additives, shear stress, sterilization, and the nature of any encapsulated antigen or polypeptide.

Particle size is affected by the polymer concentration; higher particles are formed from higher polymer concentrations. For example, an increase in PLGA concentration from 1% to 4% (w/v) can increase mean particle size from about 205 nm to about 290 nm when the solvent propylene carbonate is used. Alternatively, in ethyl acetate and 5% Pluronic F-127, an increase in PLGA concentration from 1% to 5% (w/v) increases the mean particle size from 120 nm to 230 nm.

The viscosity of the continuous and discontinuous phase is also an important parameter that affects the diffusion process, a key step in forming smaller particles. The size of the particles increases with an increase in viscosity of the dispersed phase, whereas the size of the particles decreases with a more viscous continuous phase. In general, the lower the phase ratio of organic to aqueous solvent, the smaller the particle size.

Homogenizer speed and agitation also affect particle size; in general, higher speeds and agitation cause a decrease in particle size, although there is a point where further increases in speed and agitation no longer decrease particle size. There is a favorable impact in the size reduction when the emulsion is homogenized with a high pressure homogenizer compared with just high stirring. For example, at a phase ration of 20% in 5% PVA, the mean particle size with stirring is 288 nm and the mean particle size with homogenization (high pressure of 300 bars) is 231 nm.

An important size reduction of the particles can be achieved by varying the temperature of the water added to improve the diffusion of the solvent. The mean particle size decreases with an increase in water temperature.

The nature of the polypeptide encapsulated in the particle also affects particle size. In general, encapsulation of hydrophobic polypeptides leads to the formation of smaller particles compared with the encapsulation of more hydrophilic polypeptides. In the double emulsion process, the entrapment of more hydrophilic polypeptides is improved by using high molecular mass PLGA and a high molecular mass of the first surfactant which causes a higher inner phase viscosity. The interaction between the solvent, polymer, and polypeptide affects the efficiency of incorporating the polypeptide into the particle.

The PLGA molecular mass impacts the final mean particle size. In general, the higher the molecular mass, the higher the mean particle size. For example, as the composition and molecular mass of PLGA varies (e.g. 12 to 48 kDa for 50:50 PLGA; 12 to 98 kDa for 75:25 PLGA) the mean particle size varies (about 102 nm-154 nm; about 132 nm to 152 nm respectively). Even when particles are the same molecular mass, their composition can affect average particle size; for example, particles with a 50:50 ratio generally form particles smaller than those with a 75:25 ratio. The end groups on the polymer also affects particle size. For example, particles prepared with ester end-groups form particles with an average size of 740 nm (PI=0.394) compared with the mean size for the acid PLGA end-group is 240 nm (PI=0.225).

The solvent used can also affect particle size; solvents that reduce the surface tension of the solution also reduce particle size.

The organic solvent is removed by evaporation in a vacuum to avoid polymer and polypeptide damage and to promote final particle size reduction. Evaporation of the organic solvent under vacuum is more efficient in forming smaller particles. For example, evaporation in vacuum produces a mean particle size around 30% smaller than the mean particle size produced under a normal rate of evaporation.

The amplitude of the sonication wavelength also affects the particle characteristics. The amplitude of the wavelength should be over 20% with 600 to 800 s of sonication to form sable miniemulsions with no more droplet size changes. However, the main draw-back of sonication is the lack of monodispersity of the emulsion formed.

Organic phases that may be used in the production of the particles of the invention include, but are not limited to, ethyl acetate, methyl ethyl ketone, propylene carbonate, and benzyl alcohol. The continuous phases that may be used, include but are not limited to the surfactant poloxamer 188.

A variety of surfactants can be used in the manufacturing of the particles of the invention. The surfactant can be anionic, cationic, or nonionic. Surfactants in the poloxamer and poloaxamines family are commonly used in particle synthesis. Surfactants that may be used, include, but are not limited to PEG, Tween-80, gelatin, dextran, pluronic L-63, PVA, methylcellulose, lecithin and DMAB. Additionally, biodegradable and biocompatible surfactants including, but not limited to, vitamin E TPGS (D-α-tocopheryl polyethylene glycol 1000 succinate). In certain embodiments, two surfactants are needed (e.g. in the double emulsion evaporation method). These two surfactants can include a hydrophobic surfactant for the first emulsion, and a hydrophobic surfactant for the second emulsion.

Solvents that may be used in the production of the particles of the invention include, but are not limited to, acetone, Tetrahydrofuran (THF), chloroform, and members of the chlorinate family, methyl chloride. The choice of organic solvents require two selection criteria: the polymer must be soluble in this solvent, and the solvent must be completely immiscible with the aqueous phase.

Salts that may be used in the production of the particles of the invention include, but are not limited to magnesium chloride hexahydrate, magnesium acetate tetrahydrate.

Common salting-out agents include, but are not limited to, electrolytes (e.g. sodium chloride, magnesium acetate, magnesium chloride), or non-electrolytes (e.g. sucrose).

The stability and size of the particles of the invention may be improved by the addition of compounds including, but not limited to, fatty acids or short chains of carbons. The addition of the longer carbon chain of lauric acid is associated with the improvement of particle characteristics. Furthermore, the addition of hydrophobic additives can improve the particle size, incorporation of the polypeptide into the particle, and release profile. Preparations of particles can be stabilized by lyophilization. The addition of a cryoprotectant such as trehalose can decrease aggregation of the particles upon lyophilization.

Suitable beads which are currently available commercially include polystyrene beads such as FluoSpheres (Molecular Probes, Eugene, Oreg.).

Physical properties are also related to a nanoparticle's usefulness after uptake and retention in areas having immature lymphocytes. These include mechanical properties such as rigidity or rubberiness. Some embodiments are based on a rubbery core, e.g., a poly(propylene sulfide) (PPS) core with an overlayer, e.g., a hydrophilic overlayer, as in PEG, as in the PPS-PEG system recently developed and characterized for systemic (but not targeted or immune) delivery. The rubbery core is in contrast to a substantially rigid core as in a polystyrene or metal nanoparticle system. The term rubbery refers to certain resilient materials besides natural or synthetic rubbers, with rubbery being a term familiar to those in the polymer arts. For example, cross-linked PPS can be used to form a hydrophobic rubbery core. PPS is a polymer that degrades under oxidative conditions to polysulphoxide and finally polysulphone, transitioning from a hydrophobic rubber to a hydrophilic, water-soluble polymer. Other sulphide polymers may be adapted for use, with the term sulphide polymer referring to a polymer with a sulphur in the backbone of the mer. Other rubbery polymers that may be used are polyesters with glass transition temperature under hydrated conditions that is less than about 37° C. A hydrophobic core can be advantageously used with a hydrophilic overlayer since the core and overlayer will tend not to mingle, so that the overlayer tends to sterically expand away from the core. A core refers to a particle that has a layer on it. A layer refers to a material covering at least a portion of the core. A layer may be adsorbed or covalently bound. A particle or core may be solid or hollow. Rubbery hydrophobic cores are advantageous over rigid hydrophobic cores, such as crystalline or glassy (as in the case of polystyrene) cores, in that higher loadings of hydrophobic drugs can be carried by the particles with the rubbery hydrophobic cores.

Another physical property is the surface's hydrophilicity. A hydrophilic material may have a solubility in water of at least 1 gram per liter when it is uncrosslinked. Steric stabilization of particles with hydrophilic polymers can improve uptake from the interstitium by reducing non-specific interactions; however, the particles' increased stealth nature can also reduce internalization by phagocytic cells in areas having immature lymphocytes. The challenge of balancing these competing features has been met, however, and this application documents the creation of nanoparticles for effective lymphatic delivery to DCs and other APCs in lymph nodes. Some embodiments include a hydrophilic component, e.g., a layer of hydrophilic material. Examples of suitable hydrophilic materials are one or more of polyalkylene oxides, polyethylene oxides, polysaccharides, polyacrylic acids, and polyethers. The molecular weight of polymers in a layer can be adjusted to provide a useful degree of steric hindrance in vivo, e.g., from about 1,000 to about 100,000 or even more; artisans will immediately appreciate that all the ranges and values within the explicitly stated ranges are contemplated, e.g., between 10,000 and 50,000.

The composition of the particles has been found to affect the length of time the particles persist in the body and tolerance requires rapid particle uptake and clearance/degradation. Since ratios of over 50:50 lactide:glycolide slow the degradation rate, the particles of the invention have a lactide:glycolide ratio of about 50:50 or below. In one embodiment the particles of the invention have about a 50:50 D,L-lactide:glycolide ratio.

The particles may incorporate functional groups for further reaction. Functional groups for further reaction include electrophiles or nucleophiles; these are convenient for reacting with other molecules. Examples of nucleophiles are primary amines, thiols, and hydroxyls. Examples of electrophiles are succinimidyl esters, aldehydes, isocyanates, and maleimides.

The efficacy of colloidal therapeutics, such as the negatively charged particles of the present invention, is closely related to the particles' in vivo distribution. The distribution of a colloidal system can be predicted by determining the zeta potential. The zeta potential is measure of the potential difference between the dispersion medium and the stationary layer of fluid attached to the dispersed particle, and indicates the degree of repulsion between adjacent, similarly charged particles in a dispersion. A high zeta potential predicts stability and good dispersion of the colloidal formulation. In preferred embodiments, the zeta potential of the pharmaceutical formulations of the present invention predicts good dispersion of the formulation in vivo.

The particles of the current invention can possess a particular zeta potential. In certain embodiments, the zeta potential is negative. In one embodiment, the zeta potential is less than about −100 mV. In one embodiment, the zeta potential is less than about −50 mV. In certain embodiments, the particles possess a zeta potential between −100 mV and 0 mV. In a further embodiment, the particles possess a zeta potential between −75 mV and 0 mV. In a further embodiment, the particles possess a zeta potential between −60 mV and 0 mV. In a further embodiment, the particles possess a zeta potential between −50 mV and 0 mV. In still a further embodiment, the particles possess a zeta potential between −40 mV and 0 mV. In a further embodiment, the particles possess a zeta potential between −30 mV and 0 mV. In a further embodiment, the particles possess a zeta potential between −20 mV and +0 mV. In a further embodiment, the particles possess a zeta potential between −10 mV and −0 mV. In a further embodiment, the particles possess a zeta potential between −100 mV and −50 mV. In a further embodiment, the particles possess a zeta potential between −75 mV and −50 mV. In a further embodiment, the particles possess a zeta potential between −50 mV and −40 mV.

The particles of the current invention can be given in any dose effective to dampen the inflammatory immune response in a subject in need thereof or to treat a bacterial or viral infection in a subject in need thereof. In certain embodiments, about $10^2$ to about $10^{20}$ particles are provided to the individual. In a further embodiment between about $10^3$ to about $10^{15}$ particles are provided. In yet a further embodiment between about $10^6$ to about $10^{12}$ particles are provided. In still a further embodiment between about $10^8$ to about $10^{10}$ particles are provided. In a preferred embodiment the preferred dose is 0.1% solids/ml. Therefore, for 0.5 µm beads, a preferred dose is approximately $4 \times 10^9$ beads, for 0.05 µm beads, a preferred dose is approximately $4 \times 10^{12}$ beads, for 3 µm beads, a preferred dose is $2 \times 10^7$ beads. However, any dose that is effective in treating the particular condition to be treated is encompassed by the current invention.

The invention is useful for treatment of immune related disorders such as autoimmune disease, transplant rejection, inflammatory diseases and/or disorders, ischemia reperfusion, stroke, myocardial infarction and allergic reactions. Substitution of a synthetic, biocompatible particle system to induce immune tolerance could lead to ease of manufacturing, broad availability of therapeutic agents, increase uniformity between samples, increase the number of potential treatment sites and dramatically reduce the potential for allergic responses to a carrier cell.

As used herein, the term "immune response" includes T cell mediated and/or B cell mediated immune responses. Exemplary immune responses include T cell responses, e.g., cytokine production and cellular cytotoxicity. In addition, the term immune response includes immune responses that are indirectly effected by T cell activation, e.g., antibody production (humoral responses) and activation of cytokine responsive cells, e.g., macrophages. Immune cells involved in the immune response include lymphocytes, such as B cells and T cells ($CD4^+$, $CD8^+$, Th1 and Th2 cells); antigen presenting cells (e.g., professional antigen presenting cells such as dendritic cells, macrophages, B lymphocytes, Langerhans cells, and nonprofessional antigen presenting cells such as keratinocytes, endothelial cells, astrocytes, fibroblasts, oligodendrocytes); natural killer cells; myeloid cells, such as macrophages, eosinophils, mast cells, basophils, and granulocytes. In some embodiments, the modified particles of the present invention are effective to reduce inflammatory cell trafficking to the site of inflammation.

As used herein, the term "inflammatory monocyte" refers to any myeloid cell expressing any combination of CD14/CD16 and CCR2. As used herein, the term "inhibitory neutrophil" encompasses monocyte derived suppressor cells, and/or neutrophils.

As used herein, the term "anergy," "tolerance," or "antigen-specific tolerance" refers to insensitivity of T cells to T cell receptor-mediated stimulation. Such insensitivity is generally antigen-specific and persists after exposure to the antigenic peptide has ceased. For example, anergy in T cells is characterized by lack of cytokine production, e.g., IL-2. T-cell anergy occurs when T cells are exposed to antigen and receive a first signal (a T cell receptor or CD-3 mediated signal) in the absence of a second signal (a costimulatory signal). Under these conditions, re-exposure of the cells to the same antigen (even if re-exposure occurs in the presence of a costimulatory molecule) results in failure to produce cytokines and subsequently failure to proliferate. Thus, a failure to produce cytokines prevents proliferation. Anergic T cells can, however, proliferate if cultured with cytokines (e.g., IL-2). For example, T cell anergy can also be observed by the lack of IL-2 production by T lymphocytes as measured by ELISA or by a proliferation assay using an indicator cell line. Alternatively, a reporter gene construct can be used. For example, anergic T cells fail to initiate IL-2 gene transcription induced by a heterologous promoter under the control of the 5' IL-2 gene enhancer or by a multimer of the API sequence that can be found within the enhancer (Kang et al. 1992 Science. 257:1134).

As used herein, the term "immunological tolerance" refers to methods performed on a proportion of treated subjects in comparison with untreated subjects where: a) a decreased level of a specific immunological response (thought to be mediated at least in part by antigen-specific effector T lymphocytes, B lymphocytes, antibody, or their equivalents); b) a delay in the onset or progression of a specific immunological response; or c) a reduced risk of the onset or progression of a specific immunological response. "Specific" immunological tolerance occurs when immunological tolerance is preferentially invoked against certain antigens in comparison with others. "Non-Specific" immunological tolerance occurs when immunological tolerance is invoked indiscriminately against antigens which lead to an inflammatory immune response. "Quasi-Specific" immunological tolerance occurs when immunological tolerance is invoked semi-discriminately against antigens which lead to a pathogenic immune response but not to others which lead to a protective immune response.

A proxy for tolerogenic activity is the ability of a particle to stimulate the production of an appropriate cytokine at the target site. The immunoregulatory cytokine released by T suppressor cells at the target site is thought to be TGF-β (Miller et al., Proc. Natl. Acad. Sci. USA 89:421, 1992). Other factors that may be produced during tolerance are the cytokines IL4 and IL-10, and the mediator PGE. In contrast, lymphocytes in tissues undergoing active immune destruction secrete cytokines such as IL-I, IL-2, IL-6, and IFNγ. Hence, the efficacy of a modified particle can be evaluated by measuring its ability to stimulate the appropriate type of cytokines.

With this in mind, a rapid screening test for modified particles, effective mucosal binding components, effective combinations, or effective modes and schedules of mucosal administration can be conducted using animal model systems. Animals are treated at a mucosal surface with the test particle composition, and at some time are challenged with administration of the disease causing antigen or an infectious agent. Spleen cells are isolated, and cultured in vitro in the presence of the disease causing antigen or an antigen derived from the infectious gent at a concentration of about 50 µg/mL. Cytokine secretion into the medium can be quantitated by standard immunoassay.

The ability of the particles to suppress the activity of cells can be determined using cells isolated from an animal immunized with the modified particles, or by creating a cell line responsive to a disease causing antigen or viral antigen target antigen (Ben-Nun et al., Eur. J. Immunol. 11:195, 1981). In one variation of this experiment, the suppressor cell population is mildly irradiated (about 1000 to 1250 rads) to prevent proliferation, the suppressors are co-cultured with the responder cells, and then tritiated thymidine incorporation (or MTT) is used to quantitate the proliferative activity of the responders. In another variation, the suppressor cell population and the responder cell population are cultured in the upper and lower levels of a dual chamber transwell culture system (Costar, Cambridge Mass.), which permits the populations to coincubate within 1 mm of each other, separated by a polycarbonate membrane (WO 93/16724). In this approach, irradiation of the suppressor cell population is unnecessary, since the proliferative activity of the responders can be measured separately.

The effectiveness of compositions and modes of administration for treatment of specific disease can also be elaborated in a corresponding animal disease model. The ability of the treatment to diminish or delay the symptomatology of the disease is monitored at the level of circulating biochemical and immunological hallmarks of the disease, immunohistology of the affected tissue, and gross clinical features as appropriate for the model being employed. Non-limiting examples of animal models that can be used for testing are included in the following section.

The invention contemplates modulation of tolerance by modulating TH1 response, TH2 response, TH17 response, or a combination of these responses. Modulating TH1 response encompasses changing expression of, e.g., interferon-gamma. Modulating TH2 response encompasses changing expression of, e.g., any combination of IL-4, IL-5, IL-10, and IL-13. Typically an increase (decrease) in TH2 response will comprise an increase (decrease) in expression of at least one of IL-4, IL-5, IL-10, or IL-13; more typically an increase (decrease) in TH2 response will comprise an increase in expression of at least two of IL-4, IL-5, IL-10, or EL-13, most typically an increase (decrease) in TH2 response will comprise an increase in at least three of DL-4, IL-5, IL-10, or IL-13, while ideally an increase (decrease) in TH2 response will comprise an increase (decrease) in expression of all of IL-4, IL-5, IL-10, and IL-13. Modulating TH 17 encompasses changing expression of, e.g., TGF-beta, IL-6, IL-21 and IL23, and effects levels of IL-17, IL-21 and IL-22.

Tolerance to autoantigens and autoimmune disease is achieved by a variety of mechanisms including negative selection of self-reactive T cells in the thymus and mechanisms of peripheral tolerance for those autoreactive T cells that escape thymic deletion and are found in the periphery. Examples of mechanisms that provide peripheral T cell tolerance include "ignorance" of self antigens, anergy or unresponsiveness to autoantigen, cytokine immune deviation, and activation-induced cell death of self-reactive T cells. In addition, regulatory T cells have been shown to be involved in mediating peripheral tolerance. See, for example, Walker et al. (2002) Nat. Rev. Immunol. 2: 11-19; Shevach et al. (2001) Immunol. Rev. 182:58-67. In some situations, peripheral tolerance to an autoantigen is lost (or broken) and an autoimmune response ensues. For example, in an animal model for EAE, activation of antigen presenting cells (APCs) through TLR innate immune receptors was shown to break self-tolerance and result in the induction of EAE (Waldner et al. (2004) J. Clin. Invest. 113:990-997). In certain embodiments, the particles of the current invention are able to induce tolerance or general immune regulation by increasing the frequency and/or effector function of Tregs. The Tregs generally upregulated by the particles of the current invention are CD4$^+$CD25$^+$ Tregs that also express the transcriptional repressor factor forkhead box P3 (FoxP3). However, the Tregs that are upregulated by the particles of the current invention may also be CD8$^+$ Tregs or suppressor cells.

Accordingly, in some embodiments, the invention provides methods for increasing antigen presentation while suppressing or reducing TLR7/8, TLR9, and/or TLR 7/8/9 dependent cell stimulation. As described herein, administration of particular modified particles results in antigen presentation by DCs or APCs while suppressing the TLR 7/8, TLR9, and/or TLR7/8/9 dependent cell responses associated with immunostimulatory polynucleotides. Such suppression may include decreased levels of one or more TLR-associated cytokines.

Figure 16A:
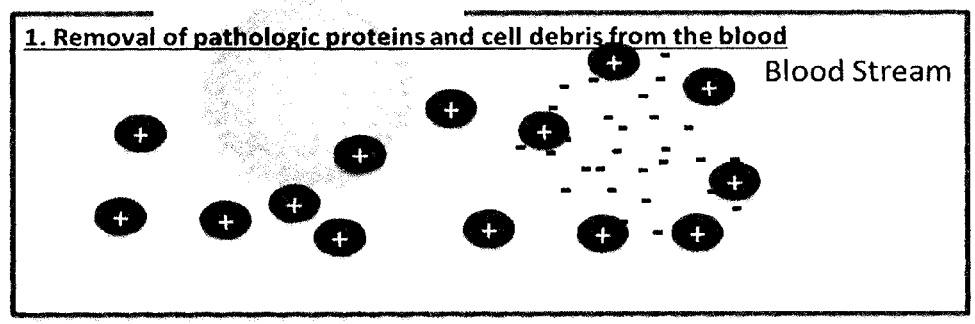
FIG. 16 shows (A) the removal of pathogenic proteins and cellular debris from the blood of a subject with an inflammatory disorder and (B) the concentration and presentation of regulatory proteins from the blood stream of a subject with an inflammatory disorder.
Figure 16B:
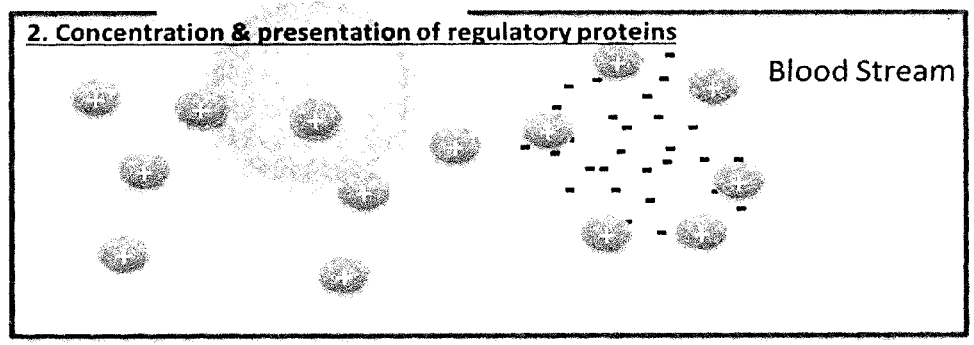

In another aspect of the present invention, negatively charged particles act as sink to mop up pro-inflammatory mediators, pathological proteins and cellular debris from the blood of a subject with an inflammatory response as depicted in FIG. 16A. Alternatively, or in addition to, the negatively charged particles of the present invention may concentrate regulatory proteins by binding to regulatory proteins in the blood of a subject with an inflammatory response and present these regulatory proteins to their cognate receptors to further ameliorate an immune response as depicted in FIG. 16B. As discussed in more detail below, the present inventors have found that at least 15 serum proteins are found bound to negatively charged particles in subjects with an active inflammatory immune response that are not found bound to naïve subjects, or subjects where no immune response is ongoing. This is useful not only in the methods described above, wherein the particles can act as a pro-inflammatory sink or as a concentrator/presentor of immunomodulators, but also in the context of diagnostic methods. Specifically, the negatively charged particles of the current invention may be used in broad scale diagnostic methods of blood samples where other methods, such as mass spectrometry and other proteomic methods have failed. It was surprisingly found that when inflammatory plasma or serum was incubated with the negatively charged particles described herein, this resulted in the binding and subsequent purification of proteins not found in the serum/plasma under non-inflammatory or homeostatic conditions.

In another aspect of the present invention, particles encompassing antigens are provided. Nanoparticles carrying antigen on their surface have been successfully used to induce T-cell tolerance (Getts et al., 2012 Nature Biotechnology 30:1217-1223). Tolerance induced by peptide-coupled particles depends on both the induction of T-cell anergy and the activity of regulatory T cells and may represent an alternative way to treat autoimmune disorders by inducing T-cell tolerance. This T-cell tolerance was observed when using peptides couple to biodegradable (PLG) particles.

In one embodiment, the particles of the invention are coupled to antigens comprising one or more epitopes associated with allergies, autoimmune diseases and/or inflammatory diseases or disorders. The antigens may comprise one or more copies of an epitope. In one embodiment, the antigens comprise a single epitope associated with one disease or disorder. In a further embodiment, the antigens comprise more than one epitope associated with the same disease or disorder. In yet a further embodiment, the antigens comprise more than one epitope associated with different diseases or disorders. In a further embodiment, the antigens comprise one or more epitopes associated with one or more allergies. In a further embodiment, the antigens comprise one or more epitopes associated with multiple sclerosis, type 1 diabetes. Celiac's disease, and/or inflammatory bowel disease, including Crohn's disease or ulcerative colitis.

In one embodiment, the epitopes are from myelin basic protein (e.g. SEQ ID NOs: 4975 & 4976), proteolipid protein (e.g. SEQ ID NO: 4977), myelin oligodendrocyte glycoprotein (e.g. SEQ ID NOs: 1 & 4978), an aquaporin, (e.g. SEQ ID NO: 4979), myelin associated glycoprotein (e.g. SEQ ID NO: 4980), insulin (e.g. SEQ ID NO: 4981), glutamic acid decarboxylase (e.g. SEQ ID NO: 4982), gliadin (e.g. SEQ ID NOs: 4983-4985, or 5136-5140), or the α3 chain of type IV collagen (e.g. SEQ ID NO: 5017), or fragments, homologs, or isoforms thereof. In a further embodiment, the epitopes are from gluten, including from gliadin and/or glutenin. In one embodiment, the epitopes are from insulin homologs, such as those described in U.S. Pat. No. 8,476,228 hereby incorporated in its entirety for all purposes. In one embodiment, the gliaden epitopes are SEQ ID NOs: 13, 14, 16, 320, or 321 in U.S. Application No. 20110293644, or those described in Sollid et al. (2012) Immunogenetics 65:455-460, both hereby incorporated in its entirety for all purposes.

Further non-limiting examples of epitopes associated with various autoimmune diseases and/or inflammatory diseases or disorders that are contemplated by the instant invention are described in Tables 1 and 2.

TABLE 1

Representative Linear Epitopes

| Disease | Representative Epitopes |
| --- | --- |
| Multiple Sclerosis | SEQ ID NOs: 2-1294 |
| Celiac Disease | SEQ ID NOs: 1295-1724; |
|  | SEQ ID NOs: 1726-1766; |
|  | SEQ ID NOs: 4986-5140 |
| Diabetes | SEQ ID NOs: 1767-1840; |
|  | SEQ ID NOs: 1842-1962; |
|  | SEQ ID NOs: 1964-2027; |
|  | SEQ ID NOs: 2029-2073; |
|  | SEQ ID NOs: 2075-2113; |
|  | SEQ ID NOs: 2115-2197; |
|  | SEQ ID NOs: 2199-2248; |
|  | SEQ ID NOs: 2250-2259; |
|  | SEQ ID NOs: 2261-2420; |
|  | SEQ ID NOs: 2422-2486; |
|  | SEQ ID NOs: 2489-2505 |
| Rheumatoid Arthritis | SEQ ID NOs: 2506-3260; |
|  | SEQ ID NOs: 3262-3693 |
| Systemic Lupus Erythematosus | SEQ ID NOs: 3694-3857; |
|  | SEQ ID NOs: 3860-4565 |
| Good Pasture's Syndrome | SEQ ID NOs: 4566-4576; |
|  | SEQ ID NOs: 4578-4610; |
|  | SEQ ID NOs: 4612-4613; |
|  | SEQ ID NOs: 5018-5039 |
| Autoimmune Uveitis | SEQ ID NOs: 4614-4653 |
| Autoimmune Thyroiditis | SEQ ID NOs: 4654-4694; |
|  | SEQ ID NOs: 4696-4894; |
|  | SEQ ID NOs: 4896-4901 |
| Autoimmune Myositis | SEQ ID NOs: 4902-4906 |
| Autoimmune Vasculitis | SEQ ID NOs: 4907-4914 |
| Autoimmune Pancreatitis | SEQ ID NOs: 4915-4917 |
| Crohns Disease | SEQ ID NOs: 4918-4941 |
| Ulcerative Colitis | SEQ ID NOs: 4942-4952 |
| Psoriasis | SEQ ID NOs: 4953-4963 |
| Reactive Arthritis | SEQ ID NOs: 4964-4974 |

Not all epitopes are linear epitopes; epitopes can also be discontinuous, conformational epitopes. A number of discontinuous epitopes associated with autoimmune diseases or inflammatory diseases and/or disorders are known. Non-limiting examples of discontinuous epitopes are described in Table 2.

TABLE 2

Representative Discontinuous Epitopes

| Disease | Epitope | Full Length Polypeptide |
| --- | --- | --- |
| Celiac Disease | D151, E153, E154, E155, E158; | Protein-glutamine gamma-glutamyltransferase 2 |
|  | D306, N308, N310; | SEQ ID NO: 1725 |
|  | D434, E435, E437, D438; |  |
|  | E329; |  |
|  | E153; |  |
|  | R19, E153, M659; or |  |
|  | C277, H335, D358 |  |
| Diabetes | E517; | Glutamate decarboxylase 2 |
|  | R255, F256, K257, K263, | SEQ ID NOs: 1841, 1963, |

TABLE 2-continued

Representative Discontinuous Epitopes

| Disease | Epitope | Full Length Polypeptide |
|---|---|---|
| | E264, K265, L270, P271, R272, L273, L285, K286, K287, I294, G295, T296, D297, S298, R317, R318; N483, I484, I485, K486, N487, R488, E489, G490, Y491, E492, M493, V494, F495, D496, G497, K498, P499, F556, F557, R558, M559, V560, I561, S562, N563, P564, A565, A566, T567, H568, Q569, D570, I571, D572, F573, L574, I575, E576, E577, I578, E579, R580, L581, G582, Q583, D584, L585; E264; E517, E520, E521, S524, S527, V532; E517, E521; K358; R536, Y540 | 2114, & 2249 |
| Diabetes | P876, A877, E878, T880; T804; T804, V813, D821, R822, Q862, P886; T804, V813, D821, R822, Q862, P886; W799, E836, N858; D911; Q862; L831, H833, V834, E836, Q860; W799, E836, N858; W799, L831, H833, V834, Y835, E836, Q860; | protein tyrosine phosphatase, receptor type, N precursor SEQ ID NOs: 2028 & 2074 |
| Diabetes | R325, R332, E333, K336, K340; R325; W325 | zinc transporter 8 isoform a SEQ ID NO: 2421 |
| Diabetes | E872, C945 | Receptor-type tyrosine-protein phosphatase N2 SEQ ID NOs: 2198, 2260, & 2487 |
| Diabetes | W799, C909 | tyrosine phosphatase SEQ ID NO: 2488 |
| Rheumatoid Arthritis | L14, M15, I16, S17, R18, N147, G148, S187, M191, H196, N197, H198, Y199, Q201, S203 | Chain A, Crystal Structure Of A Human Igm Rheumatoid Factor Fab In Complex With Its Autoantigen Igg Fc SEQ ID NO: 3261 |
| Systemic Lupus Erythematosus | K591, S592, G593 | ATP-dependent DNA helicase 2 subunit 1 SEQ ID NO: 3858 |
| Systemic Lupus Erythematosus | M1, K2, L3, V4, R5, F6, L7, M8, K9, L10, S11, H12, E13, T14, V15, T16, I17, E18, L19, K20, N21, G22, T23, Q24, V25, H26, P85, K86, V87, K88, S89, K90, K91, R92, E93, A94, V95, A96, G97, R98, G99, R100, G101, R102, G103, R104, G105, R106, G107, R108, G109, R110, G111, R112, G113, R114, G115, G116, P117, R118, R119 | Small nuclear ribonucleoprotein Sm D1 SEQ ID NO: 3859 |
| Systemic Lupus Erythematosus | G59, R62 | beta-2-glycoprotein I SEQ ID NO: 4357 |
| Good Pasture's Syndrome | T24, A25, I26, S28, E31, V34, P35, S38, Q64 | type IV collagen alpha3 chain SEQ ID NO: 4577 |
| Good Pasture's Syndrome | T1455, A1456, I1457, S1459, E1462, T1464, V1465, P1466, Y1468, S1469, Q1495, T1537, T1565, P1569, H1572, K1579, A1634 | alpha3 type IV collagen SEQ ID NO: 4611 |
| Autoimmune Thyroiditis | E604, D620, K627, D630; R225, R646, D707; K627; | Thyroid peroxidase SEQ ID NO: 4695 |

TABLE 2-continued

Representative Discontinuous Epitopes

| Disease | Epitope | Full Length Polypeptide |
| --- | --- | --- |
| Autoimmune Thyroiditis | R225;<br>Y772;<br>K713, F714, P715, E716;<br>P715, D717<br>D36, R38, K42, Q55, K58, I60,<br>E61, R80, Y82, S84, T104,<br>H105, E107, R109, N110, K129,<br>F130, D151, F153, I155, E157,<br>T181, K183, D203 | Thyrotropin receptor<br>SEQ ID NO: 4895 |

In another aspect of the present invention, particles encapsulating antigens are provided. Particles which encapsulate antigens inside the particle can be used to induce T-cell tolerance in a subject. Examples of antigens which can be encapsulated within the particles of the invention include, but are not limited to, exogenous antigens, such as viral and bacterial antigens, endogenous antigens, autoantigens, tumor antigens, and/or native antigens.

Monocytes and macrophages play central roles in the initiation and resolution of inflammation, principally through phagocytosis, the release of inflammatory cytokines, reactive oxygen species and the activation of the acquired immune system (Auffray et al., 2009 Annu Rev Immunol 27:669-692). Typically, monocytes circulate in the bloodstream for a very short time before undergoing apoptosis, however, stimulatory signals can trigger monocyte survival by inhibiting the apoptotic pathway, and thus contribute to the maintenance of the inflammatory response. Anti-apoptotic proteins work by inhibiting caspases or the activation of the apoptotic program. Phosphatidyl inositol 3-kinase (PI-3K)/Akt, ERK, Fas, TNF, heat shock proteins and anti-apoptotic molecules, among others, play key roles in determining monocyte life span. During the inflammatory response, inflammatory cells, such as monocytes and macrophages, are recruited to the sites of inflammation. This recruitment is essential for effective control and clearance of infection, but recruited monocytes also contribute to the pathogenesis of inflammatory and degenerative diseases. The accumulation of monocytes can be harmful and aggravate disease such as atherosclerosis, arthritis, and multiple sclerosis. Resolution of inflammation requires the reduction and/or inhibition of inflammatory cells to the inflammatory foci, and apoptosis of the inflammatory cells already present. Apoptotic caspases play a fundamental role by proteolytically dismantling cells by degrading proteins with diverse biological functions. For instance, caspase-3 activation is essential for $CD14^+$ monocyte apoptosis (Fahy et al., 1999 J. Immunol. 163:1755-1762).

The negatively charged particles of the present invention (sometimes referred to herein as "immune modified particles" or "IMPs") specifically inhibit inflammatory monocyte immigration into inflammatory foci. Inflammatory monocytes take up IMPs in a macrophage receptor with collagenous (MARCO) dependent fashion and migrate to the spleen, whereby they undergo caspase 3-mediated cell death. Importantly IMP therapy is shown to have positive impacts on West Nile Virus (WNV) encephalitis, peritonitis, experimental autoimmune encephalomyelitis, heart function after myocardial infarction, kidney reperfusion injury and colitis. IMPs provide an alternative and highly specific tool for inhibiting inflammatory monocytes in a MARCO-dependent manner. Harnessing a natural leukocyte clearance pathway, IMPs represent a novel and safe inflammatory monocyte specific therapy.

In one aspect, the methods of the current invention include inducing apoptosis in monocytes, granulocytes and/or neutrophils in a subject to reduce the severity or duration of an inflammatory response. In one embodiment, administering the negatively charged particles of the invention induces monocyte, granulocyte and/or neutrophil apoptosis and clearance, thereby aiding in the resolution of inflammation.

In one aspect, the methods of the current invention contemplate using the particles of the invention as "molecular sinks" that bind to inflammatory molecules and polypeptides produced by the cell, thereby preventing them from exerting their activity. When inflammation happens, pro-inflammatory mediators such as cytokines and chemokines are released by cells, such as macrophages and monocytes, into the surrounding pro-inflammatory milieu. Examples of pro-inflammatory mediators include, but are not limited to interleukins, members of the TNF family, interferons, and colony stimulating factors. These mediators potentiate the inflammatory response, thereby exacerbating the inflammatory pathology. As described herein, the particles of the invention bind to inflammatory mediators in the serum of animals experiencing an inflammatory immune response. The inflammatory mediators to which the particles of the invention bind include, but are not limited to, heat shock protein beta-1, protein S100-A7, protein S100-A8, protein S100-A9, fatty acid-binding protein, annexin A1 and ubiquitin cross-reactive protein precursor. Administration of uncoated particles of the invention to animals results in a decrease of inflammatory monocytes present in the inflammatory foci, a decrease in inflammatory symptoms, and an increase in survival of infected animals.

As discussed above, this invention provides novel compounds that have biological properties useful for the treatment of immune mediated disorders.

Accordingly, in another aspect of the present invention, pharmaceutical compositions are provided, which comprise the particles and optionally comprise a pharmaceutically acceptable carrier. In certain embodiments, these compositions optionally further comprise one or more additional therapeutic agents. In another embodiment, the particles of the invention may encapsulate an antigen or be embedded with an antigen. Alternatively, the particles of the current invention may be administered to a patient in need thereof in combination with the administration of one or more other therapeutic agents. For example, additional therapeutic agents for conjoint administration or inclusion in a pharmaceutical composition with a compound of this invention may be an approved anti-inflammatory agent, or it may be any one of a number of agents undergoing approval in the Food and Drug Administration that ultimately obtain approval for the treatment of any disorder characterized by an uncontrolled inflammatory immune response or a bacterial or viral infection. It will also be appreciated that certain of the modified particles of present invention can exist in free form for treatment, or where appropriate, as a pharmaceutically acceptable derivative thereof.

The pharmaceutical compositions of the present invention additionally comprise a pharmaceutically acceptable carrier, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutical compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutical composition, its use is contemplated to be within the scope of this invention. Some examples of materials which can serve as pharmaceutically acceptable carriers include, but are not limited to, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatine; talc; excipients such as cocoa butter and suppository waxes; oils such as peanut oil, cottonseed oil; safflower oil, sesame oil; olive oil; corn oil and soybean oil; glycols; such as propylene glycol; esters such as ethyl oleate and ethyl laurate; agar; buffering agents such as magnesium hydroxide and aluminum hydroxide; alginic acid; pyrogenfree water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension or crystalline or amorphous material with poor water solubility. The rate of absorption of the drug then depends upon its rate of dissolution that, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include (poly(orthoesters) and poly(anhydrides). Depot injectable formulations are also prepared by entrapping the drug in liposomes or microemulsions which are compatible with body tissues. In certain embodiments, drugs and therapeutics may be encapsulated in the particles of the invention for administration to the subject.

Solid dosage forms for oral administration include capsules, tablets, pills, powders, and granules. In such solid dosage forms, the modified particles are mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The modified particles can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose and starch. Such dosage forms may also comprise, as in normal practice, additional substances other than inert diluents, e.g., tableting lubricants and other tableting aids such as magnesium stearate and microcrystalline cellulose. In the case of capsules, tablets and pills, the dosage forms may also comprise buffering agents. They may optionally contain opacifying agents and can also be of a composition that they release the modified particles only, or preferentially, in a certain part of the intestinal tract, optionally, in a delayed manner. Examples of embedding compositions which can be used include polymeric substances and waxes.

The present invention encompasses pharmaceutically acceptable topical formulations of the inventive modified particles. The term "pharmaceutically acceptable topical formulation", as used herein, means any formulation which is pharmaceutically acceptable for intradermal administration of modified particles of the invention by application of the formulation to the epidermis. In certain embodiments of the invention, the topical formulation comprises a carrier system. Pharmaceutically effective carriers include, but are not limited to, solvents (e.g., alcohols, poly alcohols, water), creams, lotions, ointments, oils, plasters, liposomes, powders, emulsions, microemulsions, and buffered solutions (e.g., hypotonic or buffered saline) or any other carrier known in the art for topically administering pharmaceuticals. A more complete listing of art-known carriers is provided by reference texts that are standard in the art, for example, Remington's Pharmaceutical Sciences, 16th Edition, 1980 and 17th Edition, 1985, both published by Mack Publishing Company, Easton, Pa., the disclosures of which are incorporated herein by reference in their entireties. In certain other embodiments, the topical formulations of the invention may comprise excipients. Any pharmaceutically acceptable excipient known in the art may be used to prepare the inventive pharmaceutically acceptable topical formulations. Examples of excipients that can be included in the topical formulations of the invention include, but are not limited to, preservatives, antioxidants, moisturizers, emollients, buffering agents, solubilizing agents, other penetration agents, skin protectants, surfactants, and propellants, and/or additional therapeutic agents used in combination to the modified particles. Suitable preservatives include, but are not limited to, alcohols, quaternary amines, organic acids, parabens, and phenols. Suitable antioxidants include, but are not limited to, ascorbic acid and its esters, sodium bisulfite, butylated hydroxytoluene, butylated hydroxyanisole, tocopherols, and chelating agents like EDTA and citric acid. Suitable moisturizers include, but are not limited to, glycerine, sorbitol, polyethylene glycols, urea, and propylene glycol. Suitable buffering agents for use with the invention include, but are not limited to, citric, hydrochloric, and lactic acid buffers. Suitable solubilizing agents include, but are not limited to, quaternary ammonium chlorides, cyclodextrins, benzyl benzoate, lecithin, and polysorbates. Suitable skin protectants that can be used in the topical formulations of the invention include, but are not limited to, vitamin E oil, allatoin, dimethicone, glycerin, petrolatum, and zinc oxide.

In certain embodiments, the pharmaceutically acceptable topical formulations of the invention comprise at least the modified particles of the invention and a penetration enhancing agent. The choice of topical formulation will depend or several factors, including the condition to be treated, the physicochemical characteristics of the inventive compound and other excipients present, their stability in the formulation, available manufacturing equipment, and costs constraints. As used herein the term "penetration enhancing agent" means an agent capable of transporting a pharmacologically active compound through the stratum corneum and into the epidermis or dermis, preferably, with little or no systemic absorption. A wide variety of compounds have been evaluated as to their effectiveness in enhancing the rate of penetration of drugs through the skin. See, for example, Percutaneous Penetration Enhancers, Maibach H. I. and Smith H. E. (eds.), CRC Press, Inc., Boca Raton, Fla. (1995), which surveys the use and testing of various skin penetration enhancers, and Buyuktimkin et al., Chemical Means of Transdermal Drug Permeation Enhancement in Transdermal and Topical Drug Delivery Systems, Gosh T. K., Pfister W. R., Yum S. I. (Eds.), Interpharm Press Inc., Buffalo Grove, Ill. (1997). In certain exemplary embodiments, penetration agents for use with the invention include, but are not limited to, triglycerides (e.g., soybean oil), aloe compositions (e.g., aloe-vera gel), ethyl alcohol, isopropyl alcohol, octolyphenylpolyethylene glycol, oleic acid, polyethylene glycol 400, propylene glycol, N-decylmethylsulfoxide, fatty acid esters (e.g., isopropyl myristate, methyl laurate, glycerol monooleate, and propylene glycol monooleate) and N-methylpyrrolidone.

In certain embodiments, the compositions may be in the form of ointments, pastes, creams, lotions, gels, powders, solutions, sprays, inhalants or patches. In certain exemplary embodiments, formulations of the compositions according to the invention are creams, which may further contain saturated or unsaturated fatty acids such as stearic acid, palmitic acid, oleic acid, palmito-oleic acid, cetyl or oleyl alcohols, stearic acid being particularly preferred. Creams of the invention may also contain a non-ionic surfactant, for example, polyoxy-40-stearate. In certain embodiments, the active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms are made by dissolving or dispensing the compound in the proper medium. As discussed above, penetration enhancing agents can also be used to increase the flux of the compound across the skin. The rate can be controlled by either providing a rate controlling membrane or by dispersing the compound in a polymer matrix or gel.

The modified particles can be administered by aerosol. This is accomplished by preparing an aqueous aerosol, liposomal preparation or solid particles containing the modified particles. A nonaqueous (e.g., fluorocarbon propellant) suspension could be used.

Ordinarily, an aqueous aerosol is made by formulating an aqueous solution or suspension of the agent together with conventional pharmaceutically acceptable carriers and stabilizers. The carriers and stabilizers vary with the requirements of the particular compound, but typically include nonionic surfactants (Tweens, Pluronics®, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

It will also be appreciated that the modified particles and pharmaceutical compositions of the present invention can be formulated and employed in combination therapies, that is, the compounds and pharmaceutical compositions can be formulated with or administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another anti-inflammatory agent), or they may achieve different effects (e.g., control of any adverse effects).

In certain embodiments, the pharmaceutical compositions containing the modified particles of the present invention further comprise one or more additional therapeutically active ingredients (e.g., anti-inflammatory and/or palliative). For purposes of the invention, the term "Palliative" refers to treatment that is focused on the relief of symptoms of a disease and/or side effects of a therapeutic regimen, but is not curative. For example, palliative treatment encompasses painkillers, antinausea medications and anti-sickness drugs.

The invention provides methods of regulating an immune response in an individual, preferably a mammal, more preferably a human, comprising administering to the individual the modified particles described herein. Methods of immunoregulation provided by the invention include those that suppress and/or inhibit an innate immune response or an adaptive immune response, including, but not limited to, an immune response stimulated by immunostimulatory polypeptides or viral or bacterial components.

The modified particles are administered in an amount sufficient to regulate an immune response. As described herein, regulation of an immune response may be humoral and/or cellular, and is measured using standard techniques in the art and as described herein.

In certain embodiments, the individual suffers from a disorder associated with unwanted immune activation, such as allergic disease or condition, allergy and asthma. An individual having an allergic disease or asthma is an individual with a recognizable symptom of an existing allergic disease or asthma.

In certain embodiments, the individual suffers from a disorder associated with unwanted immune activation, such as autoimmune disease and inflammatory disease. An individual having an autoimmune disease or inflammatory disease is an individual with a recognizable symptom of an existing autoimmune disease or inflammatory disease.

Autoimmune diseases can be divided in two broad categories: organ-specific and systemic. Autoimmune diseases include, without limitation, rheumatoid arthritis (RA), systemic lupus erythematosus (SLE), type I diabetes mellitus, type II diabetes mellitus, multiple sclerosis (MS), immune-mediated infertility such as premature ovarian failure, scleroderma, Sjogren's disease, vitiligo, alopecia (baldness), polyglandular failure, Grave's disease, hypothyroidism, polymyositis, pemphigus vulgaris, pemphigus foliaceus, inflammatory bowel disease including Crohn's disease and ulcerative colitis, Celiac disease, autoimmune hepatitis including that associated with hepatitis B virus (HBV) and hepatitis C virus (HCV), hypopituitarism, graft-versus-host disease (GvHD), myocarditis, Addison's disease, autoimmune skin diseases, uveitis, pernicious anemia, and hypoparathyroidism.

Autoimmune diseases may also include, without limitation, Amyotrophic Lateral Sclerosis (ALS), Hashimoto's thyroiditis, Type I and Type II autoimmune polyglandular syndromes, paraneoplastic pemphigus, bullus pemphigoid, dermatitis herpetiformis, linear IgA disease, epidermolysis bullosa acquisita, erythema nodosa, pemphigoid gestationis, cicatricial pemphigoid, mixed essential cryoglobulinemia, chronic bullous disease of childhood, hemolytic anemia, thrombocytopenic purpura, Goodpasture's syndrome, autoimmune neutropenia, myasthenia gravis, Eaton-Lambert myasthenic syndrome, stiff-man syndrome, acute disseminated encephalomyelitis, Guillain-Barre syndrome, chronic inflammatory demyelinating polyradiculoneuropathy, multifocal motor neuropathy with conduction block, chronic neuropathy with monoclonal gammopathy, opsonoclonus-myoclonus syndrome, cerebellar degeneration, encephalomyelitis, retinopathy, primary biliary sclerosis, sclerosing cholangitis, gluten-sensitive enteropathy, ankylosing spondylitis, reactive arthritis, polymyositis/dermatomyositis, mixed connective tissue disease, Bechet's syndrome, psoriasis, polyarteritis nodosa, allergic anguitis and granulomatosis (Churg-Strauss disease), polyangiitis overlap syndrome, hypersensitivity vasculitis, Wegener's granulomatosis, temporal arteritis, Takayasu's arteritis, Kawasaki's disease, isolated vasculitis of the central nervous system, thromboangiutis obliterans, sarcoidosis, glomerulonephritis, and cryopathies. These conditions are well known in the medical arts and are described, for example, in Harrison's Principles of Internal Medicine, 14th ed., Fauci A S et al., eds., New York: McGraw-Hill, 1998.

Subjects treated by the particles of the present invention are preferably human, however, the particles are useful in treating non-human animal species. Non-human animal species which may be treated by the particles of the present invention include, but are not limited to, dogs, cats, chickens, geese, ducks, sheep, cows, goats, pigs, non-human primates, monkey, rabbits, mice, rats, guinea pigs, hamsters, gerbils, and horses.

Animal models for the study of autoimmune disease are known in the art. For example, animal models which appear most similar to human autoimmune disease include animal strains which spontaneously develop a high incidence of the particular disease. Examples of such models include, but are not limited to, the non-obese diabetic (NOD) mouse, which develops a disease similar to type 1 diabetes, and lupus-like disease prone animals, such as New Zealand hybrid, MRL-Fas$^{lpr}$ and BXSB mice. Animal models in which an autoimmune disease has been induced include, but are not limited to, experimental autoimmune encephalomyelitis (EAE), which is a model for multiple sclerosis, collagen-induced arthritis (CIA), which is a model for rheumatoid arthritis, and experimental autoimmune uveitis (EAU), which is a model for uveitis. Animal models for autoimmune disease have also been created by genetic manipulation and include, for example, IL-2/IL-10 knockout mice for inflammatory bowel disease, Fas or Fas ligand knockout for SLE, and IL-I receptor antagonist knockout for rheumatoid arthritis.

In certain embodiments, the individual suffers from a bacterial or viral infection. An individual having a bacterial or viral infection is an individual with a recognizable symptom of an existing bacterial or viral infection.

A non-limiting list of viral infections treatable with the modified particles of the current invention includes herpes virus infections, hepatitis virus infections, west nile virus infections, flavivrus infections, influenza virus infections, rhinovirus infections, papillomavirus infections, paromyxovirus infections, parainfluenza virus infections, and retrovirus infections. Preferred viruses are those viruses that infect the central nervous system of the subject. Most preferred viruses are those that cause encephalitis or meningitis.

A non-limiting list of bacterial infections treatable with the modified particles of the current invention include *staphylococcus* infections, *streptococcus* infections, mycobacterial infections, *bacillus* infections, *Salmonella* infections, *Vibrio* infections, spirochete infections, and *Neisseria* infections. Preferred are bacteria that infect the central nervous system of the subject. Most preferred are bacteria that cause encephalitis or meningitis.

In some embodiments, the invention relates to uses of compositions of this invention prior to the onset of disease. In other embodiments, the invention relates to uses of the compositions of this invention to inhibit ongoing disease. In some embodiments, the invention relates to ameliorating disease in a subject. By ameliorating disease in a subject is meant to include treating, preventing or suppressing the disease in the subject.

In some embodiments, the invention relates to preventing the relapse of disease. For example, an unwanted immune response can occur at one region of a peptide (such as an antigenic determinant). Relapse of a disease associated with an unwanted immune response can occur by having an immune response attack at a different region of the peptide. Since the negatively charged particles of the current invention are free from attached peptides or antigenic moieties, the particles will be effective against multiple epitopes. T-cell responses in some immune response disorders, including MS and other ThI/17-mediated autoimmune diseases, can be dynamic and evolve during the course of relapsing-remitting and/or chronic-progressive disease. The dynamic nature of the T-cell repertoire has implications for treatment of certain diseases, since the target may change as the disease progresses. Previously, pre-existing knowledge of the pattern of responses was necessary to predict the progression of disease. The present invention provides compositions that can prevent the effect of dynamic changing disease, a function of "epitope spreading." A known model for relapse is an immune reaction to proteolipid protein (PLP) as a model for multiple sclerosis (MS). Initial immune response can occur by a response to PLP139-15. Subsequent disease onset can occur by a relapse immune response to PLP[pi]s-iβi.

Certain embodiments of this invention relate to treatment of pathological conditions relating to an unwanted hypersensitivity. The hypersensitivity can be any one of types I, II, III, and IV. Immediate (type I) hypersensitivity. The frequency of administration will typically correspond with the timing of allergen exposure. Suitable animal models are known in the art (for example, Gundel et al., Am. Rev. Respir. Dis. 146:369, 1992, Wada et al., J. Med. Chem. 39, 2055, 1996; and WO 96/35418).

Other embodiments of this invention relate to transplantation. This refers to the transfer of a tissue sample or graft from a donor individual to a recipient individual, and is frequently performed on human recipients who need the tissue in order to restore a physiological function provided by the tissue. Tissues that are transplanted include (but are not limited to) whole organs such as kidney, liver, heart, lung; organ components such as skin grafts and the cornea of the eye; and cell suspensions such as bone marrow cells and cultures of cells selected and expanded from bone marrow or circulating blood, and whole blood transfusions.

A serious potential complication of any transplantation ensues from antigenic differences between the host recipient and the engrafted tissue. Depending on the nature and degree of the difference, there may be a risk of an immunological assault of the graft by the host, or of the host by the graft, or both, may occur. The extent of the risk is determined by following the response pattern in a population of similarly treated subjects with a similar phenotype, and correlating the various possible contributing factors according to well accepted clinical procedures. The immunological assault may be the result of a preexisting immunological response (such as preformed antibody), or one that is initiated about the time of transplantation (such as the generation of TH cells). Antibody, TH cells, or Tc cells may be involved in any combination with each other and with various effector molecules and cells. However, the antigens which are involved in the immune response are generally not known, therefore posing difficulties in designing antigen-specific therapies or inducing antigen-specific tolerance. The modified particles of the current invention are particularly useful in preventing the rejection of organs because no attached peptides or antigens need to be conjugated to the modified particles in order for the particles to be effective in inducing tolerance or ameliorate an inflammatory immune response.

Certain embodiments of the invention relate to decreasing the risk of host versus graft disease, leading to rejection of the tissue graft by the recipient. The treatment may be performed to prevent or reduce the effect of a hyperacute, acute, or chronic rejection response. Treatment is preferentially initiated sufficiently far in advance of the transplant so that tolerance will be in place when the graft is installed; but where this is not possible, treatment can be initiated simultaneously with or following the transplant. Regardless of the time of initiation, treatment will generally continue at regular intervals for at least the first month following transplant. Follow-up doses may not be required if a sufficient accommodation of the graft occurs, but can be resumed if there is any evidence of rejection or inflammation of the graft. Of course, the tolerization procedures of this invention may be combined with other forms of immunosuppression to achieve an even lower level of risk.

Certain embodiments of the invention relate to decreasing or otherwise ameliorating the inflammatory response induced as a response to surgery. In one embodiment of the invention, the immune-modifying particles are administered before surgery. In a further embodiment of the invention, the immune-modifying particles are administered concurrently with or during surgery. In yet a further embodiment of the invention, the immune-modifying particles are administered after surgery.

The particles of the invention may also be used to treat abscesses or empyemas to decrease the inflammatory response produced in the subject after exposure to infectious agents such as bacteria or parasites. In one embodiment of the invention, the immune-modifying particles are administered in conjunction with anti-bacterial and/or anti-parasitic treatments known in the art.

The particles of the invention may also be used to decrease or otherwise ameliorate the inflammatory response induced as a response to physical trauma or injury including, but not limited to, a sports injury, a wound, a spinal cord injury, a brain injury, and/or a soft tissue injury. In one embodiment of the invention, the immune-modifying particles are administered after the subject experiences trauma or injury.

The particles of the invention may also be used to decrease the inflammatory response associated with the development and/or growth of cancer cells. Cancers that can be treated include, but are not limited to, central nervous system cancer, basal cell carcinoma, cancerous brain tumors, Burkitt's lymphoma, lymphoma, cervical cancer, ovarian cancer, testicular cancer, liver cancer, non-small cell and small cell lung cancers, melanoma, bladder cancer, breast cancer, colon and rectal cancers, endometrial cancer, kidney (renal cell) cancer, leukemia, Non-Hodgkin lymphoma, pancreatic cancer, prostate cancer, and thyroid cancer. In one embodiment, the subcutaneous injection of the particles of the invention prevents the accumulation of inhibitory neutrophils or monocyte derived suppressor cells, thereby enhancing or facilitating the tumor-specific immune response the cancer patient.

The particles of the invention are also useful for the regeneration of damaged tissue. In one embodiment, administration of the particles to a patient increases the regeneration of damaged epithelial cells in the digestive tract. In a further embodiment, the patient suffers from ulcerative colitis, Crohn's disease, or inflammatory bowel disease. In another embodiment, administration of the particles of the invention to a patient increases remyelination of neurons. In a further embodiment, the patient suffers from multiple sclerosis.

EXAMPLES

The following examples are provided to further illustrate the advantages and features of the invention, but are not intended to limit the scope of this disclosure.

Materials and Methods

Mice

For WNV and IBD studies, eight-week old female C57BL/6 mice were obtained from the Animal Resources Centre (WA, Australia). All procedures were performed with permission of the University of Sydney Animal Ethics Committee. For EAE studies, eight-week old female SJL/J mice were obtained from Harlan Laboratories (Indianapolis, Ind., USA). For thioglycollate studies, eight-week old female Balb/c were obtained from the National Cancer Institute (MD, USA). MARCO−/− animals on the Balb/c background were kindly provided by Lester Kobzik (Harvard University, MA, USA). For cardiac inflammation studies, twelve-week old male C57BL/6 mice were purchased from the Jackson Laboratory (ME, USA). All procedures were performed with permission of the Northwestern University Institutional Animal Care and Use Committee. All animals were housed under specific pathogen-free conditions with food and water provided ad libitum.

WNV Infection

WNV (Sarafend) was derived from the brains of neonatal mice and propagated in vitro cell cultures (Getts et al., J. Exp Med. 205:2319-2337, 2008). WNV infection was conducted in C57BL/6 animals (Getts et al., J. Exp Med. 205:2319-2337, 2008). Mice were intranasally infected with 6×104 or 6×103 PFU WNV in 10 μL sterile Phosphate buffered saline (PBS; Invitrogen, CA, USA). Mock 24 infections were conducted using sterile PBS only. Following infection, mice were weighed daily.

Thioglycollate-Induced Peritonitis

The induction of peritonitis was performed intraperitoneal injection of 1 ml of a 4% (w/v) Thioglycollate broth prepared in sterile water (Sigma Aldrich, MO, USA). Leukocytes were isolated at defined time points by intraperitoneal lavage (wash) using ice cold 0.05 mM EDTA PBS solution.

EAE Induction

PLP139-151 (HSLGKWLGHPDKF) peptide-induced EAE was induced in SJL/J mice (Getts et al., J. Immunol. 187:2405-2417, 2011). Individual animals were observed daily and clinical scores were assessed in a blinded fashion on a 0-5 scale as follows: 0=no abnormality; 1=limp tail or hind limb weakness; 2=limp tail and hind limb weakness; 3=hind limb paralysis; 4=hind limp paralysis and forelimb weakness; and 5=moribund. These data are reported as the mean clinical score. Paralysed animals were afforded easier access to food and water.

Cardiac Infarction

Myocardial infarction was conducted in C57BL/6 mice. The left anterior descending artery was permanently occluded surgically (Yeap et al., Methods in Molecular Biology, In Press).

Kidney Ischemia Reperfusion Induction

The renal artery was ligated for 45 minutes and then released to allow complete reperfusion of the kidney.

Inflammatory Bowel Disease Induction

The DSS-induced colitis model of IBD was induced (Bao et al., Immunol. Cell Bio. 89:853-860, 2011). Dextran sulphate sodium (DSS, MW 36,000-44,000 D; ICN Biomedicals, Australasia) 2.5% w/v 25 dissolved in tap water was administered ad libitum for 9 consecutive days 41. Control groups received tap water only during this time. Bodyweight and clinical assessments were measured daily. Percentage bodyweight loss was calculated as follows: (mean weight at (day 0-9)/weight on day 0)×100. Following bodyweight measurements, mice were examined for clinical parameters, including mobility and gait, vocalizations, group interactions & grooming. Each parameter was scored a value between 0-2, where a total value of 0-1 represents normal, 2-4 mild, 5-7 moderate, 8-10 severe 41. Faecal assessment was measured daily where possible. Scores were given for faecal consistency, hematochezia, and rectal bleeding. A total value between 0-6 reflected the faecal score, where a value of 0 represents faeces of normal appearance and a value of 6 represents severe diarrhoea, rectal bleeding and presence of blood in stools.

Intravenous Delivery of Particles

FITC or Bright Blue (BB) Flouresbrite plain and carboxylated polystyrene particles (0.5 μm diameter) were obtained from Polysciences (PA, USA). FITC Poly(lactic-coglycolic acid) (PLGA) and FITC polystyrene plain, carboxylated and aminated particles (500 nm diameter) were obtained from Phosphorex (MA, USA). Carboxylated 500 nm nanodiamonds were generated at Macquarie University or Sydney University (NSW, Australia). Particles were diluted to the indicated concentration in sterile PBS and 200 μL was injected i.v. as indicated. Vehicle control animals received 200 μL sterile PBS only. Tissues were harvested at the designated time points and process for flow cytometry, histology, or immunohistochemistry. Isolation and sorting of bone marrow-derived Ly6C$^{hi}$ inflammatory monocytes was performed as described in Getts et al., 2008, with isolated cells labeled with PKH26 (Invitrogen) and 2.0×10$^6$ cells injected i.v. into mock- and WNV-infected recipients on D6 p.i. Specific particle properties are defined in Table 3.

Flow Cytometry

Mice were anesthetized and perfused with 50 mL sterile PBS. Spleen, brain, bone marrow, blood and peritoneal fluid was isolated and processed into single cell suspensions (Getts et al., J. Exp Med. 205:2319-2337, 2008). Cells were incubated with anti-CD16/32 and live cells were counted using trypan blue exclusion, which routinely showed >95% viability. Cells were then incubated with fluorescently-labelled antibodies against CD45, CD11b, Ly6C, Ly6G, CD11c, CD103, ETC (Biolegend). Cell surface molecule expression was measured on a FACS LSR-II using FACS Diva program (Becton Dickinson, NJ, USA). Viable populations were gated by forward- and side-scatter and identified fluorescent populations determined by forward-gating thereafter. Acquired FACS data files were analyzed using the flow cytometry program Flow Jo (Tree Star, Inc. OR, USA). Quantification of cell populations of interest were calculated based on flow cytometry percentages at analysis and absolute cell counts from each organ.

Adoptive Transfer

The bone marrow of WNV-infected animals was processed into single cell suspensions on D6 p.i. and incubated with fluorescently-labelled antibodies against CD11b, Ly6C and Ly6G. CD11b+, Ly6Chi, Ly6G− monocytes were sorted on a FACS Aria using the FACS Diva program (Becton Dickinson), with stringencies set to achieve >98% purity. Cells were then labeled with the fluorescent membrane dye PKH26 (Invitrogen) according to the manufacturer's instructions. Matched mock-infected and WNV-infected recipients were i.v. injected with 2.0×106 sorted Ly6Chi monocytes on D6 p.i., delivered in 200 μL PBS. Brain and spleens were isolated from recipients on D7 p.i. (24 h post-transfer) and processed for flow cytometry, as described above.

Histology and Immunohistochemistry

Mice were anesthetized and perfused with 50 mL sterile PBS. With the exception of the heart, which were processed into paraffin blocks (Getts et al., J. Neurochem 103:10919-1030, 2007), all organs were isolated and snap frozen in Optimum Cutting Temperature Compound (OCT; Tissue-Tek, Tokyo, Japan). Eight-micron tissue sections were cut on a cryostat microtome, air-dried overnight and then stored at −80° C. until required. Frozen sections were thawed and histology (standard haematoxylin and eosin staining) or immunohistochemistry was performed (Getts et al., J. Exp Med 205:2319-2337, 2008). Antibodies against MARCO, SIGN-R1 and SIGLEC-1 (R&D Systems, MN, USA), CD68 (Abcam, MA, USA) and Ki67 (Abcam), were used as indicated. Images were acquired on an Olympus BX-51 microscope using a DP-70 camera and DP manager 2.2.1 software (Olympus, Tokyo, Japan).

Histology and Immunohistochemistry

Mice were anesthetized and perfused with 50 mL sterile PBS. With the exception of the heart, which were processed into paraffin blocks (Getts et al., J. Neurochem 103:10919-1030, 2007), all organs were isolated and snap frozen in Optimum Cutting Temperature Compound (OCT; Tissue-Tek, Tokyo, Japan). Eight-micron tissue sections were cut on a cryostat microtome, air-dried overnight and then stored at −80° C. until required. Frozen sections were thawed and histology (standard haematoxylin and eosin staining) or immunohistochemistry was performed (Getts et al., J. Exp Med 205:2319-2337, 2008). Antibodies against MARCO, SIGN-R1 and SIGLEC-1 (R&D Systems, MN, USA), CD68 (Abcam, MA, USA) and Ki67 (Abcam), were used as indicated. Images were acquired on an Olympus BX-51 microscope using a DP-70 camera and DP manager 2.2.1 software (Olympus, Tokyo, Japan).

Multiplex ELISA

Multiplex plate ELISA (Quansys Biosciences) was performed using the Quansys Q-plex Mouse Cytokine Screen IR 16-plex according to the manufacturer's instructions. Plates were visualized on the Li-Cor Odyssey IR Imaging System (Li-Cor Biotechnology). Images were analysed using Quansys Q-view software (Quansys Biosciences).

TABLE 3

Physical Properties of the Particles
Physical Properties

| | Immune Modified (Carboxylated) Polystyrene Particles (Phosphorex) | Polystyrene Neutral Particles (Phosphorex) | Polystyrene Positive Charged (Aminated Particles-Phosphorex) | Immune Modified Nano-Diamonds (University of Sydney) | Immune Modified (Carboxylated) PLGA Particles (Phosphorex) |
|---|---|---|---|---|---|
| Chemical Formula | | | | | |
| Color | white latex | white latex | white latex | Milky white (solution) | White powder (lyophilized) |
| Odor | None | None | None | None | None |
| Melting point/ ° C. | 240° C. | 240° C. | 240° C. | 4500 K | N/A (amorphous) |
| Glass Transition/° C. | 100° C. | 100° C. | 100° C. | N/A | 40-55° C. |
| Solubility | Insoluble in water or alcohols, soluble in acetone, ethyl acetate, THF, DMF, toluene, methylene chloride, etc. | Insoluble in water or alcohols, soluble in acetone, ethyl acetate, THF, DMF, toluene, methylene chloride, etc. | Insoluble in water or alcohols, soluble in acetone, ethyl acetate, THF, DMF, toluene, methylene chloride, etc. | N/A | Insoluble in water, soluble in acetone, ethyl acetate, DMSO, DMF, acetonitrile, chloroform, methylene chloride, etc. |
| CoPolymer ratio (mol %) | 90:10 | 100:0 | 90:10 | N/A | 50:50 |
| Melt Index g/10 Minutes, 200° C./5 kg | 6.0-9.0 | 6.0-9.0 | 6.0-9.0 | N/A | N/A |
| MW (kDa) | 10-250 | 10-250 | 10-250 | 22,000,000 KD | 5-50 |
| Residual monomer | unknown | unknown | unknown | N/A | <0.5% lactide <0.5% glycolide |
| Sn content (ppm) | N/A | N/A | N/A | N/A | <100 (ICP) |

TABLE 3-continued

Physical Properties of the Particles
Physical Properties

| | Immune Modified (Carboxylated) Polystyrene Particles (Phosphorex) | Polystyrene Neutral Particles (Phosphorex) | Polystyrene Positive Charged (Aminated Particles-Phosphorex) | Immune Modified Nano-Diamonds (University of Sydney) | Immune Modified (Carboxylated) PLGA Particles (Phosphorex) |
|---|---|---|---|---|---|
| Heavy metals (ppm) | unknown | unknown | unknown | 0-0.55% Nickel 0-0.50 Copper prior to carboxylation by acid washing | <10 |
| Sulphate Ash (%) | unknown | unknown | unknown | N/A | <0.1 |
| Size distribution | 10.4% | 2.4% | 10.4% | 270 ± 30 nm | 10-50% |
| Zeta Potential | −40~−50 mv | −5~+5 mv | +20~+40 mv | −50.6 +/− 3 mV | −30~−50 mV |

Statistics

Graphs were made and statistical analyses were performed in Graph Pad Prism (Graph Pad software, SDG, USA). To compare two samples an unpaired two-tailed Student t-test was conducted. To compare three or more samples, a one-way ANOVA with a Tukey-Kramer post-test was performed. For survival data, the Mantel-Haenszel logrank test was conducted. For these tests, P≤0.05 (*) was deemed significant, and P≤0.01 (**) very significant.

Example 1

Opsonized IMPs have Reduced Ability to Inhibit Macrophage Migration to the Brain.

Figure 9:
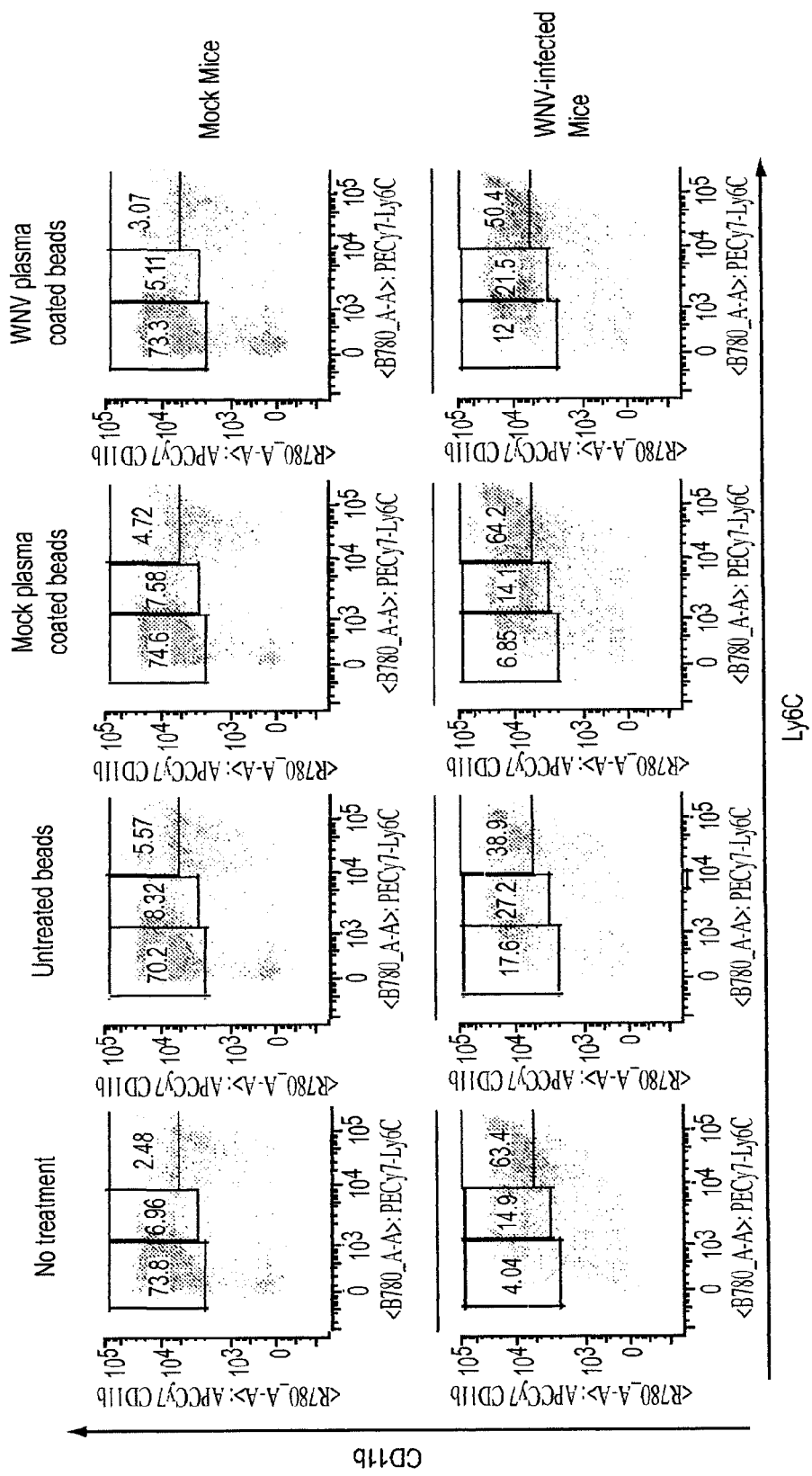
FIG. 9 shows opsonized IMP have reduced ability to inhibit macrophage migration to the brain. Day 7 plasma was taken from mock or WNV infected animals and incubated with PS-IMP. These "opsonized" particles or unopsonized (untreated beads) particles were re-infused into WNV infected mice at day 6 p.i. On day 7 the brains were examined for inflammatory monocyte influx by flow cytometry. While untreated (Normal IMP) resulted in a reduced monocyte influx into the brain, mock plasma coated IMP had no ability to inhibit monocyte migration. Of interest WNV serum coated IMPs had a reduced ability to inhibit monocytes relative to uncoated IMP, but were still capable of reducing migration to some degree.

Day 7 plasma was taken from mock or WNV infected animals and incubated with PS-IMP. These "opsonized" particles or un-opsonized (untreated beads) particles were re-infused into WNV infected mice at day 6 p.i. On day 7 the brains were examined for inflammatory monocyte influx by flow cytometry. While untreated (Normal IMP) resulted in a reduced monocyte influx into the brain, mock plasma coated IMP had no ability to inhibit monocyte migration (FIG. 9). WNV serum coated IMPs had a reduced ability to inhibit monocytes relative to uncoated IMP, but were still capable of reducing migration to some degree.

Example 2

Figure 1B:
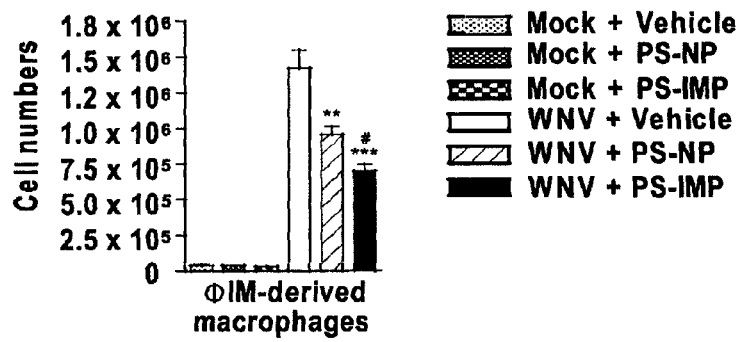

Immune-Modifying Particles Reduce Inflammatory Monocyte Migration and Increase WNV Survival A hallmark of acute and many chronic inflammatory diseases is the influx of monocytes into the area of inflammation. Previously, we have shown that morbidity associated with WNV brain infection is the direct result of inflammatory monocyte trafficking into the brain (Getts, 2008; Getts, 2007; Terry, 2012; Getts, 2012). In this model, weight loss of ≥5% is a biomarker that correlates with ΦIM trafficking into the brain and thus lethality (Getts et al., J. Neuroinflammation, In Press). At least 50% of infected animals will go on to lose weight, of which 100% will typically succumb to infection, within 72 hours of initial weight loss (FIG. 1A). Animals that do not lose weight do not show any other symptoms of encephalitis but still develop life long sterilizing immunity (FIG. 1A). To monitor monocyte trafficking, carboxylated, negatively charged polystyrene particles (PS-IMP) were unintentionally infused instead of polystyrene neutral particles (PS-NP) at initial weight loss (day 6). Surprisingly, infusion almost immediately reduced symptoms such as ruffled fur, malaise and seizures, uniformly associated with clinical WNV central nervous system (CNS) infection. This reduction correlated with a reduction in local pro-inflammatory cytokines and chemokines (FIG. 6). Furthermore, daily infusion of PS-IMP for up to 5 days resulted in 60% survival of mice that would otherwise have succumbed to infection (FIG. 1A). In these mice, body weight typically stabilized and returned to control levels within 5-6 days (not shown). PS-NP- or vehicle-treated mice showed continued weight loss, with ≤10% survival. Furthermore, pre-opsonisation of IMP before infusion, with serum from WNV or mock infected animals, had no impact on disease outcome (not shown). Consistent with our previous observations in WNV encephalitis (Getts, 2008; Getts, 2007; Terry, 2012; Getts, 2012), survival correlated with a significant reduction in ΦIM-derived macrophages in the brains of PS-IMP-treated mice, compared to phosphate buffered saline (vehicle)-treated, or PS-NP-treated control animals (FIG. 1B, FIG. 7).

Example 3

The Immune-Modifying Particles Must be Negatively Charged

Figure 1C:
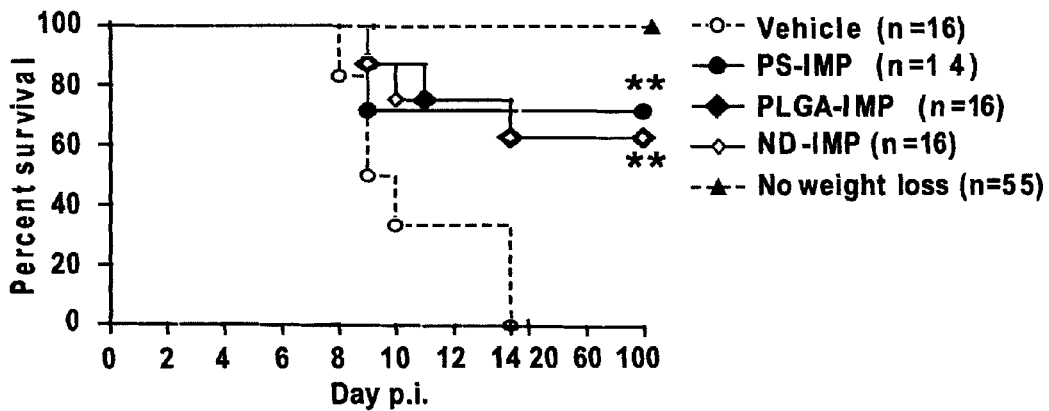
Figure 1D:
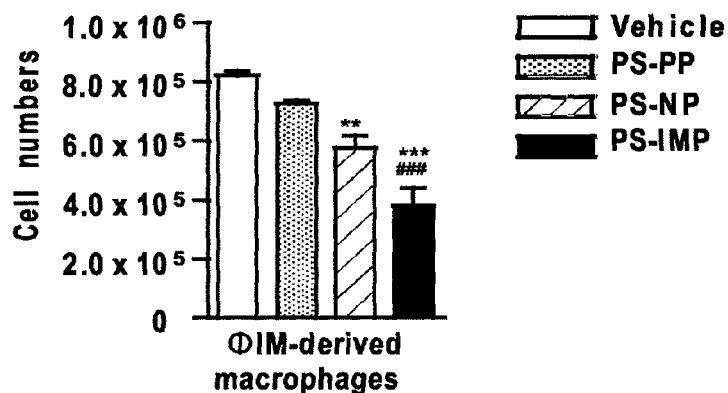
Figure 1E:
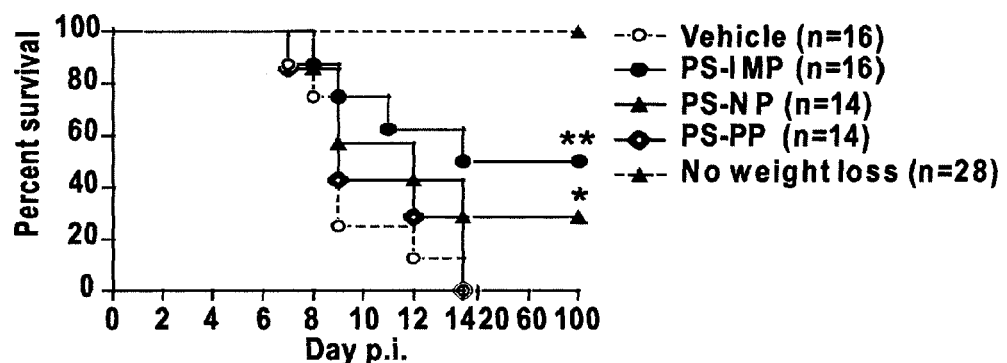
Figure 1F:
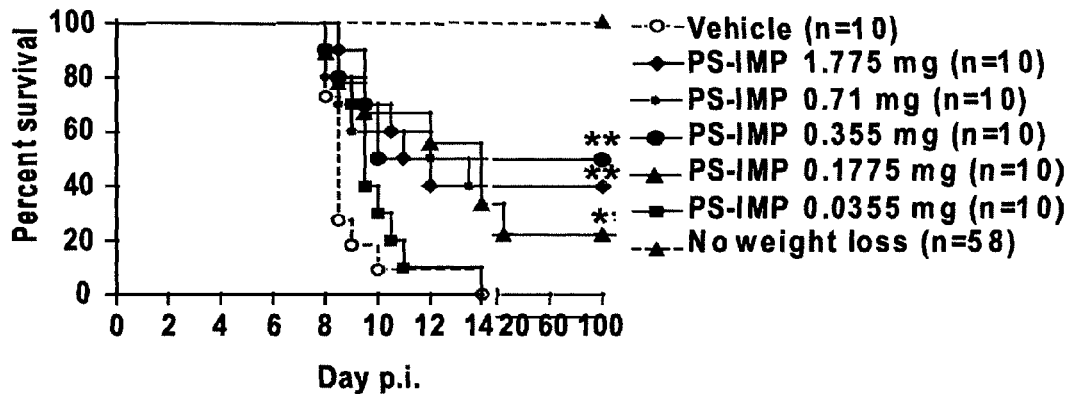
Figure 1G:
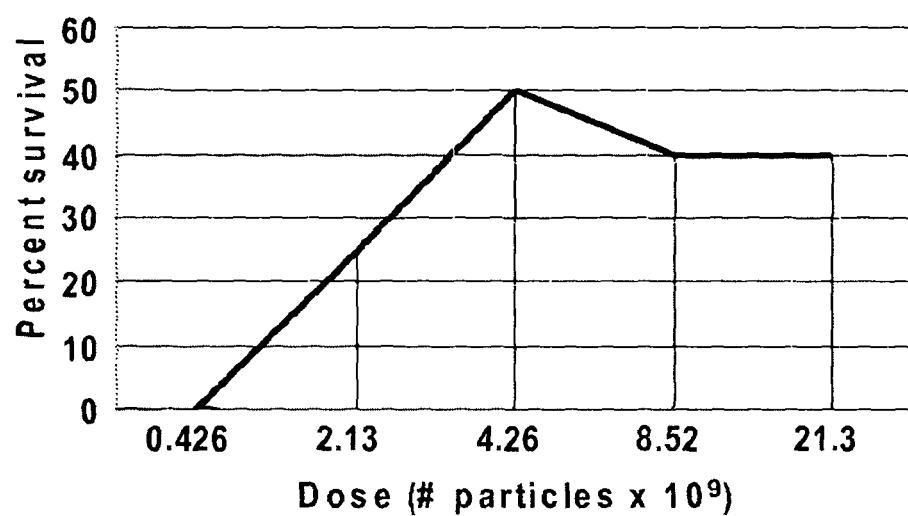

Treatment of WNV-infected animals with other carboxylated particles, specifically ND IMP, and PLGA-IMP, resulted in survival statistics similar to those seen in animals treated with PS-IMP (FIG. 1C), indicating that particle core is independent of the property responsible for the therapeutic effect. Initial pilot studies used carboxylated PS-IMP, with a zeta potential of less than −50 mV (Table 3). We thus compared PS particles with zeta potentials of −50 mV, ~−0.5 (neutral; Polystyrene Neutral Particles; PS-NP) or +40 mV (aminated particles, polystyrene-positive particles; PS-PP). PS-IMP (−50 mV) showed the greatest impact in regards to reduced inflammatory monocyte trafficking to the brain (FIG. 1D). In contrast, PP did not decrease infiltration of IM-derived macrophages (FIG. 1D), nor increase survival (FIG. 1E). The dose response for 500 nm PS-IMP in mice with WNV encephalitis showed the most effective dose to be ~4×10⁹ IMP particles or 0.355 mg of particles per mouse (FIG. 1F-G).

Example 4

Figure 2A:
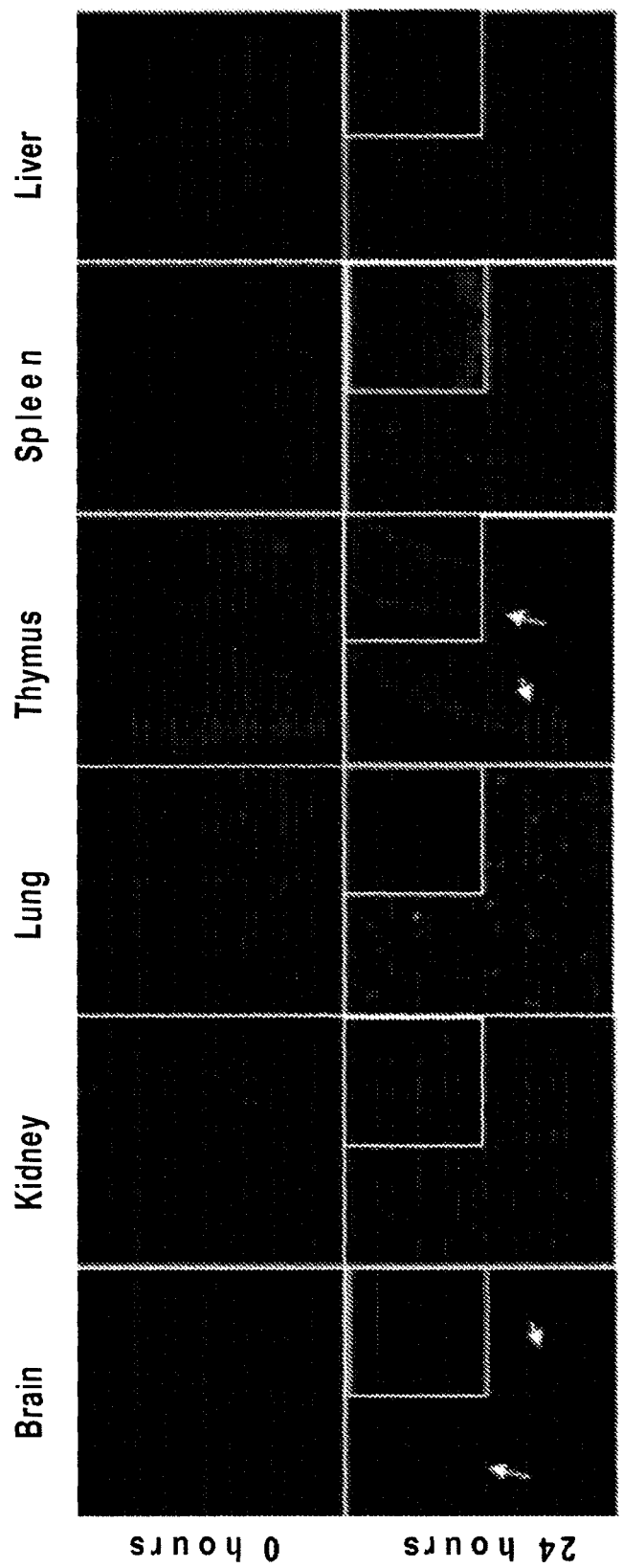
Figure 2B:
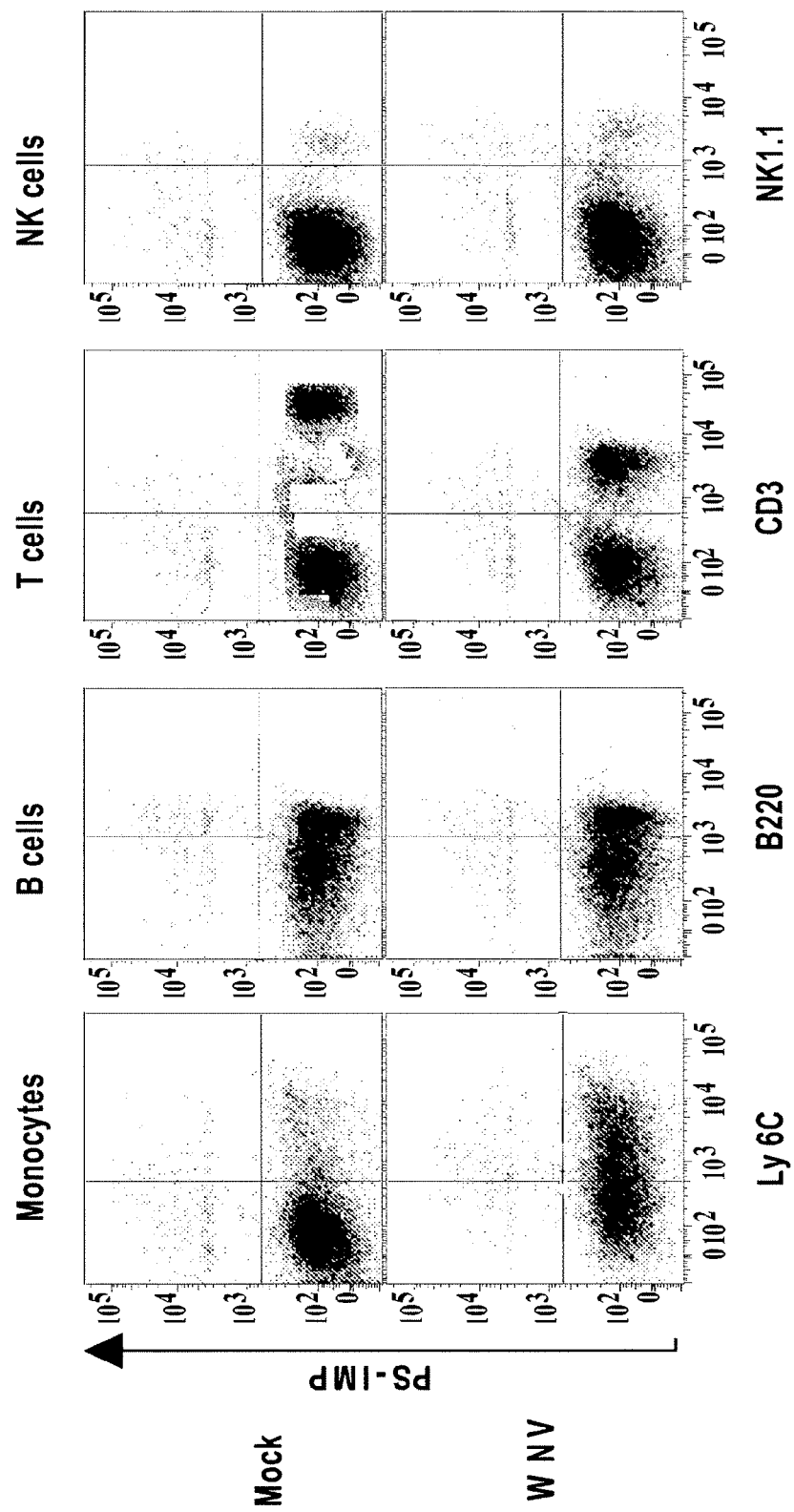
Figure 2C:
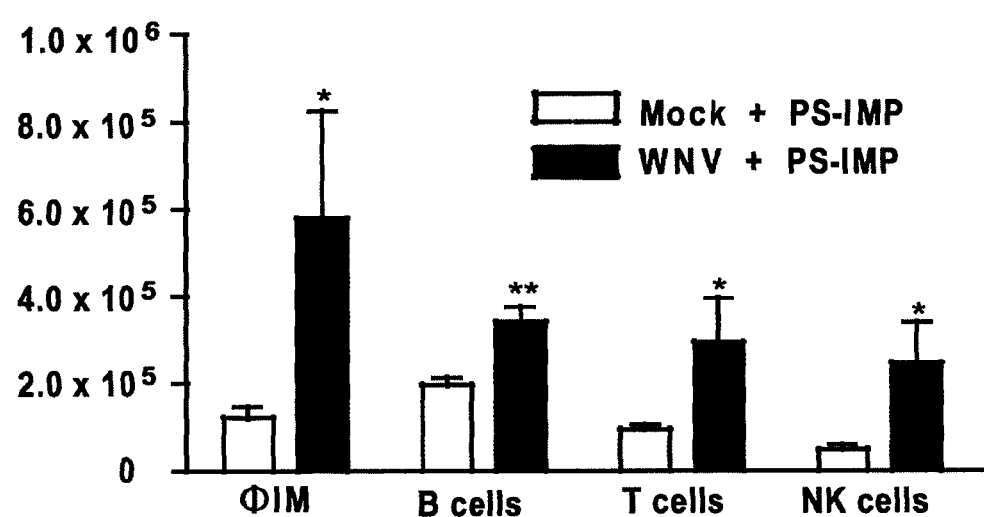
Figure 2D:
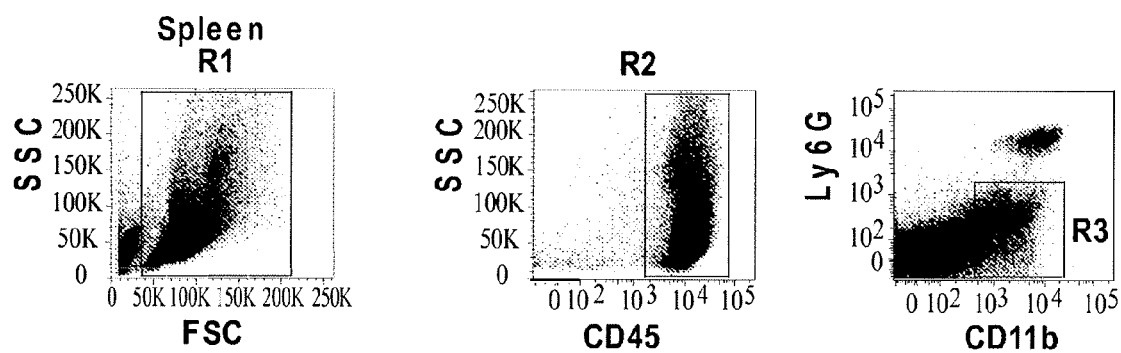
Figure 2E:
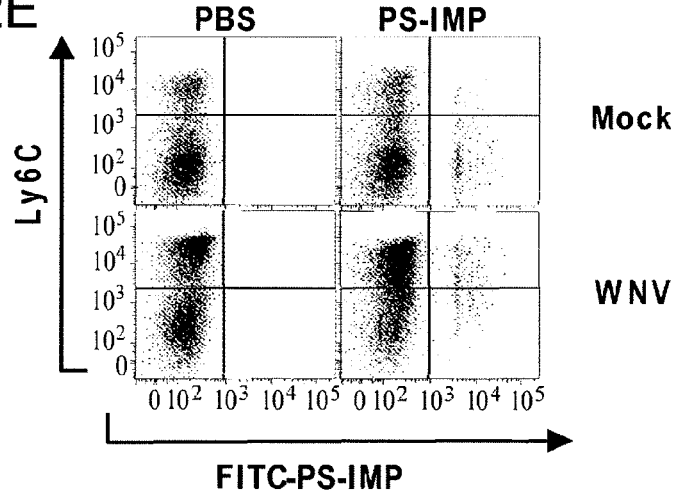
Figure 2F:
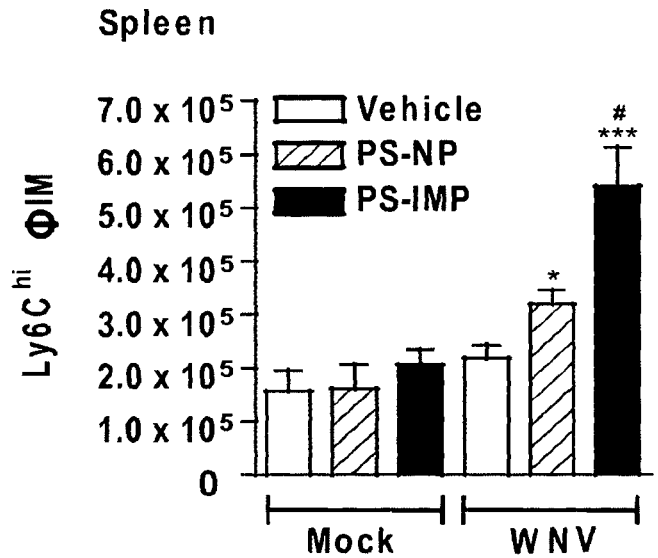
Figure 2G:
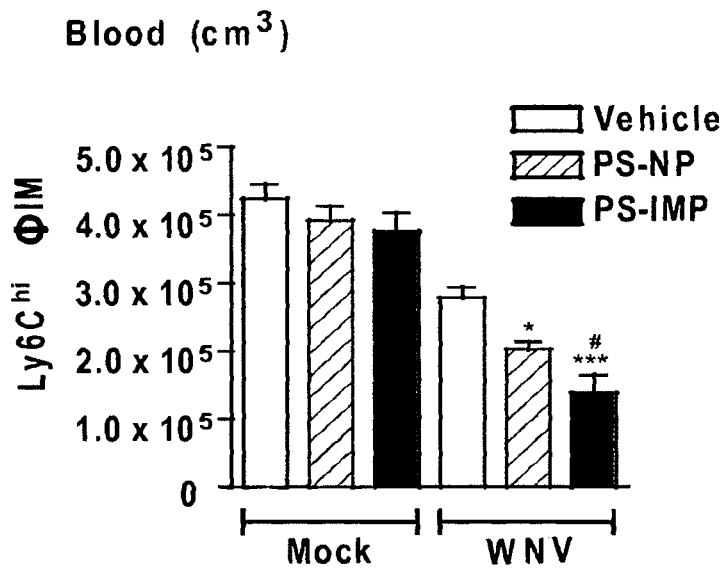

PS-IMP Treatment Results in Redirection of Inflammatory Macrophages to the Spleen Following infusion, PS-IMP predominantly localized to the lungs, spleen and liver (FIG. 2A), with no FITC$^+$ particles in the brain and thymus (FIG. 7A-B) and none found in peripheral lymph nodes (data not shown). Flow cytometry revealed a relatively even distribution of IMP among inflammatory monocytes, BB20$^+$ B cells, CD3$^+$ T cells, and NK1.1 cells (FIG. 2 B-C), however, in infected mice, inflammatory monocytes were found to take up significantly more IMP than any other cell type in the spleen (FIG. 2 B-C). Within the circulation, the phenotype of IMP-containing monocytes in mock-infected mice was Ly6C-negative, whereas IMPs localized primarily to Ly6C-positive monocytes in the infected animal (FIG. 2D-E). Furthermore, spleens from WNV-infected mice treated with FITC-PS-IMP had significantly more inflammatory monocytes than those treated with NP or vehicle control (FIG. 2F; FIG. 9), closely corresponding to a decrease in circulating inflammatory monocytes in the peripheral blood in these mice (FIG. 2G).

Figure 3A:
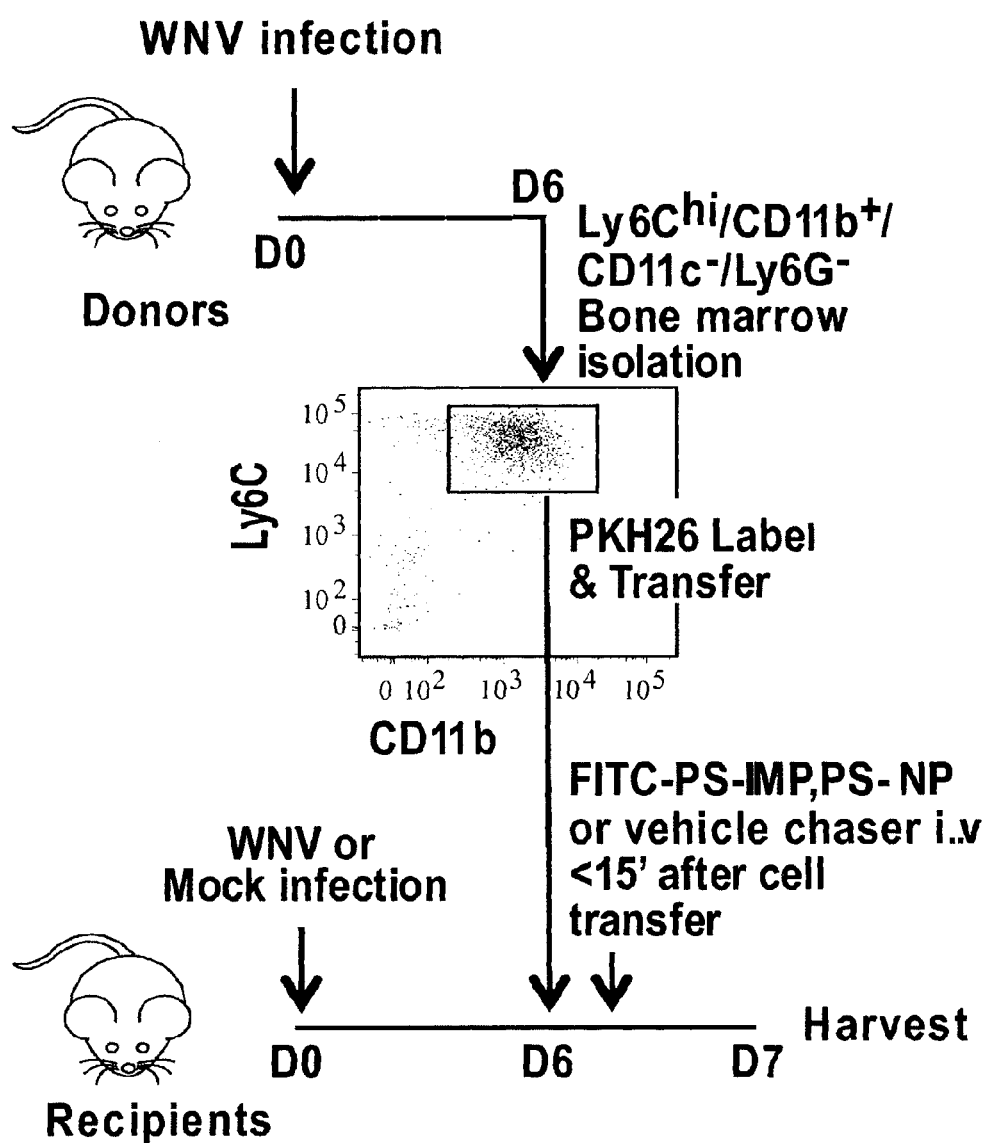
Figure 3B:
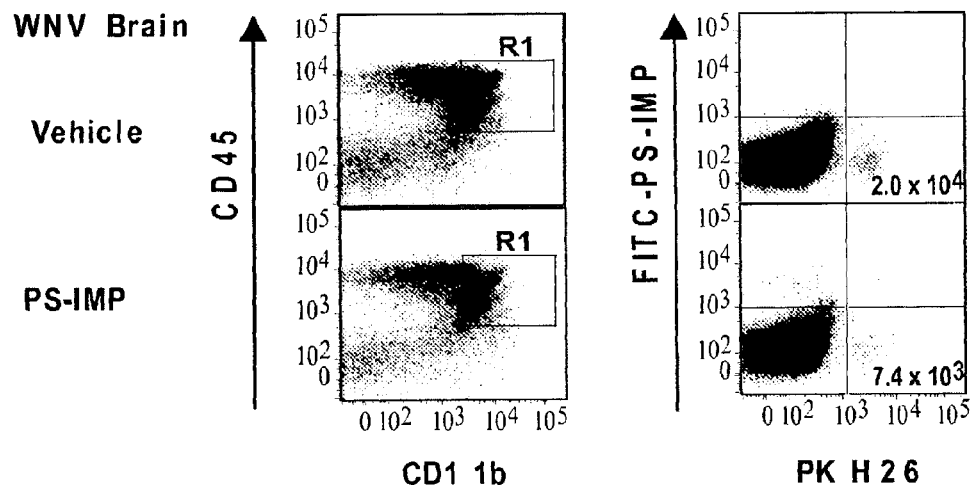
Figure 3C:
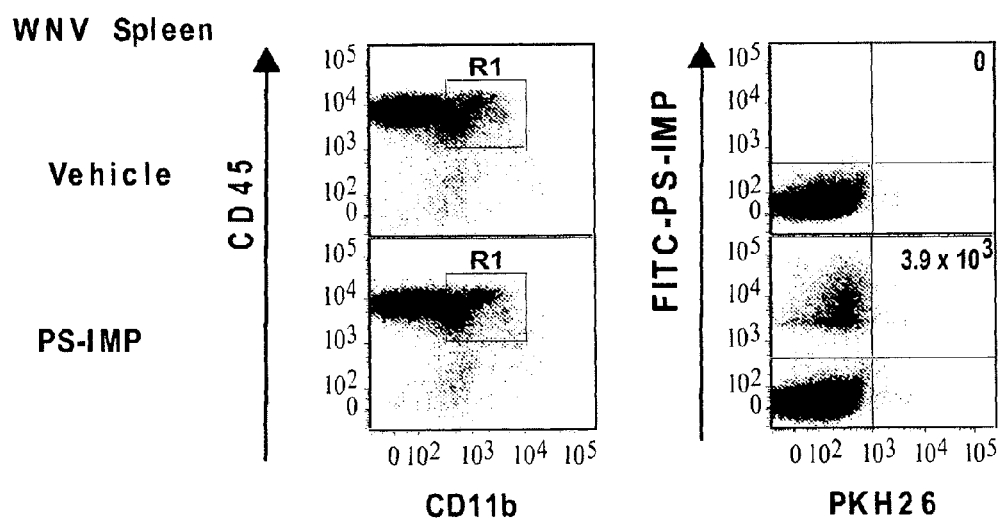

It has previously been shown that morbidity in WNV encephalitis is caused by inflammatory monocytes (Terry et al., 2012; Getts et al., 2012). When combining these previous findings with the data obtained here, we hypothesized that IMPs mediate their therapeutic activity by binding to inflammatory monocytes, abrogating their migration to the inflamed brain instead diverting them to the spleen. To confirm this, Ly6C$^{hi}$ monocytes were sorted from the bone marrow of WNV-infected mice on D6 p.i., labelled with PKH26 and transferred i.v. into mock- or WNV-infected recipients on D6 p.i (FIG. 3A). This was followed immediately by injection with PS-IMP, NP or vehicle only. PKH26-labelled Ly6C$^{hi}$ inflammatory monocytes trafficked into the WNV infected brain, differentiating into macrophages, with no peripheral immune cells observed in the mock-infected brain (FIG. 3B, data not shown). As described in Getts et al. (J. Exp. Med. 205:2319-2337, 2008) PS-IMP treatment reduced the host inflammatory monocyte infiltration into the WNV-infected brain (FIG. 3B), with significantly fewer adoptively-transferred PKH26$^+$ cells migrating into the brain (FIGS. 3B and 3D). Migration of PKH26-labelled cells into the spleen (FIGS. 3C and 3E) was observed in mock- and WNV-infected mice, however, PS-IMP treatment resulted in significantly more Ly6C$^{hi}$ monocyte accumulation in the spleens of WNV-infected mice (FIG. 3E). The importance of the spleen in the efficacy of IMP treatment was confirmed in splenectomised mice. IMP infusion failed to reduce immigration of inflammatory monocytes into the brains of WNV-infected splenectomised mice, compared to splenectomised, vehicle-treated, WNV-infected control mice (FIG. 3F). The spleen has recently been shown to harbour a reservoir of monocytes, identified as CD11b$^+$/Ly6C$^{hi}$/CD11c$^-$, that may be recruited from the spleen under certain inflammatory conditions (Swirski et al., Science 325:612-616; 2009; Leuschner et al., J. Exp. Med. 209:123-137, 2012; Robbins et al., Circulation 125:364-374, 2012). We hypothesized that IMP infusion enhanced this pool of splenic monocytes. However, more than 70% of the adoptively transferred monocytes that had taken up IMP and migrated to the spleen, expressed CD11c and CD103 (FIGS. 3E and 3G), making this hypothesis unlikely. Taken together these data suggest that infused IMP are taken up by inflammatory monocytes, which are diverted to the spleen, resulting in reduced inflammatory monocyte numbers in the blood for migration into sites of inflammation.

Example 5

IMPs Inhibit Inflammatory Monocyte Migration into the Inflamed Peritoneum

Figure 4A:
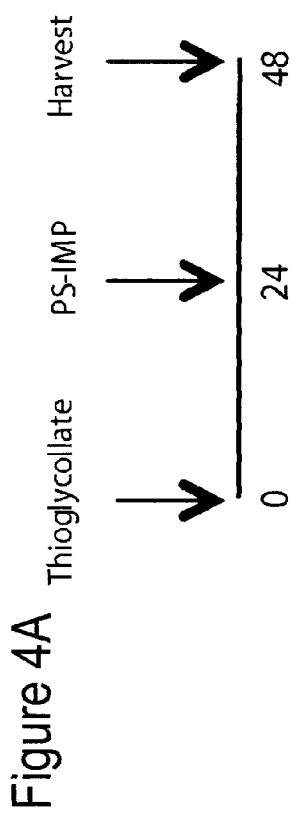
Figure 4B:
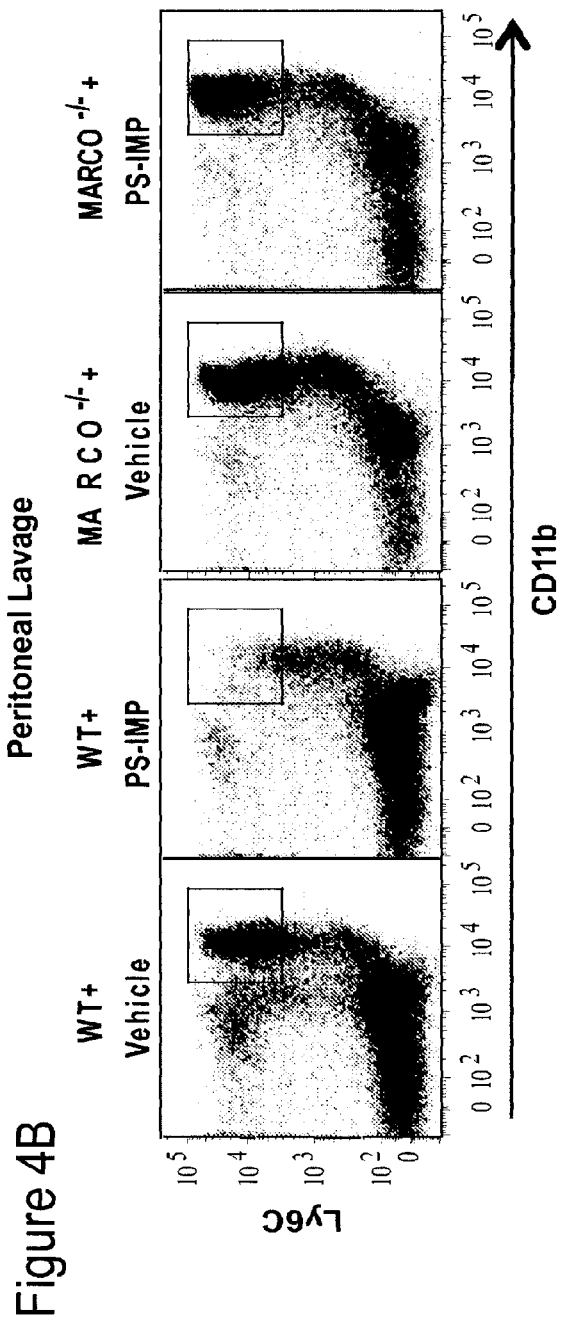

It is clear that monocytes are an important mediator of immune pathology observed during WNV encephalitis, however, infection results in a complex array of immune responses involving other cellular subsets. To address the specificity of IMP to inflammatory monocytes during inflammation, a model of sterile macrophage-mediated peritoneal inflammation was used. The migration of leukocytes into the thioglycollate-inflamed peritoneum follows a stereotypical pattern, with neutrophils elicited within the first 4-18 hours, followed by the CCR2-dependent accumulation of ΦIM-derived macrophages from approximately 12 hours onwards (Tsou, et al., 2007). Infusion of either PS-IMP (FIG. 7D-E; FIG. 4A-B) or PLGA-IMP (not shown), 24 hours after intraperitoneal thioglycollate injection, significantly reduced inflammatory monocyte trafficking into the site of inflammation which was abrogated in splenectomised mice (FIG. 7F). This data together both highlight the anti-inflammatory nature of IMP in a predominately macrophage mediated inflammatory model but also the importance of the spleen for IMP efficacy.

Example 6

Inflammatory Monocytes Express MARCO, which is Crucial for IMP Activity

Figure 4C:
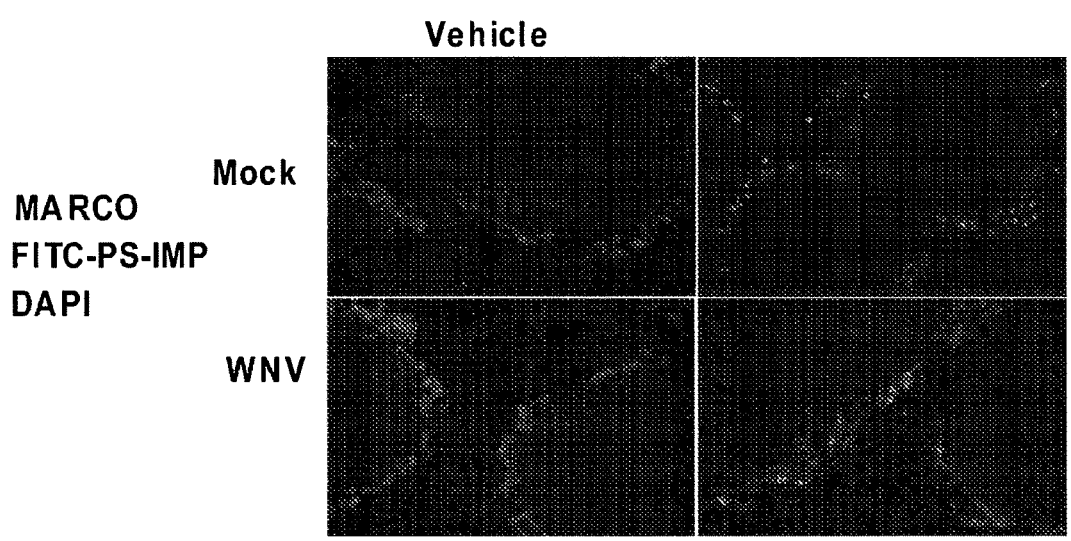
Figure 4D:
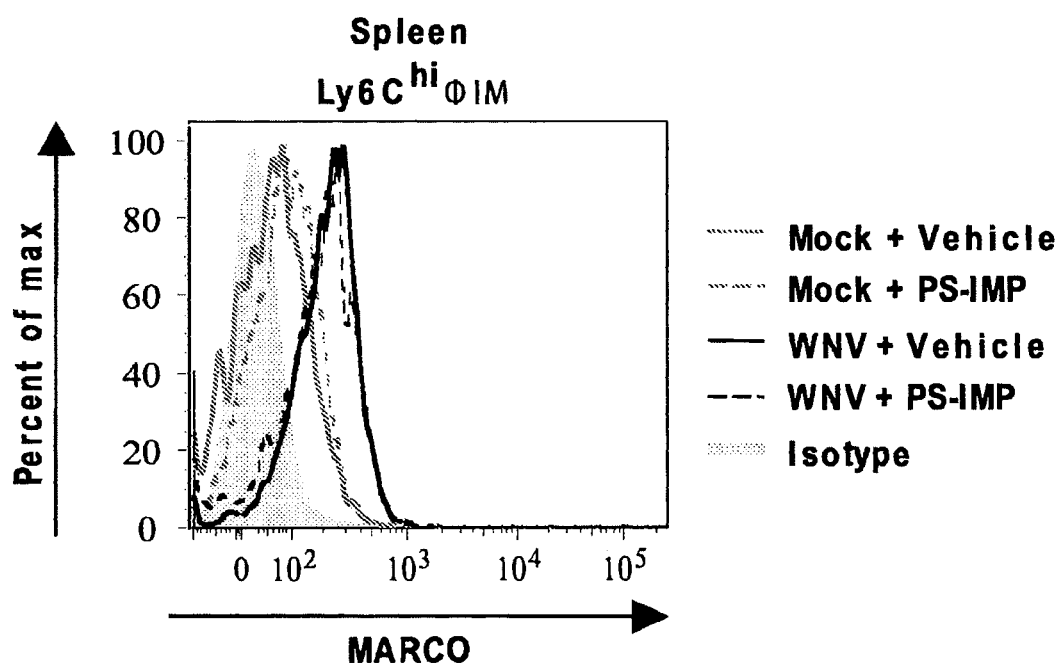
Figure 4E:
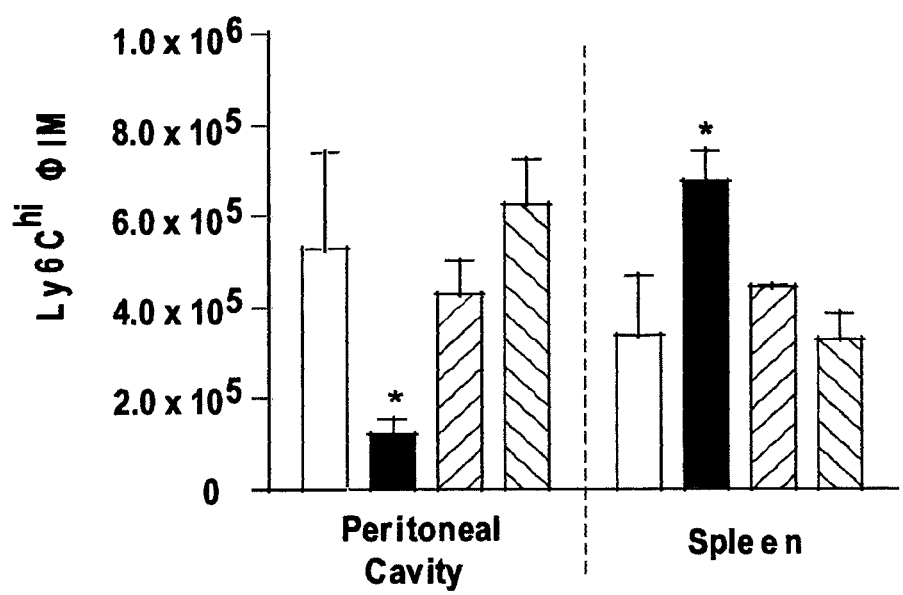
Figure 4F:
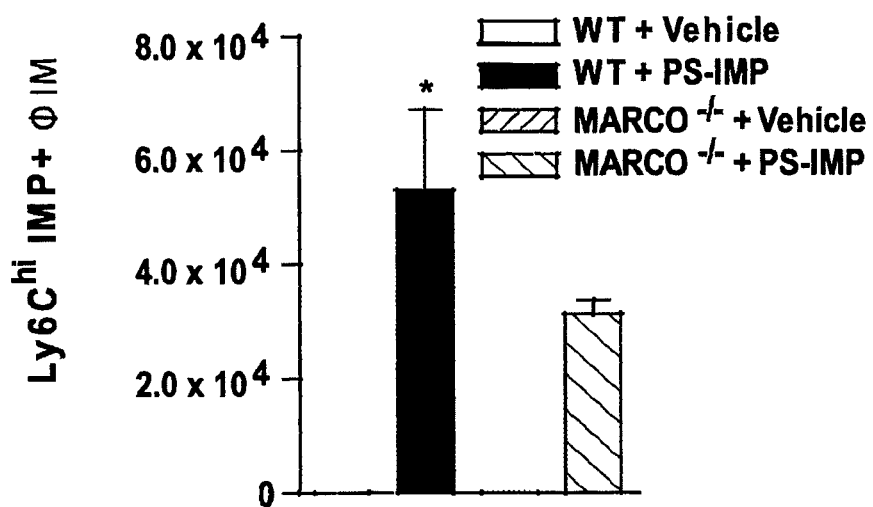
Figure 4G:
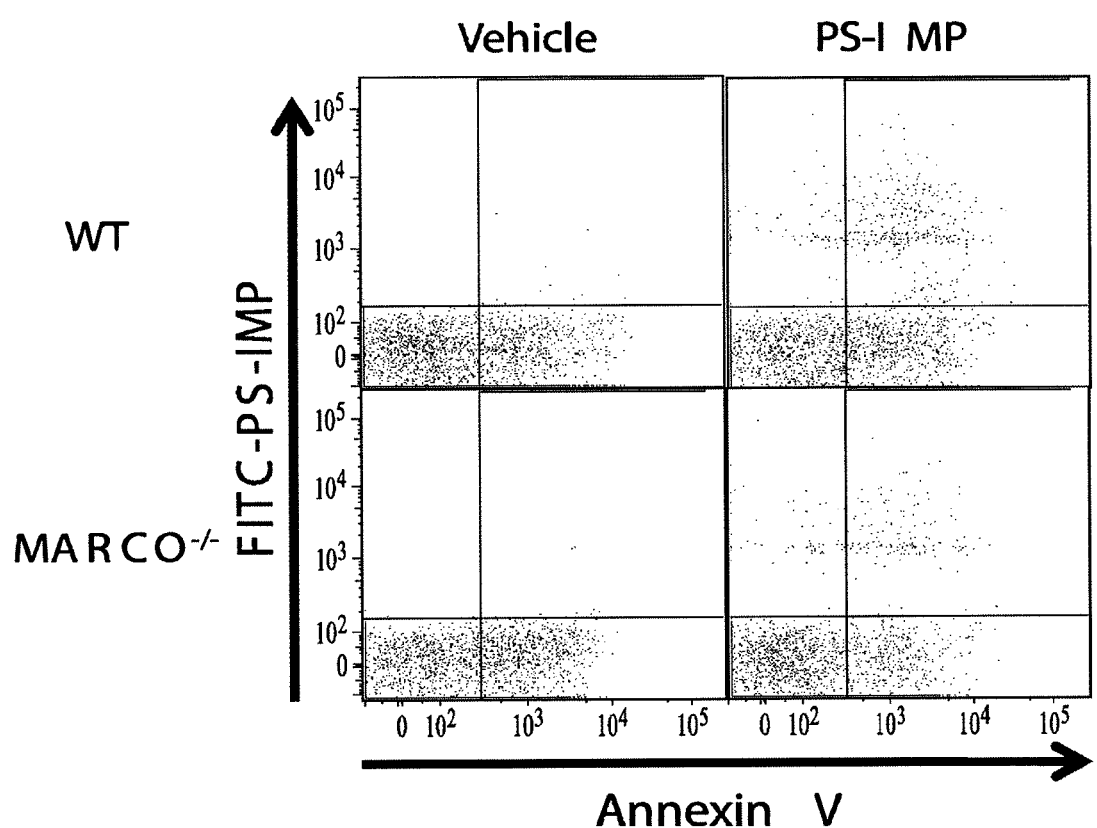
Figure 4H:
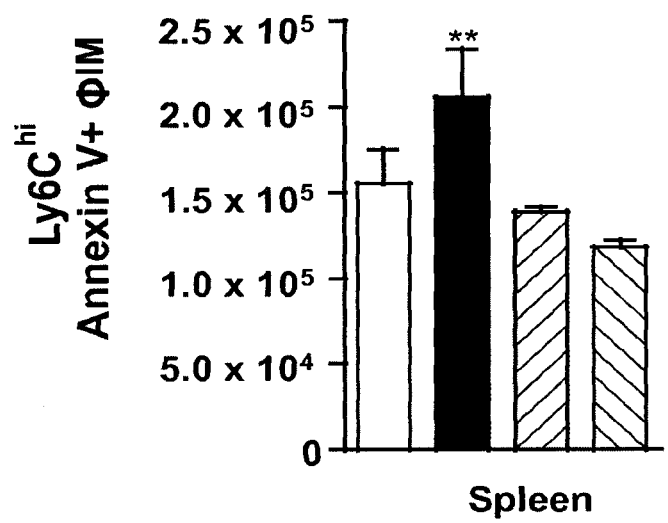
Figure 4I:
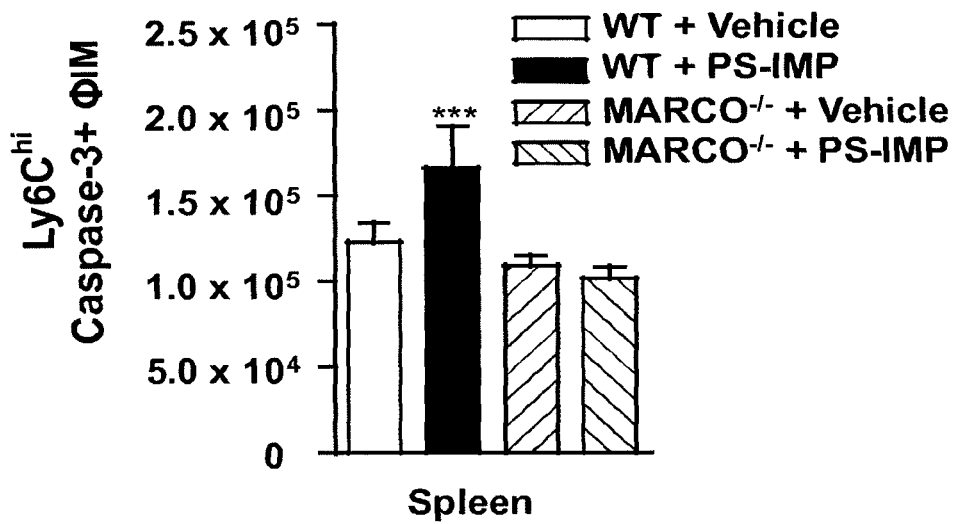
Figure 10A:
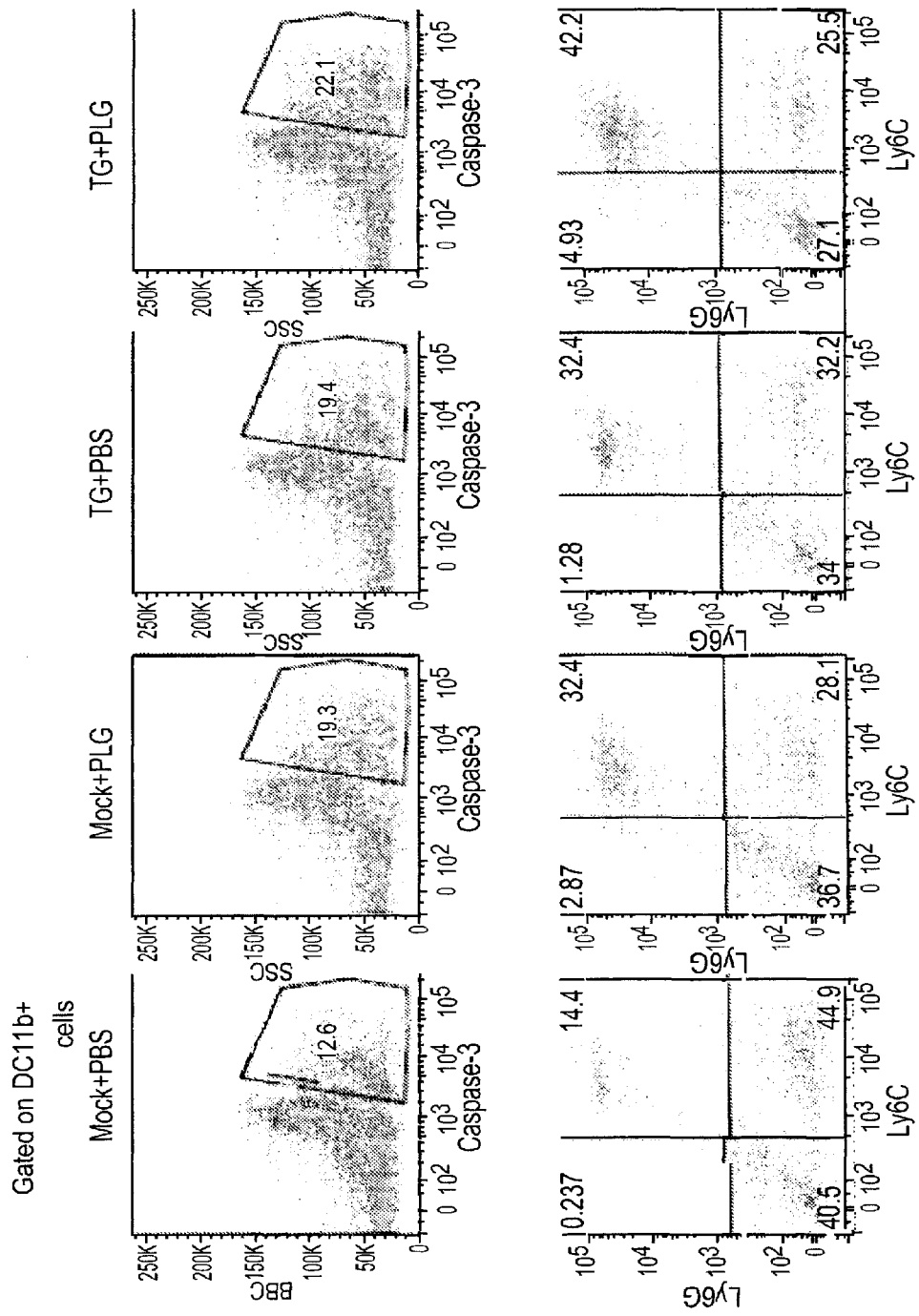
FIG. 10 shows (A-B) PLGA-IMPs induce apoptosis in TG model in both inflammatory monocytes and neutrophils. Infusion of PLGA-IMP into thioglycolate-induced WT mice resulted in a significant increase in numbers of Ly6C$^{hi}$ ΦIM and Ly6G$^+$ Neutrophils which expressed the apoptosis markers annexin V and caspase-3. This was not observed in mock treated animals (a). Flow cytometry data are means and represent three separate experiments with 4-5 mice/group (b). Statistical analysis was conducted using one-way ANOVA and Tukey-Kramer post-test. P≤0.05 (*), P≤0.01 (), P≤0.001 (*), in comparing the WT PS-IMP groups to all other groups.
Figure 10B:
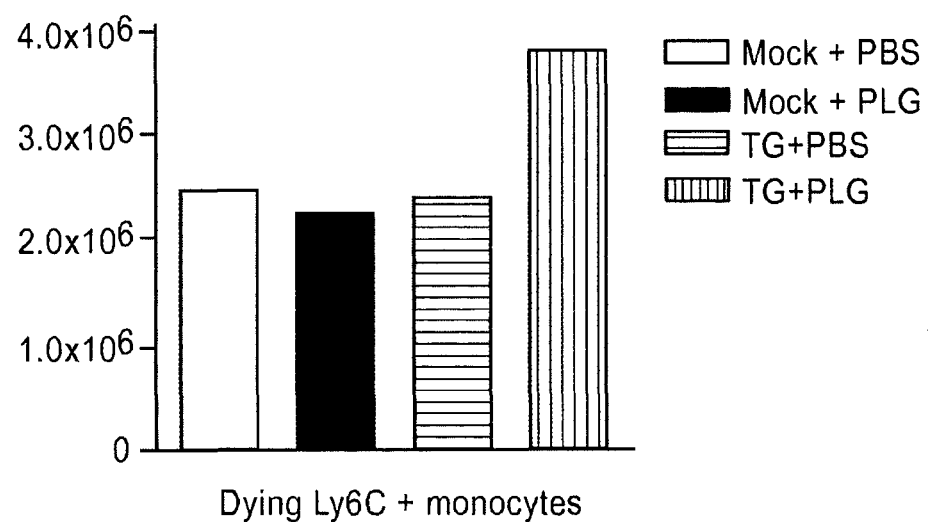
Figure 10B:
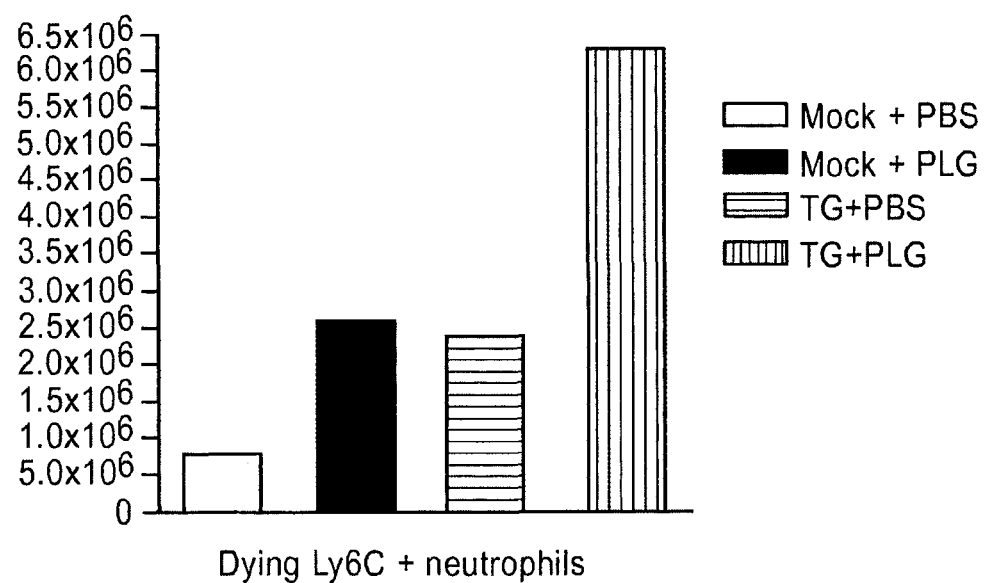
Figure 11A:
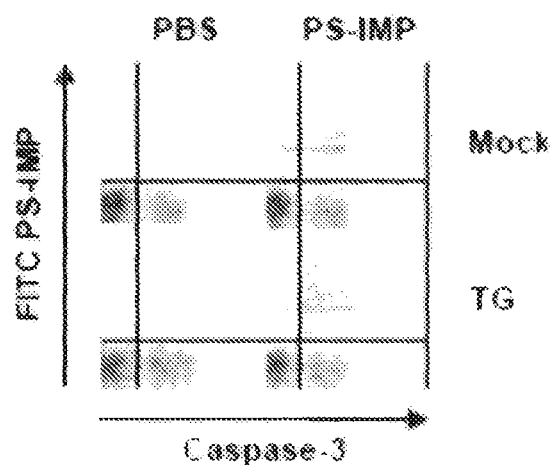
FIG. 11 shows (A-B) apoptosis can be detected within 2 hours post PLGA or PS IMP infusion. Two hours after injection, PS-IMPs were localized in CD11b+ Ly6C+ Ly6G- monocytes in the spleens of mock and TG peritonitis-induced mice. Uptake of PS-IMP was associated with activity of the enzyme Caspase-3, indicative of apoptosis (a). Increased numbers of monocytes were positive for caspase-3 activity in PS-IMP treated, TG peritonitis-induced mice (b).
Figure 11B:
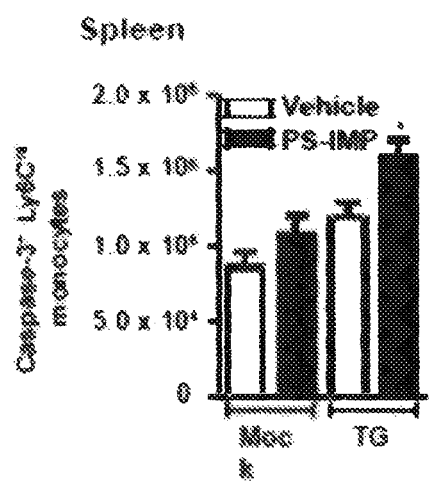
Figure 12:
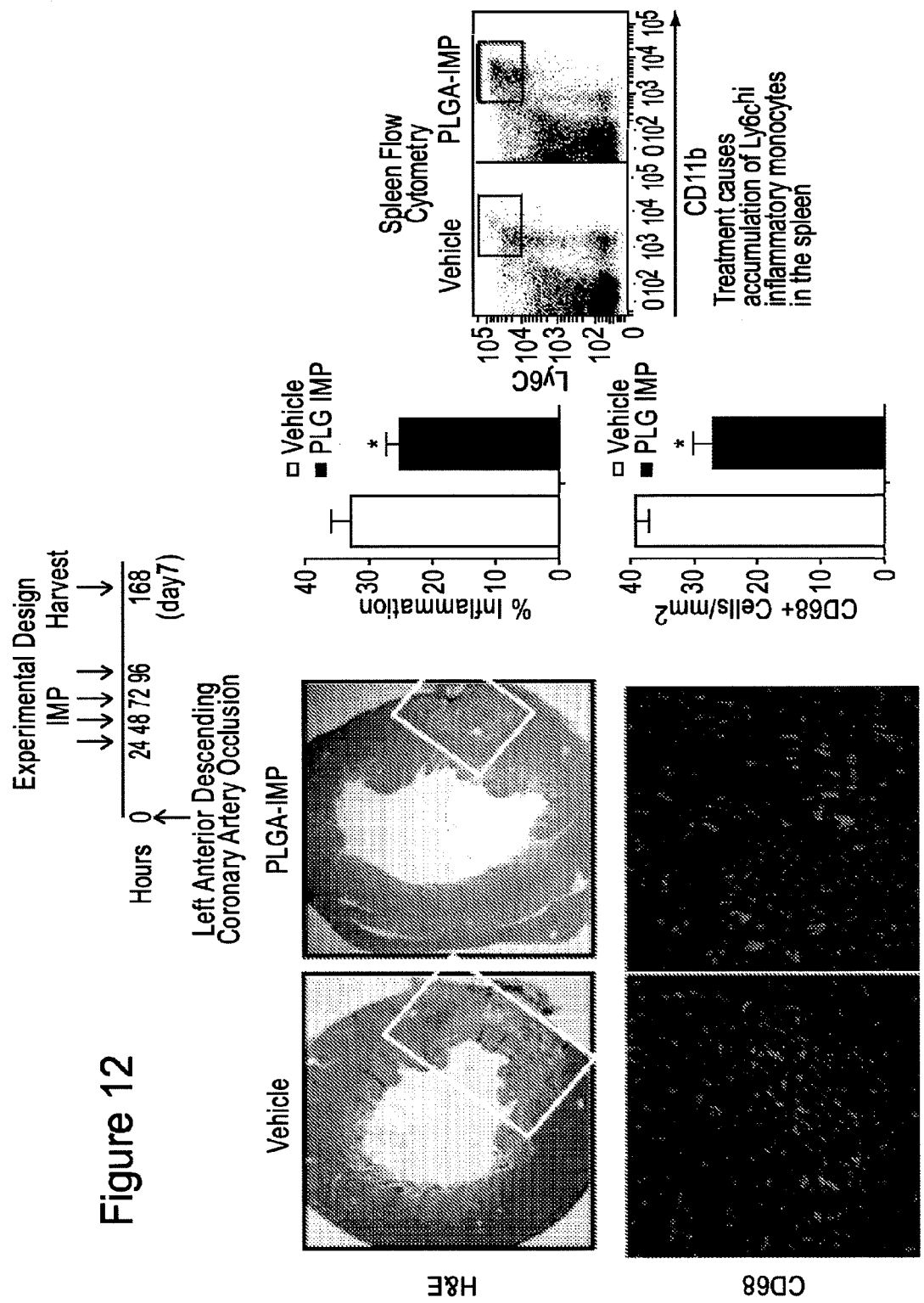
FIG. 12 shows that PLGA-IMPs protect from inflammatory damage in a myocardial infarction model. Four days of PLGA-IMP infusion resulted in reduced infarction size, as determined by H&E histology and image analysis compared to vehicle-treated controls. In addition, the reduced occlusion size correlated with fewer CD68+ macrophages in PLGA-IMP-treated mice compared to vehicle treated controls and an increase in Ly6C$^{hi}$ cells in the spleen.

Particles such as IMP are to be taken up through scavenger receptor pathways (Kanno et al., 2007). One key scavenger receptor specifically implicated in the binding of negatively-charged particles as well as polystyrene is MARCO (Chao, et al., 2012; Kanno, et al., 2007). In the spleen, PS-IMP co-localized with MARCO expressing cell populations in the marginal zone, similar to what we have previously described for apoptotic cell uptake after intravenous infusion (Getts, et al., 2011; Getts, et al., 2012) (FIG. 4C). MARCO was also found to be up-regulated on Ly6c$^{hi}$/CD11b$^+$/CD11c$^-$ ΦIM isolated from the spleen of WNV-infected but not mock-infected animals (FIG. 4D). To further address the role of MARCO, peritoneal inflammation was induced in MARCO-deficient (MARCO$^{-/-}$) animals using thioglycollate. Similar numbers of peritoneal monocytes were isolated from WT and MARCO$^{-/-}$ mice 48 hours after thioglycollate administration (FIG. 4B, 4E). However, unlike WT mice, where PS-IMP treatment resulted in reduced numbers of Ly6C$^{hi}$/CD11b$^+$ ΦIM in the peritoneum, PS-IMP treatment infusion did not reduce the number of peritoneal Ly6C$^{hi}$/CD11b macrophages isolated from MARCO$^{-/-}$ animals (FIG. 4B, 4D), directly pointing for a role for MARCO in the uptake and efficacy of IMP. In addition, MARCO has been shown to also play a direct role in the apoptosis induction in macrophages that have engulfed silica particles (Hamilton et al., 2006). Interestingly, IMP significantly increased the numbers of annexin V and caspase-3 positive inflammatory monocytes in the spleens of WT mice but not MARCO$^{-/-}$ mice 2 hours after infusion of PS-IMP (FIG. 4G-I; FIG. 11B) or PLGA-IMP (not shown). Apoptosis is induced in both neutrophils and inflammatory monocytes and is detectable within 2 hours after IMP infusion (FIG. 10). Mice were injected with PS-IMP or PBS and sacrificed 2 hours later. Spleens were removed, processed into single cell suspensions and stained with anti-CD11b, Ly6C, CD11b, Ly6G, Fixable viability dye eFluor780 (eBioscience). Apoptotic cells were detected using the CaspGLOW™ Fluorescein Active Caspase-3 Staining Kit. Infusion of PLGA-IMP into thioglycolate-induced WT mice resulted in a significant increase in numbers of $Ly6C^{hi}$ ΦIM and $Ly6G^+$ neutrophils which expressed the apoptosis markers annexin V and caspase-3. This was not observed in mock treated animals. Two hours after injection (FIG. 11), PS-IMPs were localized in CD11b+ Ly6C+ Ly6G− monocytes in the spleens of mock and TG peritonitis-induced mice. Uptake of PS-IMP was associated with activity of the enzyme Caspase-3, indicative of apoptosis (a). An increased number of monocytes were positive for caspase-3 activity in PS-IMP treated, TG peritonitis-induced mice (b).

There were very few necrotic cells (less than ~5%) which indicates that the cell death is not associated with degrading IMPs.

Taken together, the data suggest that IMP are likely to be taken up through the MARCO scavenger receptor, which may mediate downstream signaling7 pathways that result in inflammatory monocyte migration, accumulation and subsequent apoptosis in the spleen.

Example 7

IMP Therapy Inhibits Inflammatory Monocytes in EAE

Figure 5A:
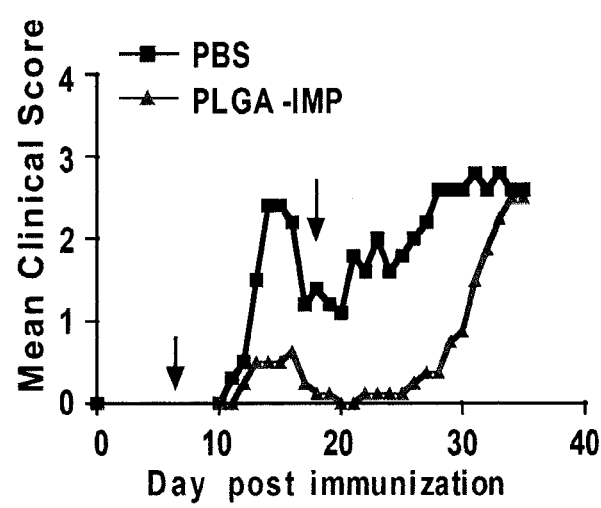
FIG. 5 shows (A-P) PS-IMP ameliorate disease pathology and infiltration of inflammatory monocytes in EAE, myocardial inflammation and inflammatory bowel disease. PLGA-IMP infusion commencing at the onset of EAE (a) or primary relapse (b) in SJL mice immunized with PLP$_{139-151}$ significantly reduced mean clinical scores. Flow cytometry on spinal cords from mice treated with either PLGA-IMP or vehicle, for 7 days from day 7 post immunization, had significantly less inflammation, as determined by reduced CD45$^+$ CD11b$^+$ CD11c$^+$ Ly6C$^{hi}$ cells (c). This reduced monocyte influx into the spinal cord correlated with increased CD45$^+$ CD11b$^+$ Ly6C$^+$ monocytes in the spleen (d). As another model of inflammation, PLGA-IMP (infused as shown in e) were also tested in the permanent left anterior descending artery occlusion model. Three days of PLGA-IMP infusion, as shown in (e), resulted in reduced infarction size, as determined by H&E histology and image analysis described in the Materials and Methods, compared to vehicle-treated controls (f, h). In addition, the reduced occlusion size correlated with fewer CD68$^+$ macrophages in PLGA-IMP-treated mice compared to vehicle treated controls (g, i, red fluorescence). In another model of inflammation, the artery was ligated for 45 minutes and blood flow was allowed to return there after. Mice were treated with PLGA-IMP for 6 days as indicated in (j). At day 1 and day 5, serum creatinine clearance was significantly greater in animals that had been treated with IMP compared to vehicle treated controls (k). This correlated with reduced tubular atrophy in IMP treated animals (l). As another model of inflammation, PS-IMP therapy was tested in the DSS-induced colitis model, with infusion regimen for PS-IMP or vehicle shown in (m), reducing the overall clinical severity of DSS-induced colitis (n). Reduced clinical score correlated with reduced numbers of Gr-1$^+$ cells with monocytic (i.e., non-polymorphonuclear) morphology (o, p). EAE mean clinical score data are representative of three separate experiments with 10-20 mice/group. Flow cytometry data are means±SD and represent three separate experiments with 4-5 mice/group. Cardiac infarction data are representative of 2 experiments with at least 3 mice per group. Kidney ischemia reperfusion data are representative of 2 experiments with at least 4-5 mice per group. DSS-colitis data are representative of at least 3 experiments with at least 3 mice per group. Image analysis was performed as described in the Materials and Methods. Statistical analysis was conducted using unpaired, two-tailed Student T tests. P≤0.05 (*), P≤0.01 (), P≤0.001 (*) in comparing PS-IMP and vehicle control group. Statistical Analysis for the comparison by using two way analysis of variance (ANOVA) with post hoc Bonferroni's correction (Graph Pad Prism 6.0 software). *p<0.05, p<0.01, *p<0.001. n=5 for sham; n=7 per group for day 1; n=4-5 for day 5 for control group (as 3 animals were dead at days 3-4. We only collected one sample around day 4.3 so tubular score data was included) and n=7 for day 5 neg beads.
Figure 5B:
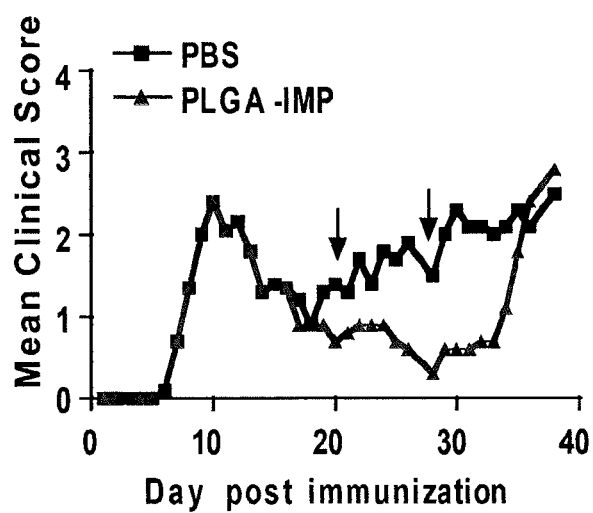
Figure 5C:
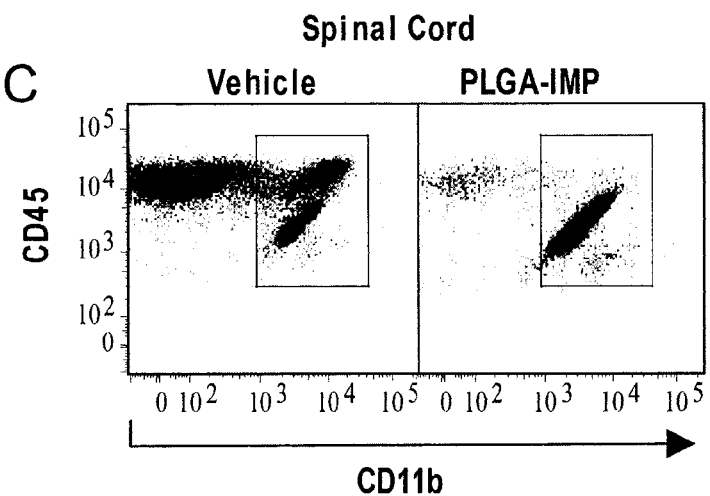
Figure 5D:
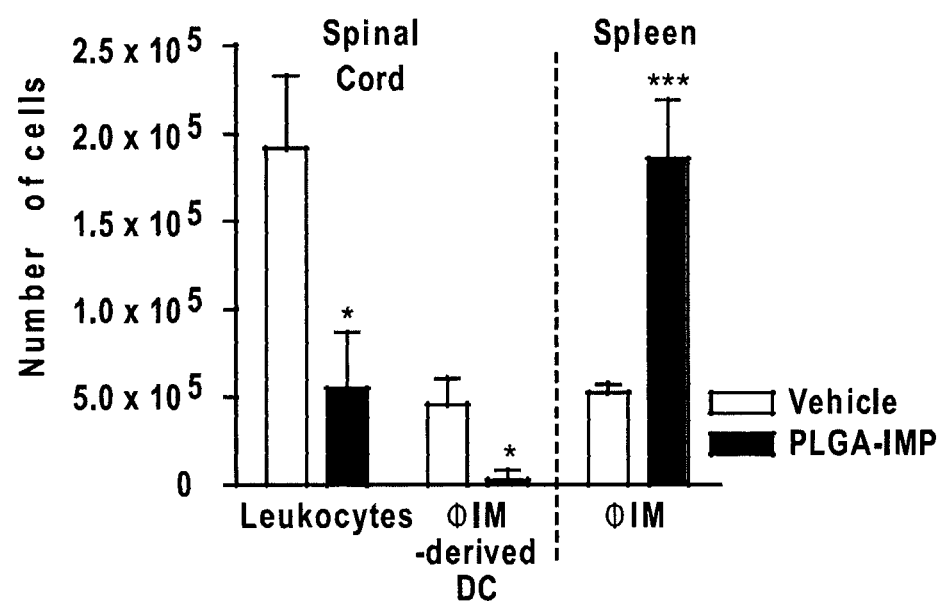
Figure 8A:
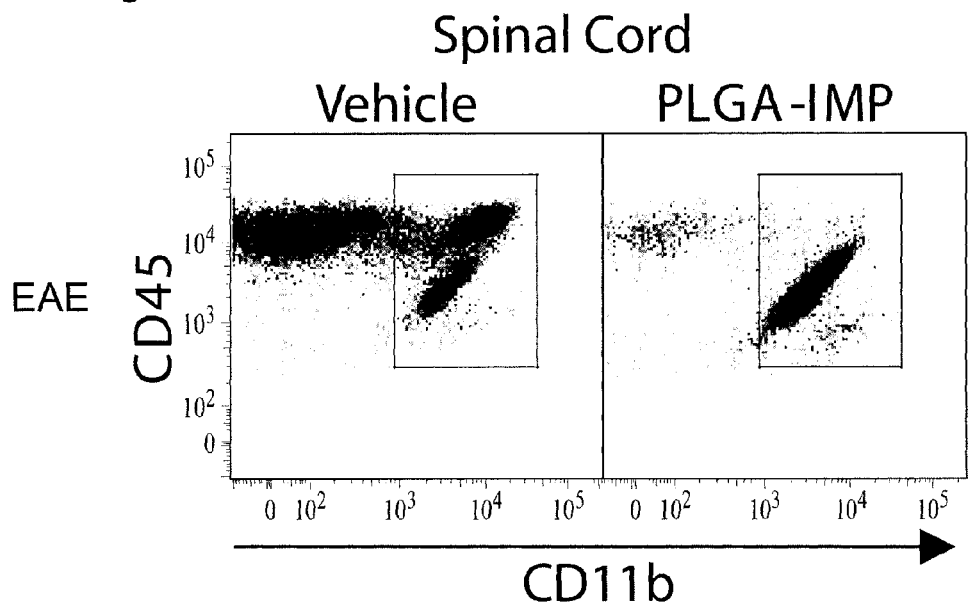
FIG. 8 shows (A-F) IMPs promote accumulation of ΦIM in the spleen during EAE, myocardial infarction and repair of the epithelium in DSS-induced colitis. Significantly reduced infiltration of CD45$^+$ CD11b$^+$ monocyte-derived cells was observed in the day 14 EAE brain following PLGA-IMP infusion (a). The reduction of monocyte-derived cells in the brain corresponded with significant accumulation of ΦIM in the spleens of PLGA-IMP-treated animals, compared to vehicle-treated controls (b). Following myocardial infarction, significant accumulation of ΦIM in the spleen was observed in PLGA-IMP-treated animals, compared to vehicle-treated controls (c, d). Ki67$^+$ immunohistochemical stain of transverse colon on day 9 of DSS challenge (e), compared to H$_2$O control groups, revealed signature Ki67$^+$ staining in the epithelium, with relatively weak staining in DSS-challenged animals (e). Less crypt fallout was observed in DSS-challenged mice treated with PS-IMP (e). Furthermore, in these animals, Ki67$^+$ staining was more frequent and intense in the lamina propria. Image analysis comparing DSS-induced colitis vehicle versus PS-IMP (f) showed that the observed Ki67 differences were statistically significant. EAE data are means±SD and represent three separate experiments with 4-5 mice/group. Cardiac infarction data are representative of 2 experiments with at least 3 mice per group. DSS-colitis data are representative of at least 3 experiments with at least 3 mice per group. Image analysis was performed as described in the Materials and Methods. Statistical analysis was conducted using unpaired, two-tailed Student T tests. P≤0.05 (*), P≤0.01 (), P≤0.001 (*) in comparing PS-IMP and vehicle control group.
Figure 8B:
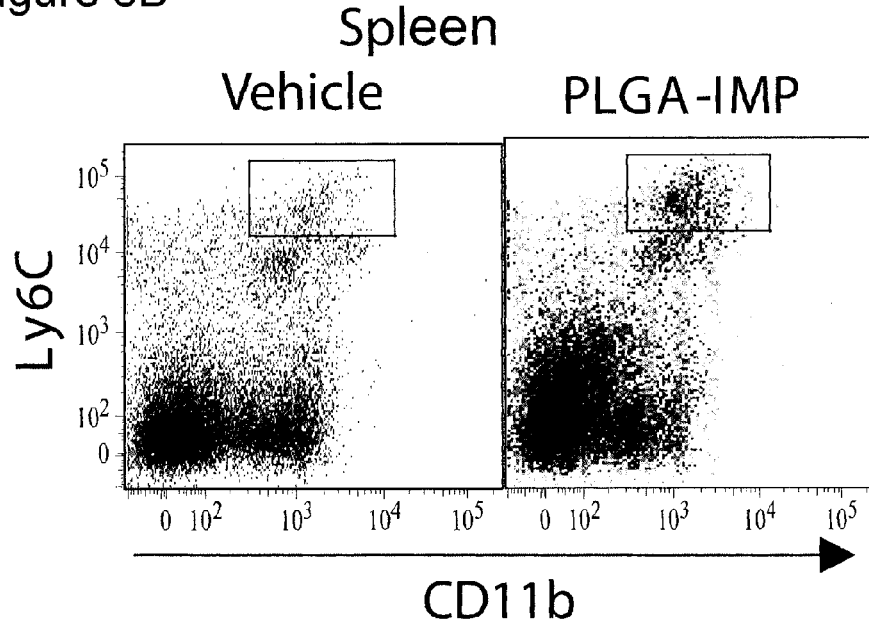

To further understand the therapeutic potential of IMP, a number of non-related inflammatory disease models were examined. Firstly, another non-infectious model of CNS inflammation was tested, namely experimental autoimmune encephalomyelitis (EAE). In EAE circulating $Ly6C^{hi}$ inflammatory monocytes differentiate into macrophages and microglia, in EAE these same cells differentiate predominately into $CD11c^+$ DC that promote T cell activation and epitope spreading (Getts et al., J. Exp. Med. 205:2319-2337, 2007; King et al., Blood 113:3190-3197, 2009; Getts et al., J. Neuroinflammation, In Press). Daily intravenous infusion of biodegradable PLGA-IMP over 7 days at the time of disease onset, both ameliorated disease during treatment and was associated, with a prolonged benefit, as determined by the lack of symptoms for 14 days after treatment cessation (FIG. 5A). More importantly, daily infusion of IMP treatment during primary disease resulted in a reduced disease score and inhibition of relapse initiation, during the treatment period (FIG. 5B). Reduced disease scores in animals treated at onset, correlated with reduced inflammation in the spinal cord, as determined by flow cytometry (FIG. 5C,D and FIG. 8A), with the most striking reduction observed within the inflammatory monocyte-derived DC compartment (FIG. 5C-D and FIG. 8A). Similar to observations in animals suffering WNV encephalitis or peritonitis, the reduction of inflammatory monocytes in the EAE CNS, correlated with a significant accumulation of Ly6C-expressing monocytes in the spleen (FIG. 5D and FIG. 8B).

Example 8

IMP Therapy Reduces Damage Caused by Ischemial Reperfusion

Figure 5H:
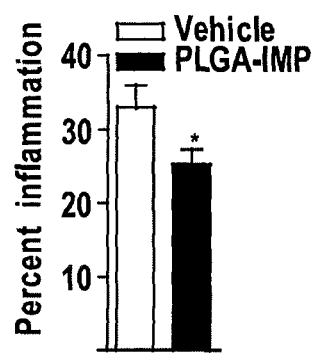
Figure 5I:
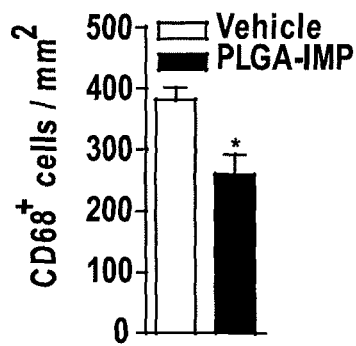
Figure 5J:
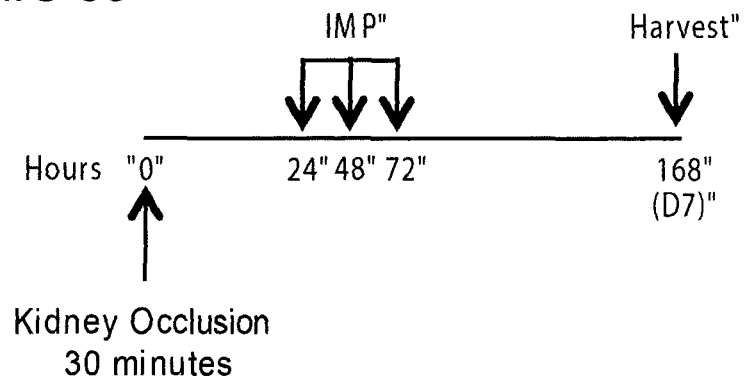
Figure 5K:
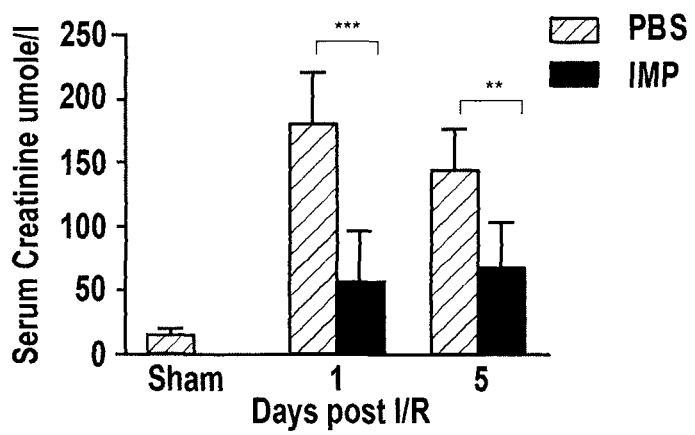
Figure 5L:
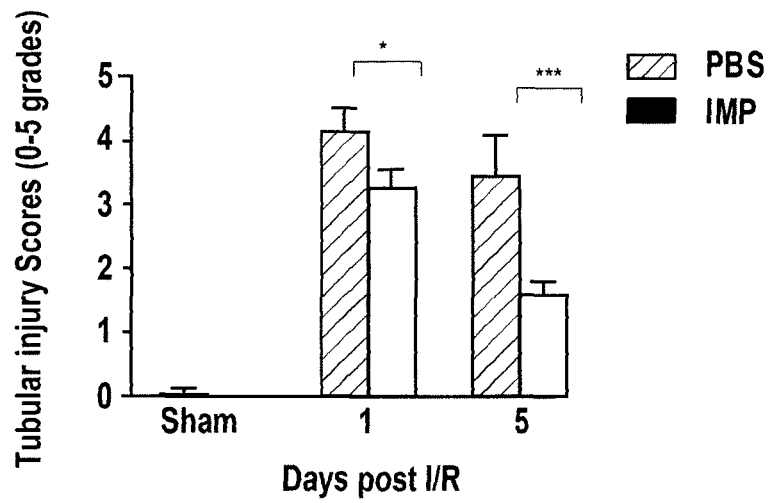
Figure 5M:
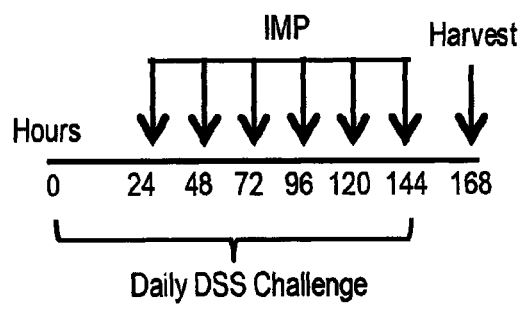
Figure 5N:
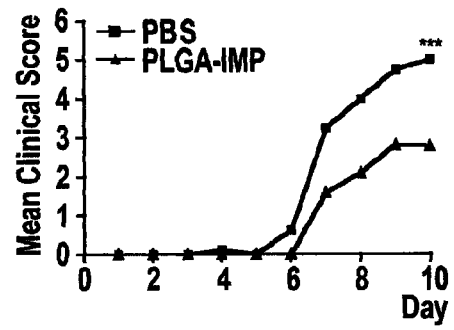
Figure 5O:
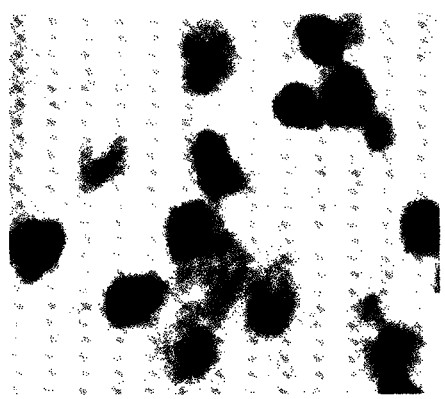
Figure 8D:
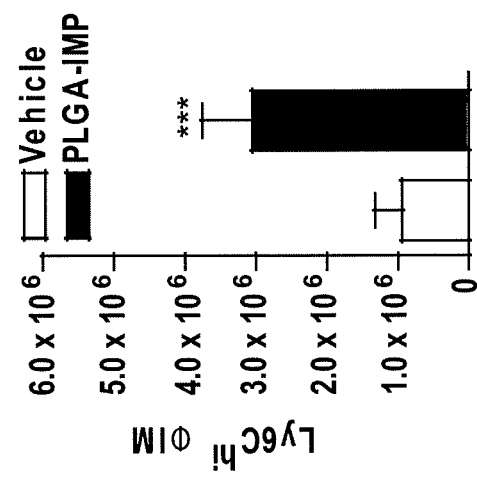
Figure 8C:
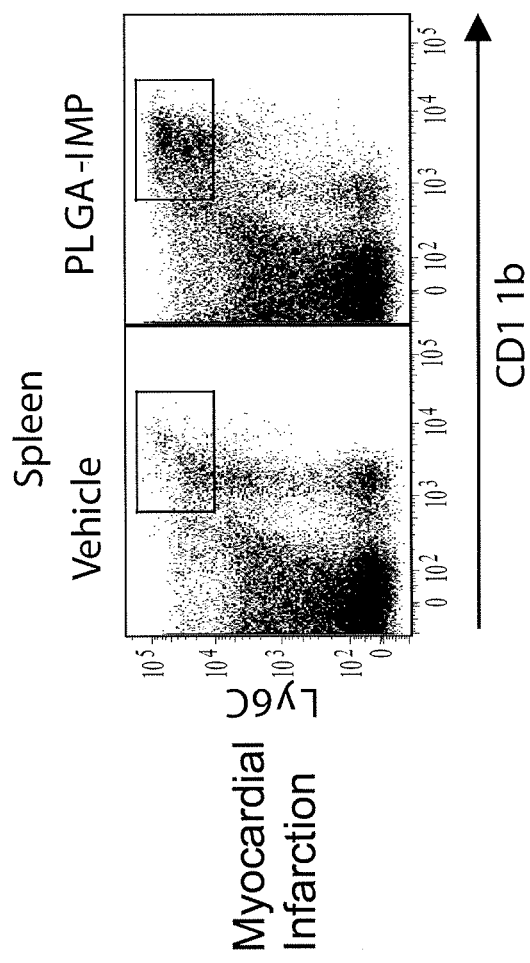
Figure 8F:
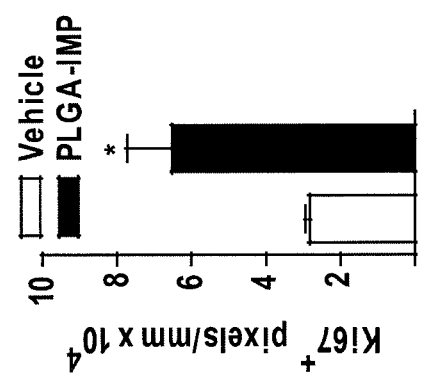
Figure 8E:
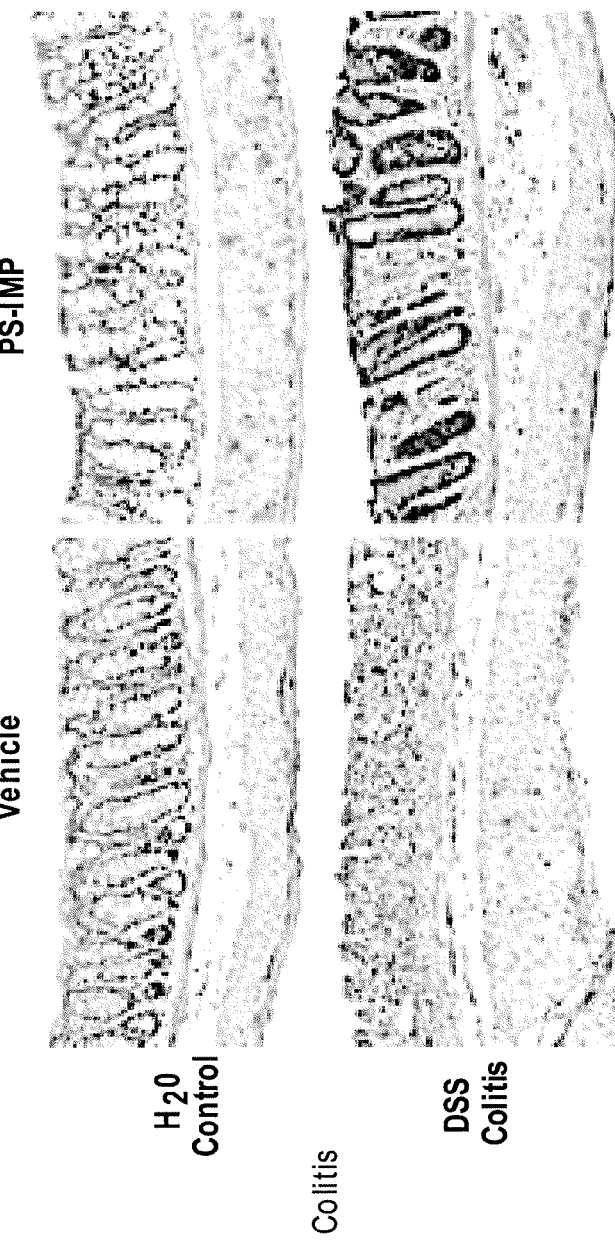

Inflammatory monocytes have been implicated in the pathogenesis of cardiac diseases including atherosclerosis and cardiac infarction, and correlate with poor outcomes (Swirski et al., Science 325:612-616, 02009; Leuschner et al., J. Exp. Med. 209:123-137, 2012; Robbins et al., Circulation 125:364-374, 2012; Bailey et al., Nat. Immunol 8:172-180, 2007). Using the permanent left anterior descending artery occlusion model (Yeap et al., Methods in Molecular Biology, In Press), the impact of 3 days of PLGA-IMP treatment (FIG. 5H) was determined. In vehicle-treated animals, occlusion resulted in a strong monocytic infiltration into the myocardium, with up to 40% of the left ventricular wall involved (FIG. 5I-J). IMP treatment significantly reduced the size of the inflammatory focus, reducing overall cardiac inflammation by 15-20% (FIG. 5O. Furthermore, a significant reduction in $CD68^+$ macrophage numbers within the infarct area was observed, with IMP treatment resulting in a 30% reduction in the number of $CD68^+$ cells/mm², relative to the vehicle-treated control (FIG. 5K,L). Importantly, this reduction again correlated with a significant increase in the number of $Ly6C^{hi}$ inflammatory monocytes in the spleen (FIG. 8D-E). To further address the potential of IMP therapy in reperfusion injury model, IMP were tested in rodents whereby the renal artery was ligated for 45 minutes with blood flow allowed to return there after. IMP treatment was initiated at 12 hours post ligation. Strikingly, serum creatinine clearance was significantly greater in animals that had been treated with IMP compared to vehicle treated controls at day 1 and day 5 (n), correlated with reduced tubular atrophy scores in treated animals at these time points (o). Overall it is well established that graft failure in transplantation as well as long term outcomes after myocardial infarction are directly correlated to the degree of inflammation and infarction size, respectively (Nahrendorf et al., Circulation 121:2437-2445, 2010; Leuschner et al., J. Exp. Med. 209:123-137, 2012; Nahrendorf, et al., J. Exp. Med. 204:3037-3047, 2007). The data here show strong support that IMP not only reduce inflammation, but more importantly are also associated with increased organ function.

Example 9

IMP Therapy Alleviates Symptoms of Inflammatory Bowel Disease

Figure 5P:
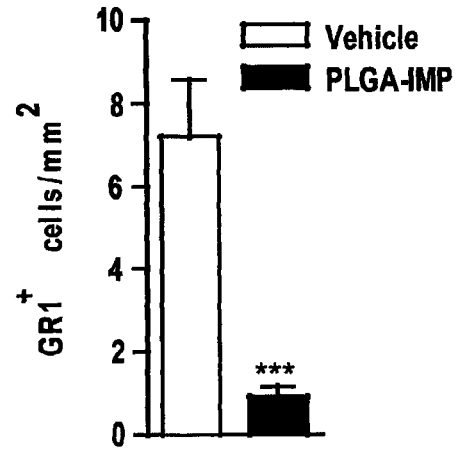
Figure 6A:
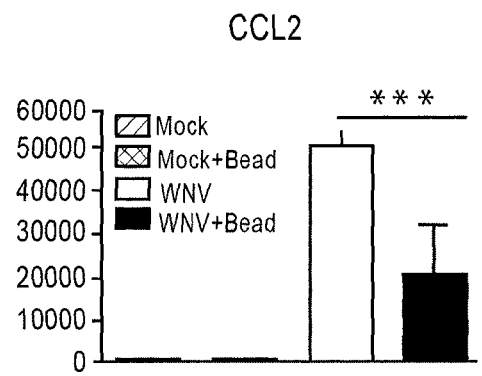
FIG. 6 shows (A-P) IMP treatment significantly reduces inflammatory cytokine levels in the WNV-infected brain. Mock-infected and WNV-infected mice were treated with PS-IMP on day 6 p.i. and brains were isolated and homogenized on day 7 p.i. Cytokine and chemokine levels were analyzed using multiplexed ELISA. Significantly reduced levels of CCL2 (a), IFN-γ (b), IL-6 (c), TNF (d), IL-10 (e), IL-4 CCL3 (g), IL-12 (i), GM-CSF (k), IL-1α (l), IL-9 (n), IL-1β (o) and IL-2 (p) were observed in the brains of WNV-infected animals treated with IMP compared to controls. Levels of IL-3 (h), CCL5 (j) and IL-15 (m) were not significantly reduced with IMP treatment.
Figure 6B:
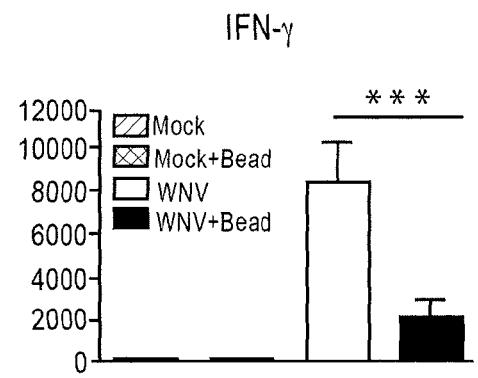
Figure 6C:
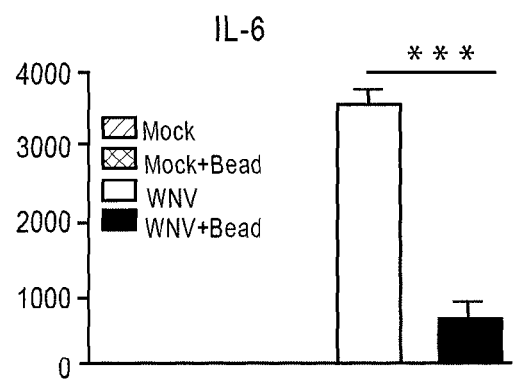
Figure 6D:
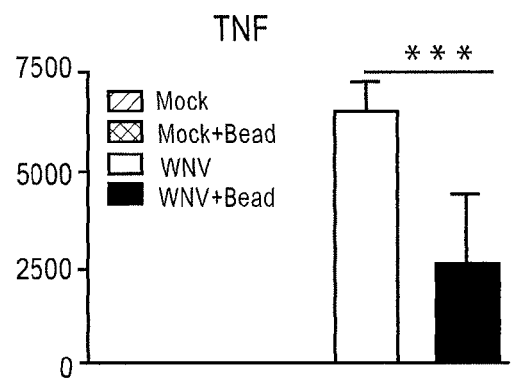
Figure 6E:
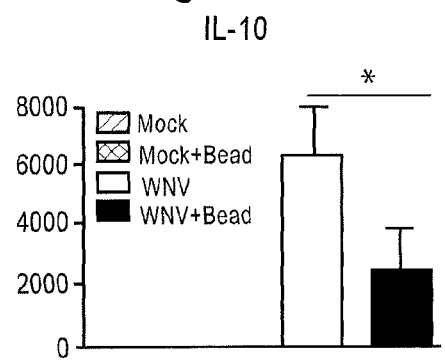
Figure 6F:
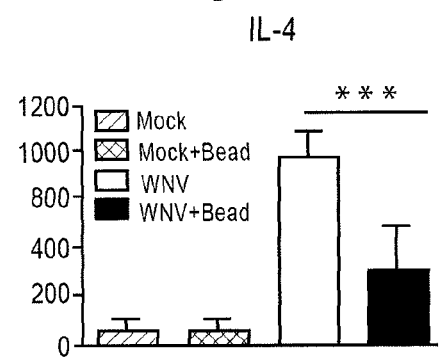
Figure 6G:
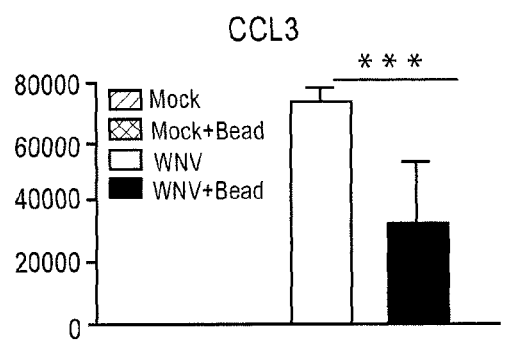
Figure 6H:
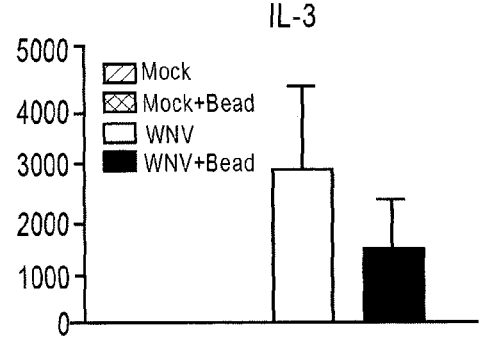
Figure 6I:
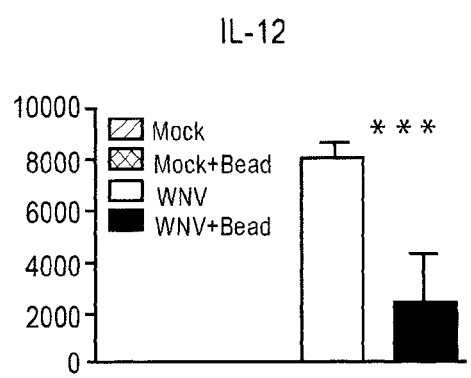
Figure 6J:
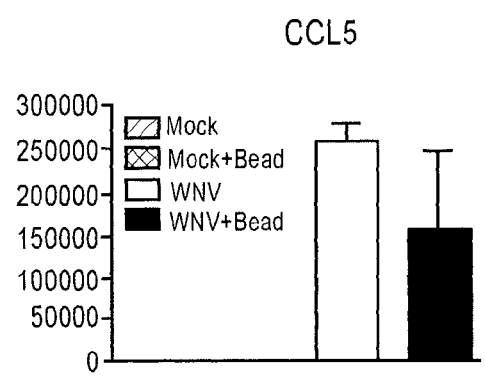
Figure 6K:
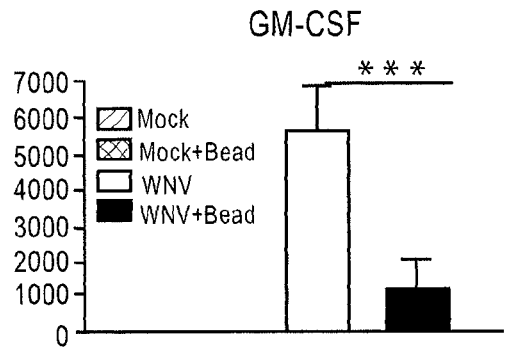
Figure 6L:
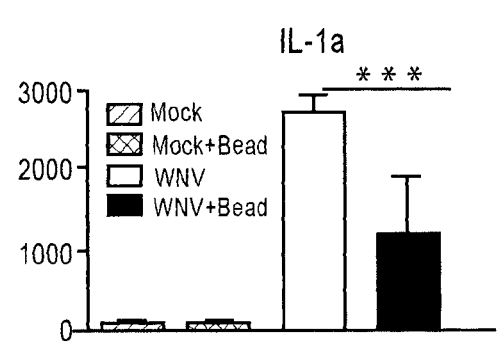
Figure 6M:
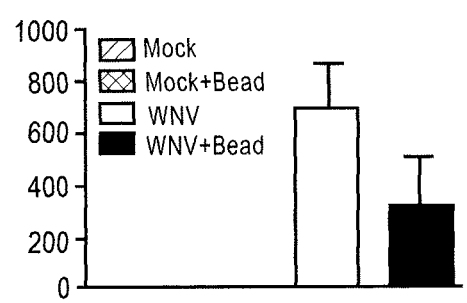
Figure 6N:
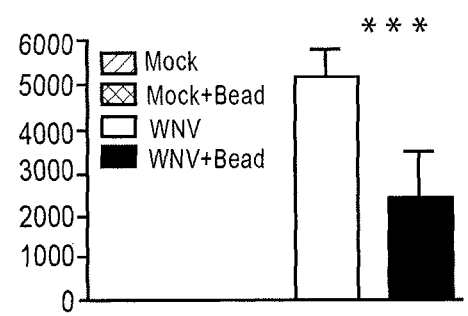
Figure 6O:
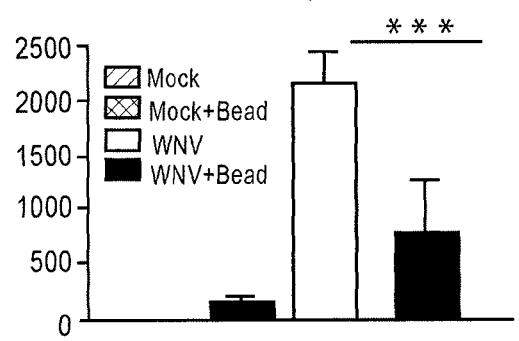
Figure 6P:
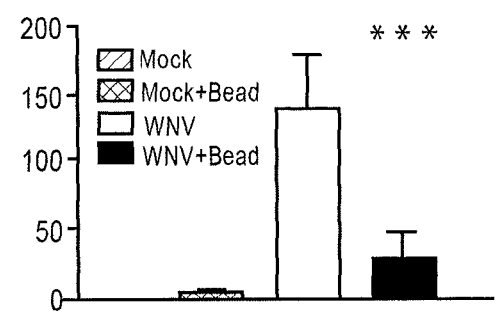
Figure 7A:
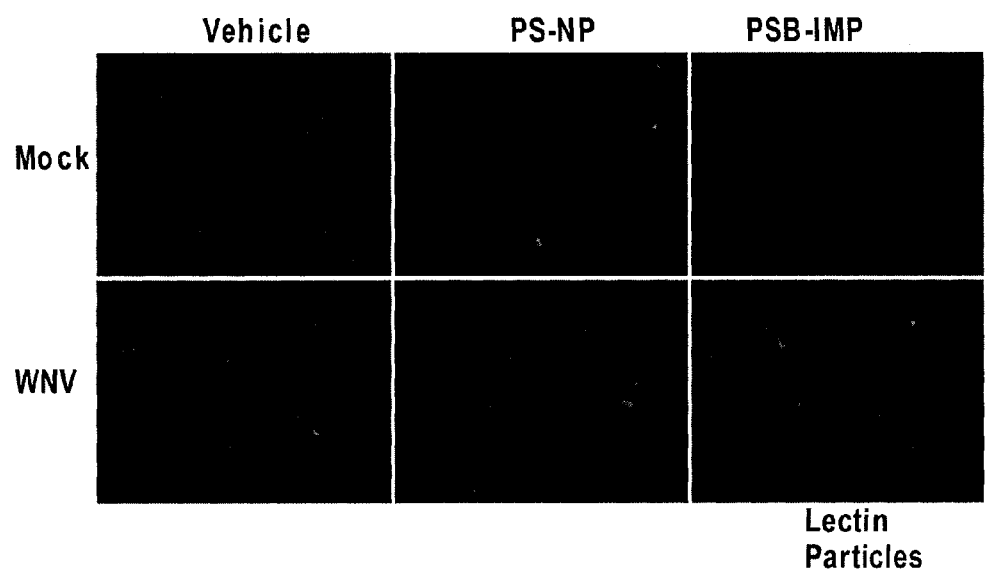
FIG. 7 shows (A-E) few IMPs are found in WNV infected brains, with IMP highly effective in reducing inflammatory monocytes in peritonitis. No Bright-blue NP or PS-IMP could be detected in the D7 p.i. WNV-infected brain by immunohistochemistry after injection on D6 p.i. (a). Similarly, FITC-NP or PS-IMP could not be detected in the WNV-infected brain by flow cytometry (b). PS-IMP were tested in a model of thioglycollate peritonitis in C57BL/6 mice. The infusion of PS-IMP 24 hours after thioglycollate infusion reduced the number of Ly6C$^{hi}$CD11b$^+$ (R3) monocytes isolated from the peritoneum (c, d). This effect was abrogated in splenectomized mice (e). Particle immunohistochemistry and flow cytometry data represent three separate experiments, with at least 3 mice/group. Slides were counterstained with DAPI (blue) to identify cell nuclei. Thioglycollate data are representative of at least 3 experiments with 5 mice per group. Flow cytometry data are means±SD and represent three separate experiments with 4-5 mice/group.
Figure 7B:
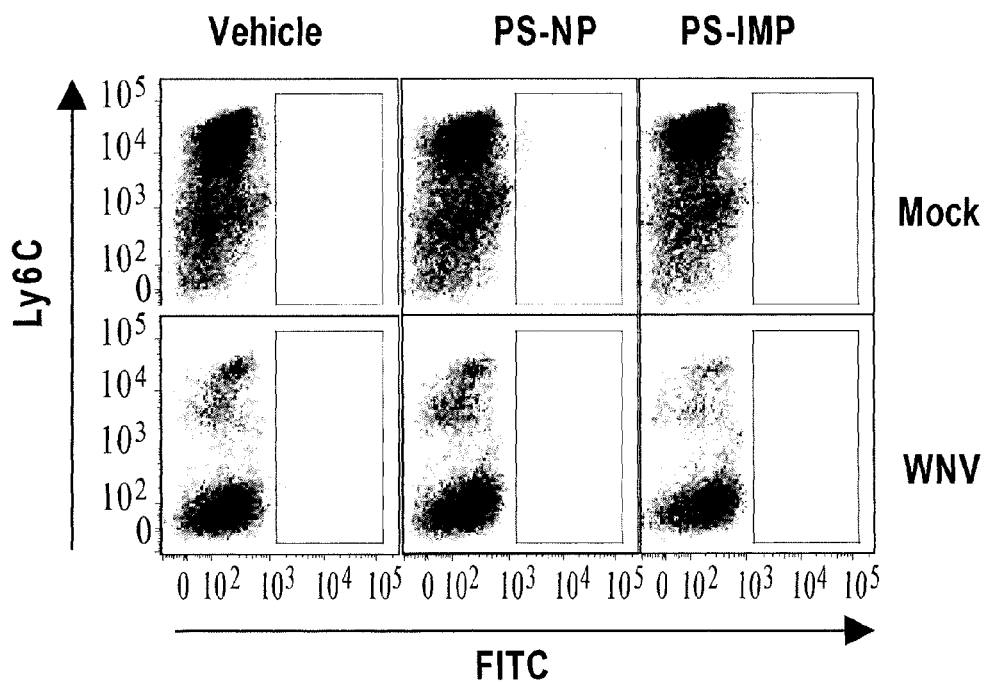
Figure 7C:
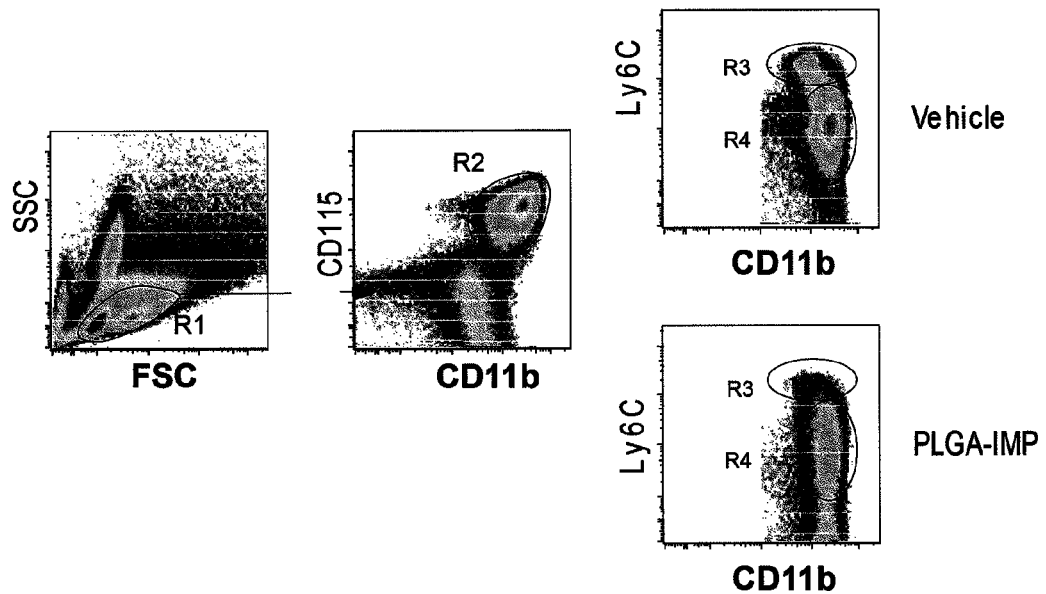
Figure 7D:
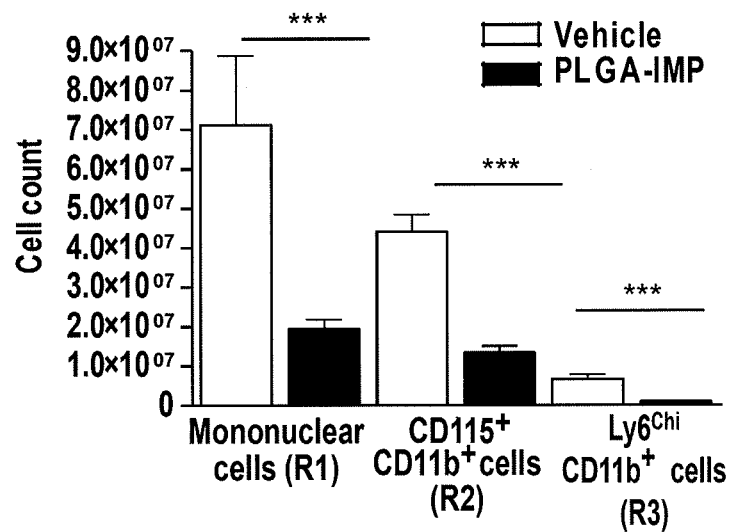
Figure 7E:
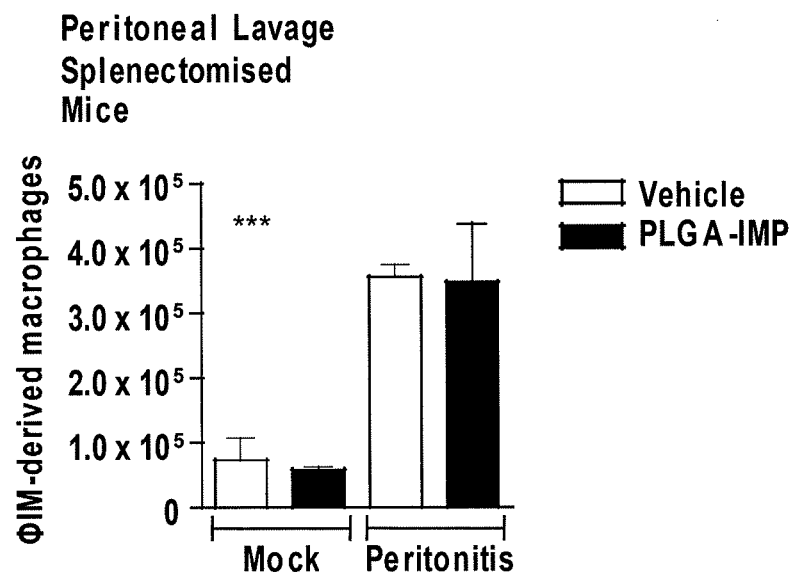

The gut represents a unique organ system, unlike the brain, peritoneum or the heart. The importance of monocytes in inflammatory bowel disease (IBD) has been described (Bain et al., Mucosal Immunol, 2012; Xu et al., Cell Res. 18:1220-1229, 2008), with the chemokine GM CSF as well as $Ly6C^{hi}$ inflammatory monocytes implicated in the pathogenesis of IBD, using a dextran sodium sulphate (DSS)-induced colitis model (Xu et al., Cell Res. 18:1220-1229, 2008). Reduction in $Ly6C^{hi}$ inflammatory monocyte trafficking into the inflamed colon is proposed to reduce disease severity. As such, IMP treatment (FIG. 5P) in animals with DSS-induced colitis was investigated. Colitic symptoms were significantly diminished in animals that were treated with PS-IMP, compared to vehicle controls (FIG. 5G). Furthermore, there was a reduction in the number of $GR1^+$ cells with monocytic morphology into the inflamed colon, as determined by immunohistochemistry (FIG. 5R-S). This correlated with reduced epithelial disruption and significantly increased numbers of epithelial cells labelling with the proliferation marker, Ki67, in PS-IMP-treated animals (FIG. 8F-G). Epithelial proliferation is associated with intestinal recovery following DSS challenge, with the infusion of IMP evidently enabling early repair of DSS-mediated damage.

Example 10

IMP Therapy Protects from Inflammatory Damage in a Myocardial Infarction Model Using the permanent left anterior descending artery occlusion model (Yeap et al., Methods in Molecular Biology, In Press), the impact of 4 days of naked PLGA-IMP treatment (FIG. 9) was determined. In vehicle-treated animals, occlusion resulted in an increase in inflammation. IMP treatment significantly reduced the size of the inflammatory focus, reducing overall cardiac inflammation. Furthermore, a significant reduction in CD68+ macrophage numbers within the infarct area was observed, with IMP treatment resulting in a reduction in the number of CD68+ cells/mm², relative to the vehicle-treated control. Importantly, this reduction area which correlated with a significant increase in the number of Ly6C$^{hi}$ inflammatory monocytes in the spleen.

To further address the potential of IMP therapy in a myocardial ischemia (LAD occlusion)-reperfusion model, IMP were tested in rodents whereby the left anterior descending coronary artery was occluded and then released 30 minutes later. IMP treatment was initiated at 24 hours post ligation and continued for 4 days. As shown in FIG. 10, at 28 days post IR, the infarct scar size in the treated animals was reduced by 45% compared with the PBS-treated animals. Additionally, the systolic ejection fraction in the PLG-IMP treated animals was increased by 21% compared to the control animals.

These data in the preceding examples indicate that IMP can successfully be utilized in a wide variety of infectious and non-infectious inflammatory disorders to reduce inflammatory monocyte trafficking to the site of inflammation. This results in significantly reduced clinical disease symptoms and may also enable repair mechanisms to be initiated, which might otherwise be inhibited by the pro-inflammatory milieu generated by inflammatory monocytes.

Example 11

Preparation of Negatively Charged Immune Modifying Particles (IMPs)

To a solution of Poly(ethylene-maleic anhydride) (PEMA) in D$_2$O (4 mL, 1% w/v) was added dropwise a solution of poly(lactide-co-glycolic acid) (PLG) in dichloromethane (DCM) (2 mL, 20% w/v). The mixture was allowed to sonicate on ice at 16 watts for 30 sec using the VC 30 Ultrasonic Processor. The resulting homogenized crude was then poured into a solution of D$_2$O (200 mL containing 0.5% w/v of PEMA). The homogenized slurry was allowed to stir overnight at speed setting of 3.5 using Bellco Glass, Inc., Bellstir Multi-stir 9 magnetic stirrer (10 W for 10 s, 16 W for 10 s, 16 W for 30 s).

Results

After three hours of stirring, particle size analyses were performed using dynamic light scattering in disposable polystyrene cuvettes
  a. 10 W, 10 s–Z-average=499.9 nm–PdI=0.23, Peak=634.5 nm
  b. 16 W, 10 s–Z-average=528.9 nm–PdI=0.227, Peak=657.5 nm
  c. 16 W, 30 s–Z-average=471.6 nm–PdI=0.228, Peak=580.5 nm
  d. 16 W, 60 s–Z-average=491.1 nm–PdI=0.275, Peak=600.8 nm After the reaction was complete, the resulting crude suspension was then purified.

Purification

Fresh D$_2$O and 10× sodium bicarbonate buffer were chilled overnight to 4° C. Using a 40 μm cell strainer, 36 mL of particle suspension were filtered from each batch into an appropriately-labelled 50 mL centrifuge tube containing 4 mL chilled 10× sodium bicarbonate buffer. Each beaker produced approximately 6 such tubes. All tubes were centrifuged for about 15 minutes at 7000 g at 4° C. and the supernatant was aspirated. Preparation of the suspension was repeated using the above-mentioned procedure and much of the particle pellets were suspended as possible in 1 mL chilled D$_2$O.

The resuspended particles were transferred into a fresh tube with 4 mL of chilled 10× sodium bicarbonate buffer. (Step 1)

Resuspension of the particle was repeated until the entire particle pellets haves been successfully resuspended. (Step 2)

The 6 centrifugal tubes were then combined into one centrifuge tube (50 mL tube) and the tube was filled with the remaining volume to 40 mL of chilled D$_2$O (Wash 1).

The tube was centrifuged for 20 minutes at 7000 g at 4° C. and the supernatant was aspirated.

Step 1 and 2 and Wash 1 of the resulting particle were repeated each time at least two more times. Finally, the resulting particle pellets were then subjected to a flash-freeze in liquid nitrogen and lyophilized to dryness in the manifold to obtain negatively IMPs.

FIG. 14 shows characterization of surface-functionalized poly(lactide-co-glycolide) particles by dynamic light scattering analysis. Surface-functionalized poly(lactide-co-glycolide) particles were analysed on a Malvern Zetasizer Nano ZS (Malvern Instruments, Westborough, Mass.) at a count rate of 2.5×10$^5$ counts per second in 18.2 MΩ water. The population of surface-functionalized poly(lactide-co-glycolide) particles had a Z-average diameter of 567 nm, a peak diameter of 670 nm and a polydispersity index of 0.209.

Table 4 shows the measurements for surface functionalized PLG-PEMA particles. The data in the table is representative, as each batch is slightly different. The numbers in the table were based on combining several batches of particles though. The measurements for the double emulsion particles are similar to those in Table 3.

TABLE 4

Measurements for the surface functionalized PLG-PEMA particles

| Particle | Z-average size by intensity (nm) | ζ-potential (mV) |
|---|---|---|
| PLG (Phosphorex) | 624.3 | −32.7 ± 4.71 |
| PLG-PEMA | 429.9 | −67.4 ± 10.9 |

Example 12

IMP Induce Regulatory T Cells

Previously, it has been shown that IMP infusion in the MS model, experimental autoimmune encephalomyelitis can inhibit disease. In this model, at day 0, mice are immunized with complete fruends adjuvant and the myelin antigen, proteolipid protein 139-158. Disease symptoms are monitored daily, and when disease onset is evident, IMP treatment for 10 days is conducted. In this example, daily intravenous infusion of biodegradable PLGA-IMP over 10 days from the time of disease onset, both ameliorated disease during treatment and was associated with a post treatment period of 14 days devoid of symptoms (FIG. 15A). Reduced disease scores in animals treated at onset, correlated with increased numbers of C4+CD25+FOXP3+TIM3+ regulatory T cells during treatment (FIGS. 15B and C). At day 20 (10 past treatment initiation), these Tregs express the negative co-stimulatory molecule PD-1 (FIG. 15 B). 10 days post dosing cessation, the number of Tregs was found to be diminished to baseline, which correlated with relapse of disease (FIG. 15A).

Example 13

IMPs Bind to Distinct Proteins in Inflammatory Blood Compared to Naïve Blood

Mouse plasma was collected by cardiac puncture into hepinarized tubes from Wets Nile Infected or Mock (non-infected) mice. Plasma was subsequently separated from other blood components (eg white and red blood cells) by standard methods well known in the art. Plasma was subsequently incubated with $3\times10^8$ immune modifying nanoparticles for 30 minutes at room temperature. After 30 minutes particles were washed and proteins were separated on SDS-PAGE gels and each lane cut into 12 equal gel slices. Slices were subjected to trypsin digest and the resulting peptide mixtures analyzed by reversed phase liquid chromatography coupled to tandem mass spectrometry (LC-MS/MS. Proteins were subject to GeLC-MS analysis. Briefly, proteins were reduced and alkylated in the presence of dithiothreitol and iodoacetamide. Bands were dried by vacuum centrifugation and incubated with 240 ng trypsin for 1 hour at 4° C. Excess trypsin was removed and replaced with 50 mM ammonium bicarbonate for incubation at 37° C. overnight. Prior to mass spectrometric analysis peptides were concentrated and desalted with the use of pre-fabricated micro-columns containing Poros R2 resin (Perseptive Biosystems, Framingham Mass.). Peptides eluted were resolublized in 0.1% formic acid and subject to reverse phase LC-MS/MS. Approximately 41,000 MS/MS spectra were generated from replicate LC-MS/MS experiments. Tandem mass spectra were extracted, charge state deconvoluted and deisotoped in Mascot and analyzed using Mascot and X!Tandem. Data were searched against *Mus musculus* (mouse) entries included in the SWISS-PROT databases with the significance threshold set at p<0.05. Searches were conducted with a fragment ion mass tolerance of 15 ppm and a parent ion tolerance of 0.2 Da. Methionine sulfoxide, carbamidomethyl-cysteine and deamidated asparagine and glutamine were specified as variable modifications. Scaffold was used integrate multiple MS/MS experiments and validate MS/MS based peptides and protein identifications. Peptides were considered only if Mascot ion scores exceeded 30, 40 and 40 for doubly, triply and quadruply charged peptides respectively. X!Tandem identifications required −Log (Expect scores) scores greater than 2.0. Protein identifications were accepted if a minimum of 2 peptides were identified matching the above criteria. Five proteins were considered identified although only matching one peptide. In this case, the peptides were sequenced on multiple occasions and sequence coverage obtained by the single peptide was greater than 5%.

The results of these studies identified the following proteins bound to particles incubated with naïve serum:

TABLE 5

Proteins that bind IMP in naïve serum

| Identified Proteins | SWISSProt Accession Number | Gene Name | pI | Molecular Weight | Unique Peptides Identified | % Sequence Coverage |
|---|---|---|---|---|---|---|
| 14-3-3 protein zeta/delta | 1433Z_MOUSE | Ywhaz | 4.73 | 28 kDa | 3 | 12% |
| Protein 4.1 | 41_MOUSE | Epb41 | 5.43 | 96 kDa | 4 | 6.10% |
| Alpha-1-antitrypsin 1-1 | A1AT1_MOUSE | Serpina1a | 5.44 | 46 kDa | 3 | 4.60% |
| Actin, cytoplasmic 1 | ACTB_MOUSE | Actb | 5.29 | 42 kDa | 11 | 39% |
| Alpha-actinin-1 | ACTN1_MOUSE | Actn1 | 5.23 | 103 kDa | 2 | 2.50% |
| Alpha-adducin | ADDA_MOUSE | Add1 | 5.62 | 81 kDa | 2 | 3.10% |
| ADP/ATP translocase 1 | ADT1_MOUSE | Slc25a4 | 9.73 | 33 kDa | 2 | 8.10% |
| Serum albumin | ALBU_MOUSE | Alb | 5.53 | 69 kDa | 14 | 29% |
| Ankyrin-1 | ANK1_MOUSE | Ank1 | 6.09 | 204 kDa | 5 | 3.30% |
| Annexin A2 | ANXA2_MOUSE | Anxa2 | 7.53 | 39 kDa | 6 | 20% |
| Annexin A5 | ANXA5_MOUSE | Anxa5 | 4.82 | 36 kDa | 3 | 9.40% |
| Acylamino-acid-releasing enzyme | APEH_MOUSE | Apeh | 5.36 | 82 kDa | 4 | 6.10% |
| Apolipoprotein A-I | APOA1_MOUSE | Apoa1 | 5.31 | 31 kDa | 6 | 21% |
| Apolipoprotein A-IV | APOA4_MOUSE | Apoa4 | 5.21 | 45 kDa | 2 | 7.10% |
| Apolipoprotein C-IV | APOC4_MOUSE | Apoc4 | 9.23 | 14 kDa | 2 | 16% |
| Apolipoprotein E | APOE_MOUSE | Apoe | 5.46 | 36 kDa | 12 | 38% |
| Beta-2-glycoprotein 1 | APOH_MOUSE | Apoh | 8.62 | 39 kDa | 5 | 19% |
| Sodium/potassium-transporting ATPase subunit alpha-1 | AT1A1_MOUSE | Atp1a1 | 5.27 | 113 kDa | 5 | 5.80% |
| Sarcoplasmic/endoplasmic reticulum calcium ATPase 1 | AT2A1_MOUSE | Atp2a1 | 5.13 | 109 kDa | 8 | 10% |
| ATP synthase subunit alpha, mitochondrial | ATPA_MOUSE | Atp5a1 | 8.28 | 60 kDa | 6 | 13% |
| ATP synthase subunit beta, mitochondrial | ATPB_MOUSE | Atp5b | 4.99 | 56 kDa | 7 | 19% |
| Band 3 anion transport protein | B3AT_MOUSE | Slc4a1 | 5.31 | 103 kDa | 11 | 16% |
| Flavin reductase (NADPH) | BLVRB_MOUSE | Blvrb | 6.47 | 22 kDa | 6 | 46% |

TABLE 5-continued

Proteins that bind IMP in naïve serum

| Identified Proteins | SWISSProt Accession Number | Gene Name | pI | Molecular Weight | Unique Peptides Identified | % Sequence Coverage |
|---|---|---|---|---|---|---|
| Complement C1q subcomponent subunit A | C1QA_MOUSE | C1qa | 9.48 | 26 kDa | 4 | 21% |
| Complement C1q subcomponent subunit B | C1QB_MOUSE | C1qb | 8.34 | 27 kDa | 6 | 27% |
| Complement C1q subcomponent subunit C | C1QC_MOUSE | C1qc | 8.88 | 26 kDa | 4 | 16% |
| C-1-tetrahydrofolate synthase, cytoplasmic | C1TC_MOUSE | Mthfd1 | 6.73 | 101 kDa | 4 | 5.50% |
| C4b-binding protein | C4BPA_MOUSE | C4bpa | 5.97 | 52 kDa | 4 | 12% |
| Carbonic anhydrase 1 | CAH1_MOUSE | Ca1 | 6.47 | 28 kDa | 4 | 20% |
| Carbonic anhydrase 2 | CAH2_MOUSE | Ca2 | 6.48 | 29 kDa | 6 | 37% |
| Catalase | CATA_MOUSE | Cat | 7.72 | 60 kDa | 7 | 17% |
| Clathrin heavy chain 1 | CLH1_MOUSE | Cltc | 5.48 | 192 kDa | 8 | 6.20% |
| Complement C3 | CO3_MOUSE | C3 | 6.3 | 186 kDa | 30 | 22% |
| Cofilin-1 | COF1_MOUSE | Cfl1 | 8.26 | 19 kDa | 1 | 6.60% |
| Uroporphyrinogen decarboxylase | DCUP_MOUSE | Urod | 6.21 | 41 kDa | 3 | 9.00% |
| Desmoplakin | DESP_MOUSE | Dsp | 6.43 | 333 kDa | 2 | 0.80% |
| Elongation factor 1-alpha 1 | EF1A1_MOUSE | Eef1a1 | 9.1 | 50 kDa | 6 | 16% |
| Elongation factor 1-delta | EF1D_MOUSE | Eef1d | 4.91 | 31 kDa | 2 | 8.50% |
| Elongation factor 2 | EF2_MOUSE | Eef2 | 6.42 | 95 kDa | 4 | 4.50% |
| 55 kDa erythrocyte membrane protein | EM55_MOUSE | Mpp1 | 6.72 | 52 kDa | 3 | 7.50% |
| Alpha-enolase | ENOA_MOUSE | Eno1 | 6.36 | 47 kDa | 2 | 9.70% |
| Endoplasmin | ENPL_MOUSE | Hsp90b1 | 4.72 | 92 kDa | 3 | 5.50% |
| Erythrocyte membrane protein band 4.2 | EPB42_MOUSE | Epb42 | 6.98 | 77 kDa | 2 | 3.30% |
| Ezrin | EZRI_MOUSE | Ezr | 5.83 | 69 kDa | 6 | 10% |
| Coagulation factor V | FA5_MOUSE | F5 | 5.66 | 247 kDa | 4 | 2.60% |
| Alpha-2-HS-glycoprotein | FETUA_MOUSE | Ahsg | 5.94 | 37 kDa | 2 | 9.90% |
| Fibrinogen beta chain | FIBB_MOUSE | Fgb | 3.53 | 55 kDa | 13 | 35% |
| Fibrinogen gamma chain | FIBG_MOUSE | Fgg | 5.55 | 49 kDa | 13 | 34% |
| Fibronectin | FINC_MOUSE | Fn1 | 5.3 | 272 kDa | 31 | 17% |
| Filamin-A | FLNA_MOUSE | Flna | 5.68 | 281 kDa | 15 | 7.50% |
| Glyceraldehyde-3-phosphate dehydrogenase | G3P_MOUSE | Gapdh | 8.45 | 36 kDa | 9 | 37% |
| Gelsolin | GELS_MOUSE | Gsn | 5.72 | 86 kDa | 4 | 8.60% |
| Glutathione peroxidase 3 | GPX3_MOUSE | Gpx3 | 6.38 | 25 kDa | 3 | 18% |
| Histone H2B type 1-B | H2B1B_MOUSE | Hist1h2bb | 10.32 | 14 kDa | 1 | 7.10% |
| H-2 class I histocompatibility antigen, Q10 alpha chain | HA10_MOUSE | H2-Q10 | 5.06 | 37 kDa | 2 | 6.20% |
| Hemoglobin subunit alpha | HBA_MOUSE | Hba | 8.08 | 15 kDa | 6 | 43% |
| Hemoglobin subunit beta-1 | HBB1_MOUSE | Hbb-b1 | 7.26 | 16 kDa | 10 | 74% |
| Delta-aminolevulinic acid dehydratase | HEM2_MOUSE | Alad | 6.31 | 36 kDa | 2 | 6.40% |
| Coproporphyrinogen-III oxidase, mitochondrial | HEM6_MOUSE | Cpox | 6.47 | 50 kDa | 3 | 7.00% |
| Hemopexin | HEMO_MOUSE | Hpx | 7.58 | 51 kDa | 2 | 4.30% |
| Histidine-rich glycoprotein | HRG_MOUSE | Hrg | 7.28 | 59 kDa | 5 | 11% |
| Heat shock protein HSP 90-alpha | HS90A_MOUSE | Hsp90aa1 | 4.93 | 85 kDa | 2 | 4.10% |
| Heat shock protein HSP 90-beta | HS90B_MOUSE | Hsp90ab1 | 4.97 | 83 kDa | 6 | 8.40% |
| Heat shock cognate 71 kDa protein | HSP7C_MOUSE | Hspa8 | 5.37 | 71 kDa | 13 | 24% |
| Eukaryotic initiation factor 4A-I | IF4A1_MOUSE | Eif4a1 | 5.32 | 46 kDa | 2 | 5.70% |
| Ig mu chain C region secreted form | IGHM_MOUSE | Igh-6 | 6.56 | 50 kDa | 13 | 38% |
| Ig kappa chain C region | IGKC_MOUSE | n/a | 5.56 | 11 kDa | 3 | 31% |
| Ubiquitin-like protein ISG15 | ISG15_MOUSE | Isg15 | 8.61 | 18 kDa | 1 | 5.60% |

TABLE 5-continued

Proteins that bind IMP in naïve serum

| Identified Proteins | SWISSProt Accession Number | Gene Name | pI | Molecular Weight | Unique Peptides Identified | % Sequence Coverage |
|---|---|---|---|---|---|---|
| Integrin alpha-IIb | ITA2B_MOUSE | Itga2b | 5.43 | 113 kDa | 6 | 8.70% |
| Integrin beta-3 | ITB3_MOUSE | Itgb3 | 5.07 | 87 kDa | 2 | 3.40% |
| Inter alpha-trypsin inhibitor, heavy chain 4 | ITIH4_MOUSE | Itih4 | 5.91 | 105 kDa | 3 | 0.00% |
| Kininogen-1 | KNG1_MOUSE | Kng1 | 6.02 | 73 kDa | 4 | 9.70% |
| Pyruvate kinase isozymes M1/M2 | KPYM_MOUSE | Pkm2 | 7.42 | 58 kDa | 2 | 3.80% |
| L-lactate dehydrogenase A chain | LDHA_MOUSE | Ldha | 7.76 | 36 kDa | 3 | 9.00% |
| Mannose-binding protein C | MBL2_MOUSE | Mbl2 | 4.94 | 26 kDa | 2 | 9.40% |
| Malate dehydrogenase, mitochondrial | MDHM_MOUSE | Mdh2 | 8.55 | 36 kDa | 5 | 18% |
| Myosin regulatory light chain 12B | ML12B_MOUSE | Myl12b | 4.69 | 20 kDa | 4 | 24% |
| Major vault protein | MVP_MOUSE | Mvp | 5.43 | 96 kDa | 5 | 7.80% |
| Myosin-10 | MYH10_MOUSE | Myh10 | 5.43 | 229 kDa | 2 | 3.00% |
| Myosin-9 | MYH9_MOUSE | Myh9 | 5.54 | 226 kDa | 34 | 21% |
| Myosin light polypeptide 6 | MYL6_MOUSE | Myl6 | 4.56 | 17 kDa | 3 | 20% |
| Dihydrolipoyllysine-residue acetyltransferase component of pyruvate dehydrogenase complex | ODP2_MOUSE | Dlat | 5.7 | 68 kDa | 2 | 5.10% |
| Protein disulfide-isomerase A3 | PDIA3_MOUSE | Pdia3 | 5.69 | 57 kDa | 3 | 6.10% |
| Plasminogen | PLMN_MOUSE | Plg | 6.18 | 91 kDa | 10 | 20% |
| Purine nucleoside phosphorylase | PNPH_MOUSE | Pnp | 5.78 | 32 kDa | 6 | 25% |
| Peptidyl-prolyl cis-trans isomerase A | PPIA_MOUSE | Ppia | 7.88 | 18 kDa | 3 | 22% |
| Peroxiredoxin-1 | PRDX1_MOUSE | Prdx1 | 8.26 | 22 kDa | 1 | 5.50% |
| Peroxiredoxin-2 | PRDX2_MOUSE | Prdx2 | 5.2 | 22 kDa | 6 | 32% |
| Peroxiredoxin-6 | PRDX6_MOUSE | Prdx6 | 5.72 | 25 kDa | 3 | 15% |
| GTP-binding nuclear protein Ran | RAN_MOUSE | Ran | 7.2 | 24 kDa | 2 | 9.70% |
| Ras-related protein Rap-1b | RAP1B_MOUSE | Rap1b | 5.65 | 21 kDa | 1 | 5.40% |
| Ubiquitin-60S ribosomal protein L40 | RL40_MOUSE | Uba52 | 6.56 | 15 kDa | 3 | 27% |
| 60S acidic ribosomal protein P0 | RLA0_MOUSE | Rplp0 | 5.91 | 34 kDa | 4 | 20% |
| 40S ribosomal protein SA | RSSA_MOUSE | Rpsa | 4.8 | 33 kDa | 2 | 11% |
| Selenium-binding protein 1 | SBP1_MOUSE | Selenbp1 | 5.87 | 53 kDa | 3 | 6.60% |
| Spectrin alpha chain, erythrocyte | SPTA1_MOUSE | Spta1 | 4.94 | 280 kDa | 19 | 9.60% |
| Spectrin beta chain, erythrocyte | SPTB1_MOUSE | Sptb | 5.19 | 245 kDa | 14 | 8.10% |
| Transgelin-2 | TAGL2_MOUSE | Tagln2 | 8.44 | 22 kDa | 2 | 11% |
| Tubulin alpha-1B chain | TBA1C_MOUSE | Tuba1b | 4.96 | 50 kDa | 9 | 27% |
| Tubulin alpha-4A chain | TBA4A_MOUSE | Tuba4a | 4.93 | 50 kDa | 2 | 21% |
| Tubulin beta-1 chain | TBB1_MOUSE | Tubb1 | 4.96 | 50 kDa | 3 | 15% |
| Tubulin beta-4B chain | TBB4B_MOUSE | Tubb4b | 4.79 | 50 kDa | 11 | 30% |
| Tubulin beta-5 chain | TBB5_MOUSE | Tubb5 | 4.78 | 50 kDa | 2 | 24% |
| Transitional endoplasmic reticulum ATPase | TERA_MOUSE | Vcp | 5.14 | 89 kDa | 4 | 6.20% |
| Transferrin receptor protein 1 | TFR1_MOUSE | Tfrc | 6.13 | 86 kDa | 11 | 18% |
| Talin-1 | TLN1_MOUSE | Tln1 | 5.84 | 270 kDa | 16 | 8.20% |
| Serotransferrin | TRFE_MOUSE | Tf | 6.81 | 77 kDa | 3 | 4.60% |
| Thrombospondin-1 | TSP1_MOUSE | Thbs1 | 4.71 | 130 kDa | 3 | 2.60% |
| Ubiquitin-like modifier-activating enzyme 1 | UBA1_MOUSE | Uba1 | 5.43 | 118 kDa | 2 | 3.10% |

TABLE 5-continued

Proteins that bind IMP in naïve serum

| Identified Proteins | SWISSProt Accession Number | Gene Name | pI | Molecular Weight | Unique Peptides Identified | % Sequence Coverage |
|---|---|---|---|---|---|---|
| Ubiquitin-conjugating enzyme E2 O | UBE2O_MOUSE | Ube2o | 4.94 | 141 kDa | 3 | 3.50% |
| Fermitin family homolog 3 | URP2_MOUSE | Fermt3 | 6.6 | 76 kDa | 4 | 8.10% |
| Vinculin | VINC_MOUSE | Vcl | 5.77 | 117 kDa | 10 | 11% |
| Vitronectin | VTNC_MOUSE | Vtn | 5.56 | 55 kDa | 7 | 17% |

Interestingly, however, these methods identified 15 unique proteins that bind to IMP under inflammatory conditions that are not found bound to IMP under non-inflammatory or naïve conditions. Those proteins are listed in Table 6.

TABLE 6

Proteins that bind IMP in inflammatory serum only

| Unique Protein | Accession Number |
|---|---|
| Actin, muscle - *Pisaster ochraceus* (Sea star) | ACTM_PISOC |
| Annexin A1 (Annexin I) (Lipocortin I) (Calpactin II) (Chromobindin-9) (p35) (Phospholipase A2 inhibitory protein) - *Homo sapiens* (Human) | ANXA1_HUMAN (+1) |
| ATP synthase subunit beta, mitochondrial precursor (EC 3.6.3.14) - *Schizosaccharomyces pombe* (Fission yeast) | ATPB_SCHPO |
| Fatty acid-binding protein, epidermal (E-FABP) (Psoriasis-associated fatty acid-binding protein homolog) (PA-FABP) - *Homo sapiens* (Human) | FABPE_HUMAN |
| Filaggrin - *Homo sapiens* (Human) | FILA_HUMAN |
| Heat-shock protein beta-1 (HspB1) (Heat shock 27 kDa protein) (HSP 27) (Stress-responsive protein 27) (SRP27) (Estrogen-regulated 24 kDa protein) (28 kDa heat shock protein) - *Homo sapiens* (Human) | HSPB1_HUMAN |
| Histone H2A type 1-B - *Homo sapiens* (Human) | H2A1B_HUMAN (+36) |
| Junction plakoglobin (Desmoplakin-3) (Desmoplakin III) - *Bos taurus* (Bovine) | PLAK_BOVIN (+3) |
| Parotid secretory protein precursor (PSP) - *Mus musculus* (Mouse) | PSP_MOUSE |
| Protein S100-A11 (S100 calcium-binding protein A11) (Protein S100C) (Calgizzarin) (MLN 70) - *Homo sapiens* (Human) | S10AB_HUMAN (+3) |
| Protein S100-A7 (S100 calcium-binding protein A7) (Psoriasin) - *Homo sapiens* (Human) | S10A7_HUMAN |
| Protein S100-A8 (S100 calcium-binding protein A8) (Calgranulin-A) (Migration inhibitory factor-related protein 8) (MRP-8) (Cystic fibrosis antigen) (CFAG) (P8) (Leukocyte L1 complex light chain) (Calprotectin L1L subunit) (Urinary stone protein band A) - *Homo sapiens* (Human) | S10A8_HUMAN |
| Protein S100-A9 (S100 calcium-binding protein A9) (Calgranulin-B) (Migration inhibitory factor-related protein 14) (MRP-14) (P14) (Leukocyte L1 complex heavy chain) (Calprotectin L1H subunit) - *Homo sapiens* (Human) | S10A9_HUMAN |
| Serum albumin precursor (Allergen Bos d 6) (BSA) - *Bos taurus* (Bovine) | ALBU_BOVIN |
| Ubiquitin cross-reactive protein precursor (Interferon-stimulated protein 15) (IP17) - *Mus musculus* (Mouse) | UCRP_MOUSE |

Figure 17:
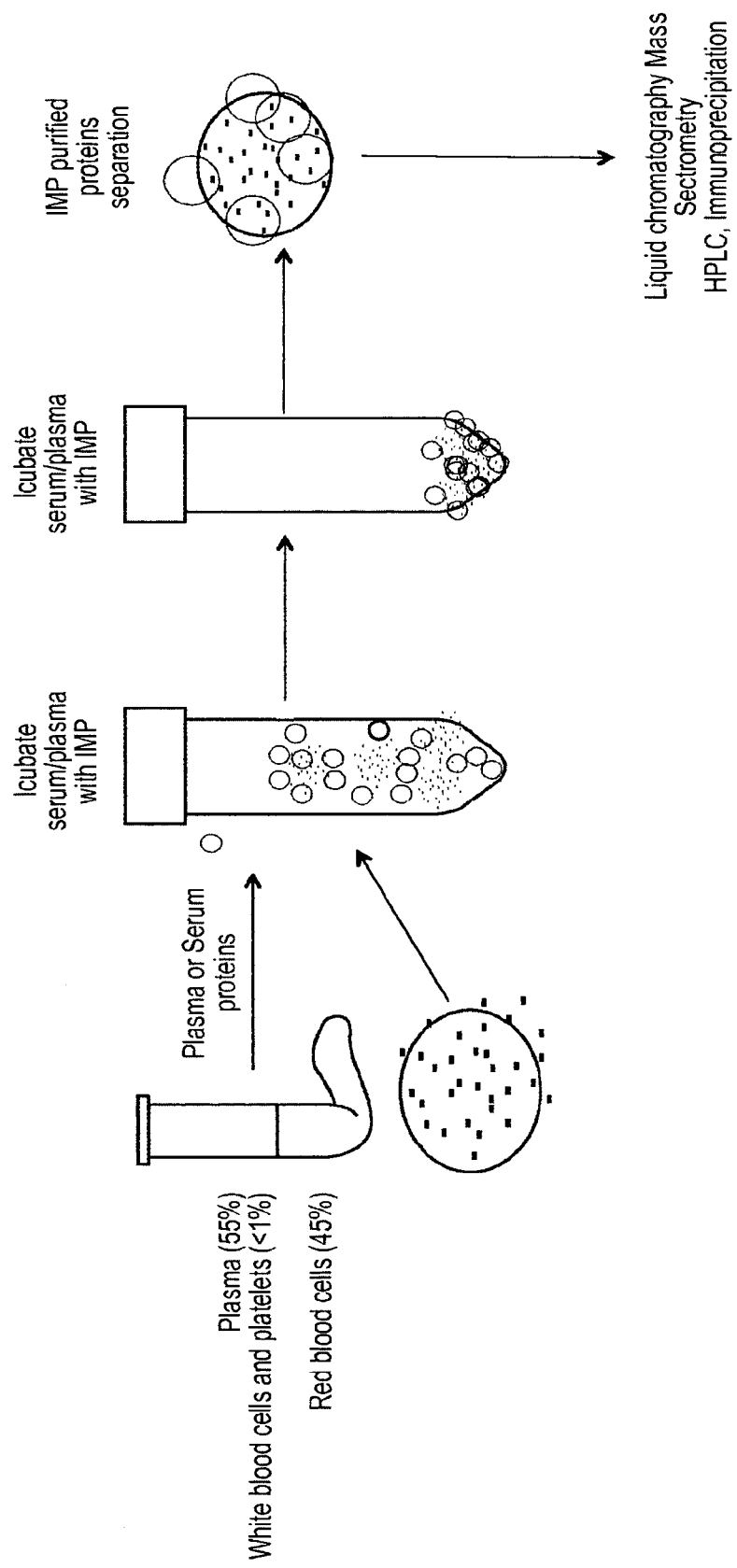
FIG. 17 shows a schematic of negatively charged particles are able to determine the presence or absence of proteins from the serum of a subject in order to determine whether or not the subject is undergoing an inflammatory process.

These results indicate that the particles of the present invention are useful in both acting as a sink to mop up inflammatory mediators, pathological proteins and/or cellular debris such as S100 proteins and/or fatty acid binding protein for example, for example (FIG. 16A), while also being useful in concentrating regulatory proteins such as Annexin 1 (FIG. 16B). Additionally, these results are useful in the diagnostic methods described herein where serum is incubated with IMP either in vitro or in vivo, and proteins are subsequently purified from the IMP by liquid chromatography, mass spectrometry, HPLC or immunoprecipitation, for example, in order to determine/diagnose the presence of an inflammatory immune response in a subject (FIG. 17).

While specific embodiments of the invention have been described and illustrated, such embodiments should be considered illustrative of the invention only and not as limiting the invention as construed in accordance with the accompanying claims.

All patents, applications, and other references cited herein are incorporated by reference in their entireties.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US09919005B2). An electronic copy of the "Sequence Listing" will also be available from the USPTO upon request and payment of the fee set forth in 37 CFR 1.19(b)(3).

What is claimed is:

1. A method of treating an ischemic reperfusion injury in a subject in need thereof comprising administering to said subject an effective amount of a pharmaceutical composition comprising poly(lactic-co-glycolic acid) (PLGA) particles having a zeta potential from −75 mV to 0 mV and a carrier, wherein said particles are free from attached or embedded peptide, antigenic moieties and other additional drugs or therapeutics.

2. The method of claim 1, wherein the particles are carboxylated.

3. The method of claim 1, wherein the particles have a zeta potential between about −50 mV and 0 mV.

4. The method of claim 3, wherein the particles have a zeta potential between about −50 mV and about −40 mV.

5. The method of claim 4, wherein the particles have a zeta potential of about −50 mV.

6. The method of claim 1, wherein the particles have a polylactic acid:polyglycolic acid ratio of 50:50, 80:20, or 90:10.

7. The method of claim 1, wherein the diameter of the particles is between about 0.1 μm to about 10 μm.

8. The method of claim 7, wherein the diameter of the particles is between about 0.3 μm to about 5 μm.

9. The method of claim 8, wherein the diameter of the particles is between about 0.5 μm to about 3 μm.

10. The method of claim 9, wherein the diameter of the particles is between about 0.5 μm to about 1 μm.

11. The method of claim 10, wherein the diameter of the particles is about 0.5 μm.

12. The method of claim 1 wherein the composition is administered orally, nasally, intravenously, intramuscularly, ocularly, transdermally, intraperitoneally, or subcutaneously.

13. The method of claim 12, wherein the composition is administered intravenously.

14. The method of claim 1, wherein the composition further comprises a pharmaceutically acceptable carrier.

15. A method of treating an ischemic reperfusion injury in a subject in need thereof comprising intravenously administering to said subject an effective amount of a pharmaceutical composition comprising poly(lactic-co-glycolic acid) (PLGA) particles having a zeta potential from −75 mV to 0 mV and a carrier, wherein said particles are free from attached or embedded peptide, antigenic moieties and other additional drugs or therapeutics, and wherein said particles have a molar ratio of polylactic acid to polyglycolic acid of about 50:50.

16. The method of claim 15, wherein said particles are carboxylated.

17. The method of claim 15, wherein the diameter of the particles is between about 0.1 μm to about 10 μm.

* * * * *